United States Patent
Rastegar

(10) Patent No.: US 9,910,060 B2
(45) Date of Patent: Mar. 6, 2018

(54) PIEZOELECTRIC-BASED MULTIPLE IMPACT SENSORS AND THEIR ELECTRONIC CIRCUITRY

(71) Applicant: Jahangir S Rastegar, Stony Brook, NY (US)

(72) Inventor: Jahangir S Rastegar, Stony Brook, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 360 days.

(21) Appl. No.: 14/589,933

(22) Filed: Jan. 5, 2015

(65) Prior Publication Data

US 2015/0331008 A1    Nov. 19, 2015

Related U.S. Application Data

(63) Continuation-in-part of application No. 14/225,290, filed on Mar. 25, 2014, now Pat. No. 9,470,497, which is a continuation-in-part of application No. 13/207,355, filed on Aug. 10, 2011, now Pat. No. 8,776,688, which is a continuation-in-part of
(Continued)

(51) Int. Cl.
| | |
|---|---|
| *F42C 11/02* | (2006.01) |
| *G01P 15/00* | (2006.01) |
| *H02N 2/18* | (2006.01) |
| *B01J 31/22* | (2006.01) |
| *C07F 11/00* | (2006.01) |
| *C07D 403/10* | (2006.01) |
| *C07D 207/325* | (2006.01) |
| *C08F 132/08* | (2006.01) |

(52) U.S. Cl.
CPC ......... *G01P 15/001* (2013.01); *B01J 31/2265* (2013.01); *C07D 207/325* (2013.01); *C07D 403/10* (2013.01); *C07F 11/00* (2013.01); *C08F 132/08* (2013.01); *F42C 11/02* (2013.01); *H02N 2/181* (2013.01); *H02N 2/183* (2013.01)

(58) Field of Classification Search
CPC ......... F42C 11/02; F42C 11/008; F42C 11/00; F42C 15/40; F42B 3/121; F42B 3/18; H02N 2/181; H02N 2/183; H02N 2/186; H02N 2/188; G04F 1/005; G04F 10/00
See application file for complete search history.

(56) References Cited

U.S. PATENT DOCUMENTS

| | | | | |
|---|---|---|---|---|
| 3,670,653 A | * | 6/1972 | Lunt | ........................ F42C 11/02 102/210 |
| 3,808,975 A | * | 5/1974 | Stutzle | .................... F42C 13/00 102/210 |

(Continued)

*Primary Examiner* — Benjamin P Lee

(57) ABSTRACT

An electrical energy harvesting device for harvesting electrical energy from a pulsed impact loading event. The device including: a piezoelectric element configured to be loaded and unloaded to a first load level by the pulsed impact loading event; and a first inductor coupled to the piezoelectric element configured to be loaded and unloaded to a second load level by the pulsed impact loading event, wherein the piezoelectric element and the first inductor together operate as a first inductor/capacitor (LC) resonant circuit having a first resonance frequency and wherein the loading of the first inductor lags in time the loading of the piezoelectric element.

24 Claims, 41 Drawing Sheets

Related U.S. Application Data application No. 12/164,096, filed on Jun. 29, 2008, now Pat. No. 8,042,469.

(60) Provisional application No. 60/958,948, filed on Jul. 10, 2007.

(56) References Cited

U.S. PATENT DOCUMENTS

| | | | | |
|---|---|---|---|---|
| 3,850,102 A * | 11/1974 | Morrow | F42C 11/02 | 102/210 |
| 3,853,066 A * | 12/1974 | Campagnuolo | F42C 1/14 | 102/207 |
| 3,952,660 A * | 4/1976 | Davis | F42C 11/00 | 102/207 |
| 3,967,555 A * | 7/1976 | Gawlick | F42C 11/02 | 102/210 |
| 4,015,530 A * | 4/1977 | Dick | F42C 13/02 | 102/213 |
| 4,141,298 A * | 2/1979 | Weidner | F42C 11/06 | 102/210 |
| 4,632,032 A * | 12/1986 | Muller | F42C 11/00 | 102/206 |
| 4,793,256 A * | 12/1988 | Webb | F42C 11/02 | 102/210 |
| 5,033,382 A * | 7/1991 | Webb | F42C 11/02 | 102/210 |
| 5,157,220 A * | 10/1992 | Schaffhauser | F42C 11/02 | 102/210 |
| 5,269,223 A * | 12/1993 | Mattsson | F42C 11/02 | 102/210 |
| 5,377,592 A * | 1/1995 | Rode | F42B 3/122 | 102/206 |
| 5,435,248 A * | 7/1995 | Rode | F42B 3/122 | 102/206 |
| 5,440,990 A * | 8/1995 | Wiedefeld | F42C 11/065 | 102/215 |
| 5,476,044 A * | 12/1995 | Boucher | F42C 11/008 | 102/206 |
| 5,721,391 A * | 2/1998 | Thorsted | F41A 19/58 | 102/218 |
| 5,756,927 A * | 5/1998 | Fixell | F42C 15/40 | 102/215 |
| 6,401,621 B1 * | 6/2002 | Davis | F42C 15/40 | 102/220 |
| 6,729,240 B1 * | 5/2004 | Smith | F42C 15/40 | 102/206 |
| 7,124,689 B2 * | 10/2006 | Davis | F42C 9/147 | 102/215 |
| 7,227,235 B2 * | 6/2007 | Kroupenkine | F42C 19/00 | 257/400 |
| 7,231,874 B2 * | 6/2007 | Rastegar | F41H 11/02 | 102/207 |
| 7,285,868 B2 * | 10/2007 | Wilson | B60C 23/041 | 290/1 R |
| 7,312,557 B2 * | 12/2007 | Rastegar | F42C 11/008 | 102/206 |
| 7,906,861 B2 * | 3/2011 | Guerrero | E21B 41/0085 | 290/1 A |
| 8,151,707 B1 * | 4/2012 | Lasut | F42B 3/18 | 102/215 |
| 8,813,648 B2 * | 8/2014 | Remahl | F42C 11/02 | 102/210 |
| 2003/0041767 A1 * | 3/2003 | Rastegar | F41H 11/02 | 102/207 |
| 2003/0136290 A1 * | 7/2003 | Kolbli | F42C 9/16 | 102/210 |
| 2003/0221575 A1 * | 12/2003 | Walsh | F42B 3/121 | 102/202.5 |
| 2004/0099171 A1 * | 5/2004 | Davis | F42B 3/18 | 102/218 |
| 2007/0204756 A1 * | 9/2007 | Rastegar | D21F 1/0027 | 102/210 |
| 2010/0076714 A1 * | 3/2010 | Discenzo | H02N 2/181 | 702/104 |
| 2010/0133954 A1 * | 6/2010 | Despesse | H02N 2/186 | 310/319 |
| 2012/0012020 A1 * | 1/2012 | Remahl | F42C 11/02 | 102/210 |
| 2012/0280596 A1 * | 11/2012 | Ide | H02N 2/181 | 310/319 |
| 2012/0291650 A1 * | 11/2012 | Aw | F42C 1/02 | 102/207 |
| 2013/0082565 A1 * | 4/2013 | Ide | H02N 2/181 | 310/317 |
| 2013/0082566 A1 * | 4/2013 | Tabata | H02N 2/181 | 310/317 |
| 2013/0082569 A1 * | 4/2013 | Hirabayashi | H01L 41/1136 | 310/319 |
| 2013/0082571 A1 * | 4/2013 | Tabata | H01L 41/1136 | 310/319 |
| 2013/0082572 A1 * | 4/2013 | Oshima | H01L 41/1136 | 310/319 |

* cited by examiner

PIEZOELECTRIC-BASED MULTIPLE IMPACT SENSORS AND THEIR ELECTRONIC CIRCUITRY

CROSS-REFERENCE TO RELATED APPLICATIONS

This application is a continuation in part of U.S. application Ser. No. 14/255,290, filed on Mar. 25, 2014, which is a continuation-in-part application of U.S. application Ser. No. 13/207,355, filed on Aug. 10, 2011, which is a continuation-in-part application of U.S. application Ser. No. 12/164,096 filed on Jun. 29, 2008, which claims the benefit of prior filed U.S. Provisional Application No. 60/958,948 filed on Jul. 10, 2007, the contents of each of which is incorporated herein by reference. This application is related to U.S. Patent Application Publication Nos. 2008/0129151 filed on Dec. 3, 2007 and 2014-0060366 filed on Mar. 2, 2013, the content of each which are also incorporated herein by reference.

BACKGROUND

1. Field

The present disclosure relates generally to sensors for detecting and measuring the acceleration profile induced by an object impacting one or a multiple barriers or other objects or the like that would cause a significant shock loading, and more particularly for piezoelectric-based sensors for detecting and measuring the profile of multiple shock loading caused by the impact of munitions with multiple significant barriers that are at relatively short distances apart.

2. Prior Art

Thermal batteries represent a class of reserve batteries that operate at high temperatures. Unlike liquid reserve batteries, in thermal batteries the electrolyte is already in the cells and therefore does not require a distribution mechanism such as spinning. The electrolyte is dry, solid and non-conductive, thereby leaving the battery in a non-operational and inert condition. These batteries incorporate pyrotechnic heat sources to melt the electrolyte just prior to use in order to make them electrically conductive and thereby making the battery active. The most common internal pyrotechnic is a blend of Fe and $KClO_4$. Thermal batteries utilize a molten salt to serve as the electrolyte upon activation. The electrolytes are usually mixtures of alkali-halide salts and are used with the $Li(Si)/FeS_2$ or $Li(Si)/CoS_2$ couples. Some batteries also employ anodes of Li(Al) in place of the Li(Si) anodes. Insulation and internal heat sinks are used to maintain the electrolyte in its molten and conductive condition during the time of use. Reserve batteries are inactive and inert when manufactured and become active and begin to produce power only when they are activated.

Thermal batteries have long been used in munitions and other similar applications to provide a relatively large amount of power during a relatively short period of time, mainly during the munitions flight. Thermal batteries have high power density and can provide a large amount of power as long as the electrolyte of the thermal battery stays liquid, thereby conductive. The process of manufacturing thermal batteries is highly labor intensive and requires relatively expensive facilities. Fabrication usually involves costly batch processes, including pressing electrodes and electrolytes into rigid wafers, and assembling batteries by hand. The batteries are encased in a hermetically-sealed metal container that is usually cylindrical in shape. Thermal batteries, however, have the advantage of very long shelf life of up to 20 years that is required for munitions applications.

Thermal batteries generally use some type of igniter to provide a controlled pyrotechnic reaction to produce output gas, flame or hot particles to ignite the heating elements of the thermal battery. Currently, the following two distinct classes of igniters are available for use in thermal batteries.

The first class of igniters operates based on externally provided electrical energy. Such externally powered electrical igniters, however, require an onboard source of electrical energy, such as a battery or other electrical power source with related shelf life and/or complexity and volume requirements to operate and initiate the thermal battery. Currently available electric igniters for thermal batteries require external power source and decision circuitry to identify the launch condition and initiate the pyrotechnic materials, for example by sending an electrical pulse to generate heat in a resistive wire. The electric igniters are generally smaller than the existing inertial igniters, but they require some external power source and decision making circuitry for their operation, which limits their application to larger munitions and those with multiple power sources.

The second class of igniters, commonly called "inertial igniters", operate based on the firing acceleration. The inertial igniters do not require onboard batteries for their operation and are thereby used often in high-G munitions applications such as in non-spinning gun-fired munitions and mortars. This class of inertial igniters is designed to utilize certain mechanical means to initiate the ignition. Such mechanical means include, for example, the impact pins to initiate a percussion primer or impact or rubbing acting between one or two part pyrotechnic materials. Such mechanical means have been used and are commercially available and other miniaturized versions of them are being developed for thermal battery ignition and the like.

In general, both electrical and inertial igniters, particularly those that are designed to operate at relatively low impact levels, have to be provided with the means for distinguishing events such as accidental drops or explosions in their vicinity from the firing acceleration levels above which they are designed to be activated. This means that safety in terms of prevention of accidental ignition is one of the main concerns in all igniters.

In recent years, new and improved chemistries and manufacturing processes have been developed that promise the development of lower cost and higher performance thermal batteries that could be produced in various shapes and sizes, including their small and miniaturized versions. However, the existing inertial igniters are relatively large and not suitable for small and low power thermal batteries, particularly those that are being developed for use in fuzing and other similar applications, and electrical igniters require some external power source and decision making circuitry for their operation, making them impractical for use in small and low power thermal battery applications.

In addition, the existing inertial igniters are not capable of allowing delayed initiation of thermal batteries, i.e., initiation a specified (programmed) and relatively long amount of time after the projectile firing. Such programmable delay time capability would allow thermal batteries, particularly those that are used to power guidance and control actuation devices or other similar electrical and electronic devices onboard gun-fired munitions and mortars to be initiated a significant amount of time into the flight. In such applications, particularly when electrical actuation devices are used, a significant amount of electrical power is usually required later during the flight to aggressively guide the projectile towards the target. Thus, by delaying thermal battery initiation to when the power is needed, the performance of the thermal battery is significantly increased and in most cases it would also become possible to reduce the overall size of the thermal battery and its required thermal insulation.

A review of the aforementioned merits and shortcomings of the currently available electrical and inertial igniters clearly indicates that neither one can satisfy the need of many thermal batteries, particularly the small and miniature thermal batteries and the like, for small size igniters that are programmable to provide the desired initiation delay time and to operate safely by differentiating all-fire and various no-fire events such as accidental drops and vibration and impact during transportation and loading and even nearby explosions.

A review of the aforementioned merits and shortcomings of the currently available electrical and inertial igniters also clearly indicates the advantages of electrical initiation in terms of its reliability and small size of electrical initiation elements such as electrical matches, the possibility of providing "programmable" decision making circuitry and logic to achieve almost any desired all-fire and no-fire acceleration profiles with the help of an acceleration measuring sensor, and to provide the means to program initiation of the thermal battery or the like a specified amount of time post firing or certain other detected event, but also their main disadvantage in terms of their requirement of external batteries (or other power sources) and electronic and electric circuitry and logic and acceleration sensors for the detection of the all-fire event. On the other hand, the review also indicates the simplicity of the design and operation of inertial igniters in differentiating all-fire conditions from no-fire conditions without the use of external acceleration sensors and external power sources.

In many applications, an object is subjected to relatively short duration shock loading. This is for example the case when an object is impacted by multiple objects traveling at relatively high speed or if an object traveling at relatively high speed impacts multiple objects or impacts multiple barriers that are positioned at relatively close distances. The latter condition is experienced by munitions impacting multiple barriers of relatively significant strength that are positioned relatively close to each other. In such cases, the main shortcoming of currently available sensors, such as different types of available accelerometers, is that when such barriers induce relatively large shock loading, then before the vibration and other shock loading induced and generally oscillatory outputs from the sensor has been "damped" out, the next shock loading may occur. As a result, it becomes extremely difficult, and many cases impossible, to isolate the sensor response from each shock loading event. For example, the munitions may experience multiple shock loadings of tens of thousands of G that may last 5-10 milliseconds or less and be as little as 5-10 milliseconds or less apart.

In addition, in many applications, such as in munitions, the munitions structure would also exhibit one or more significant mode of vibration, including back and forth stress wave traveling phenomenon, which would further complicate the aforementioned shock loading event profile measurement.

In addition, in most applications, it is highly desirable that sensors for detection and measurement of the profile of the aforementioned multiple shock loading, particularly when such multiple shock loadings occur very short times apart, to be very small so that they would not occupy a considerable volume as well as not to significantly alter the dynamic behavior of the object.

In addition to the above volume requirement and object inertia characteristic alteration reasons, it is highly desirable to provide sensors for shock loading detection and profile measurement that require no, or minimal, external electrical energy for their operation.

SUMMARY

A need therefore exists for miniature electrically initiated igniters for thermal batteries and the like, particularly for use in gun-fired smart munitions, mortars, small missiles and the like, that operate without external power sources and acceleration sensors and circuitry and incorporate the advantages of both electrical igniters and inertial igniters that are currently available. Such miniature electrically initiated igniters are particularly needed for very small, miniature, and low power thermal batteries and other similar applications. For example, flexible and conformal thermal batteries for sub-munitions applications may occupy volumes as small as 0.006 cubic inches (about 100 cubic millimeters). This small thermal battery size is similar in volume to the inertial igniters currently available and used in larger thermal batteries.

An objective is to provide a new class of "inertial igniters" that incorporates electrical initiation of the pyrotechnic materials without the need for external batteries (or other power sources). The disclosed igniters are hereinafter referred to as "electrically initiated inertial igniters". The disclosed "electrically initiated inertial igniters" utilize the firing acceleration to provide electrical power to the igniter electronics and decision making circuitry, start the initiation timing when the all-fire condition is detected, and electrically initiate the pyrotechnic materials at the specified time into the flight. In addition, electrical initiation of pyrotechnic materials is generally more reliable than impact or rubbing type of pyrotechnic initiation. In addition, electronic circuitry and logic are more readily configured to be programmable to the specified all-fire and no-fire conditions.

The method of providing electrical power includes harvesting electrical energy from the firing acceleration by, for example, using active materials such as piezoelectric materials. The method of providing electrical power also includes activation of certain chemical reserve micro-battery using the aforementioned harvested electrical energy, which would in turn provide additional electrical energy to power different components of the "electrically initiated inertial igniter".

The disclosed "electrically initiated inertial igniters" can be miniaturized and produced using mostly available mass fabrication techniques used in the electronics industry, and should therefore be low cost and reliable.

To ensure safety and reliability, all inertial igniters, including the disclosed "electrically initiated inertial igniters" must not initiate during acceleration events which may occur during manufacture, assembly, handling, transport, accidental drops, etc. Additionally, once under the influence of an acceleration profile particular to the firing of the ordinance, i.e., an all-fire condition, the igniter must initiate with high reliability. In many applications, these two requirements compete with respect to acceleration magnitude, but differ greatly in their duration. For example:

An accidental drop may well cause very high acceleration levels—even in some cases higher than the firing of a shell from a gun. However, the duration of this accidental acceleration will be short, thereby subjecting the inertial igniter to significantly lower resulting impulse levels.

It is also conceivable that the igniter will experience incidental long-duration acceleration and deceleration cycles, whether accidental or as part of normal handling or vibration during transportation, during which it must be guarded against initiation. Again, the impulse input to the igniter will have a great disparity with that given by the initiation acceleration profile because the magnitude of the incidental long-duration acceleration will be quite low.

The need to differentiate accidental and initiation acceleration profiles by their magnitude as well as duration necessitates the employment of a safety system which is capable of allowing initiation of the igniter only during all-fire acceleration profile conditions are experienced.

In addition to having a required acceleration time profile which should initiate the igniter, requirements also commonly exist for non-actuation and survivability. For example, the design requirements for actuation for one application are summarized as:

1. The device must fire when given a [square] pulse acceleration of 900 G±150 G for 15 ms in the setback direction.

2. The device must not fire when given a [square] pulse acceleration of 2000 G for 0.5 ms in any direction.

3. The device must not actuate when given a ½-sine pulse acceleration of 490 G (peak) with a maximum duration of 4 ms.

4. The device must be able to survive an acceleration of 16,000 G, and preferably be able to survive an acceleration of 50,000 G.

The electrical and electronic components of the disclosed electrically initiated inertial igniters are preferably fabricated on a single platform ("chip"), and are integrated into either the cap or interior compartment of thermal batteries or the like, in either case preferably in a hermetically sealed environment. The disclosed electrically initiated inertial igniters should therefore be capable of readily satisfying most munitions requirement of 20-year shelf life and operation over the military temperature range of −65 to 165 degrees F., while withstanding high G firing accelerations.

Some of the features of the disclosed "electrically initiated inertial igniters" for thermal batteries for gun-fired projectiles, mortars, sub-munitions, small rockets and the like include:

1. The disclosed (miniature) electrically initiated inertial igniters are capable of being readily "programmed" to almost any no-fire and all-fire requirements or multiple predefined setback environments. For these reasons, the disclosed miniature electrically initiated inertial igniters are ideal for almost any thermal battery applications, including conformal small and low power thermal batteries for fuzing and other similar munitions applications.

2. The disclosed (miniature) electrically initiated inertial igniters can be fabricated entirely on a chip using existing mass fabrication technologies, thereby making them highly cost effective and very small in size and volume.

3. The disclosed (miniature) electrically initiated inertial igniters do not require any external power sources for their operation.

4. In those applications in which the thermal battery power is needed for guidance and control close to the target, the disclosed (miniature) electrically initiated igniters can be programmed to initiate ignition long after firing, thereby eliminating the effects of thermal battery cooling.

5. The disclosed (miniature) electrically initiated inertial igniters are solid-state in design. Their final total volume is therefore expected to be significantly less than those of currently available electrical and inertial igniters.

6. The disclosed (miniature) electrically initiated inertial igniter is capable of electric initiation of $Zr/BaCrO_4$ heat paper mixtures or their equivalents as is currently practiced in thermal batteries.

7. The disclosed (miniature) electrically initiated inertial igniters are readily packaged in sealed housings using commonly used mass-manufacturing techniques. As a result, safety and shelf life of the igniter, thermal battery and the projectile is significantly increased.

8. The solid-state and sealed design of the disclosed (miniature) electrically initiated inertial igniters should easily provide a shelf life of over 20 years and capability to operate within the military temperature range of −65 to 165 degrees F.

9. The disclosed (miniature) electrically initiated inertial igniters can be designed to withstand very high-G firing accelerations in excess of 50,000 Gs.

10. The disclosed (miniature) electrically initiated inertial igniters are programmable for any no-fire and all-fire requirements and delayed initiation time following an all-fire event. The disclosed igniters could therefore be used with other electrically activated igniters for thermal batteries, munitions or other similar applications.

11. The disclosed (miniature) electrically initiated inertial igniters can be designed to conform to any geometrical shape of the available space and thermal batteries.

Accordingly, an electrically initiated inertial igniter for a munition is provided. The electrically initiated inertial igniter comprising: an electrical energy generating device configured to generate a voltage over a duration responsive to an acceleration of the munition; a first electrical storage device connected to the electrical energy generating device through a voltage divide circuit to receive a portion of the voltage over the duration; a second electrical storage device connected to the electrical energy generating device to accumulate the voltage; and a circuit powered by a connection to the electrical energy generating device, the circuit configured to determine an all-fire condition based on both a connection to the first electrical storage device that receives the portion of the voltage and the duration of voltage generation and a predetermined accumulated voltage of the second electrical storage device.

The electrical energy generating device can be a piezoelectric generator.

The electrically initiated inertial igniter can further comprise a resistor connected to the first electrical storage device to drain a charge accumulated in the first electrical storage device resulting from non-firing events.

The circuit can comprise: a reset circuit; and a comparator comprising: a first input connected to the first electrical storage, a second input connected to a reference voltage, a third input connected to the reset circuit, and an output that produces an indication of the all-fire condition in response to the predetermined accumulated voltage in the electrical storage device, wherein the reset circuit is configured to reset the indication when the electrical energy generating device begins to generate a voltage.

Also provided is a method for electrically initiating an inertial igniter for a munition. The method comprising acts of: providing an electrical energy generating device to generate a voltage over a duration responsive to an acceleration of the munition; providing a first electrical storage device connected to the electrical energy generating device through a voltage divide circuit to receive a portion of the voltage over the duration; providing a second electrical storage device connected to the electrical energy generating device to accumulate the voltage; and providing a circuit powered by a connection to the electrical energy generating device, the circuit determining an all-fire condition based on both a connection to the first electrical storage device that receives the portion of the voltage and the duration of voltage generation and a predetermined accumulated voltage of the second electrical storage device.

In addition, in certain applications, the electrical energy that is generated by the electrical energy generating element, for example the piezoelectric element, of the device may be desired to be partially or completely stored in an electrical energy storage device such as a capacitor for later use by the system electronics or the like, such as for powering a timing and/or sensory circuitry for initiation of a thermal battery after a prescribed amount of time has elapsed and/or after a certain event has been detected. In such applications, it is highly desirable for the electrical energy being harvested from the electrical energy generating element to be highly efficient to make it possible to minimize the size of the energy harvesting device and its components.

It will also be appreciated by those skilled in the art that when harvesting electrical energy from shock loading such as those experienced by gun firing or impact or other similar very short duration "pulsed" loading events, the mechanical to electrical energy converting elements such as piezoelectric elements or magnet and coil elements used for this purpose are subjected to very short duration "pulsed" excitation. Currently used electrical energy collection and capacitor storage methods are, however, extremely inefficient when the "pulse" duration is very short and sometimes in the order of micro-seconds. Methods and means are highly desirable to be developed for efficient harvesting of generated electrical energy that is generated by electrical energy generators such as piezoelectric elements or magnet and coil elements in the form of very short duration "pulses".

Accordingly, methods and devices are provided for highly efficient harvesting (collecting) of electrical energy from electrical energy generators such as piezoelectric elements or magnet and coil elements when the generated electrical energy is in the form of very short duration pulses such as those encountered as a result of gun firing (particularly in small and medium caliber rounds) and upon target impact or the like or in devices specifically designed to subject the electrical energy generators to intermittent short duration pulses.

A need therefore exists for miniature sensors for use in objects, such as munitions, for detecting shock loading and measuring the shock loading profile in general and when the object is subjected to multiple shock loadings that are experienced very short times apart. In particular, there is a need for miniature sensors for munitions to detect multiple shock loading due to impact with significant barriers that are relatively close to each other and to measure the shock loading profile, i.e., the shock loading strength as a function of time.

There is also a need for methods of designing miniature sensors and their electronics for use in objects, such as munitions, for detecting shock loading and measuring the shock loading profile in general and when the object is subjected to multiple shock loadings that are experienced very short times apart. In particular, there is a need for methods to design and fabricate miniature sensors and their electronics for munitions to detect multiple shock loading due to impact with significant barriers that are relatively close to each other and to measure the shock loading profile. Such sensory systems (sensor and its electronics) must be capable of isolating the sensor response from each shock loading event, noting that munitions may experience multiple impact induced shock loadings that are of tens of thousands of G in magnitude that may last 5-10 milliseconds or less and be as little as 5-10 milliseconds or less apart.

There is also a need for miniature sensors for use in objects such as munitions for detecting shock loading and measuring the shock loading profile in general and when the object is subjected to multiple shock loadings that are experienced very short times apart. In munitions, such shock loadings may be due to firing setback, expulsion of sub-munitions, firing of range extension rockets, or the like, or due to munitions impact with significant barriers and/or target objects or the like.

In addition, since in most applications, such as in munitions, the structure of the munitions would exhibit one or more significant modes of vibration, including back and forth stress wave traveling phenomenon, a need exists for methods to design sensors and their electronics and such sensors and their electronics that are capable of isolating the multiple shock loading events being detected and measured to ensure measurement of each individual shock loading profile with appropriate level of precision.

In addition, a need also exists for methods to design sensors and their electronics and such sensors and their electronics for detection and measurement of the profile of the aforementioned multiple and shock loading, particularly when such multiple shock loadings occur very short time apart to be very small so that they would not occupy a considerable volume as well as not to significantly alter the dynamic behavior of the object.

There is also a need for methods to design sensors and their electronics and such sensors and their electronics for detection and measurement of the profile of the aforementioned multiple and shock loadings that require no or minimal external electrical energy for their operation.

Accordingly, methods and devices are provided for miniature sensors and their electronics for multiple shock detection and measurement where the shock loading events that are large in amplitude and relatively very short in duration and occurs with minimal time separation.

BRIEF DESCRIPTION OF THE DRAWINGS

These and other features, aspects, and advantages of the apparatus of the present invention will become better understood with regard to the following description, appended claims, and accompanying drawings where:

FIG. 5 illustrates an alternative piezoelectric powered programmable event detection and logic circuitry for differentiating all no-fire events from all-fire events and to initiate igniter with a programmed time delay for medium caliber rounds and the like.

FIG. 14 illustrates the method of using the safety and all-fire detection circuitry of embodiment of FIG. 13 to design passive initiators for pyrotechnic material or the like.

DETAILED DESCRIPTION OF THE PREFERRED EMBODIMENT

Figure 1:
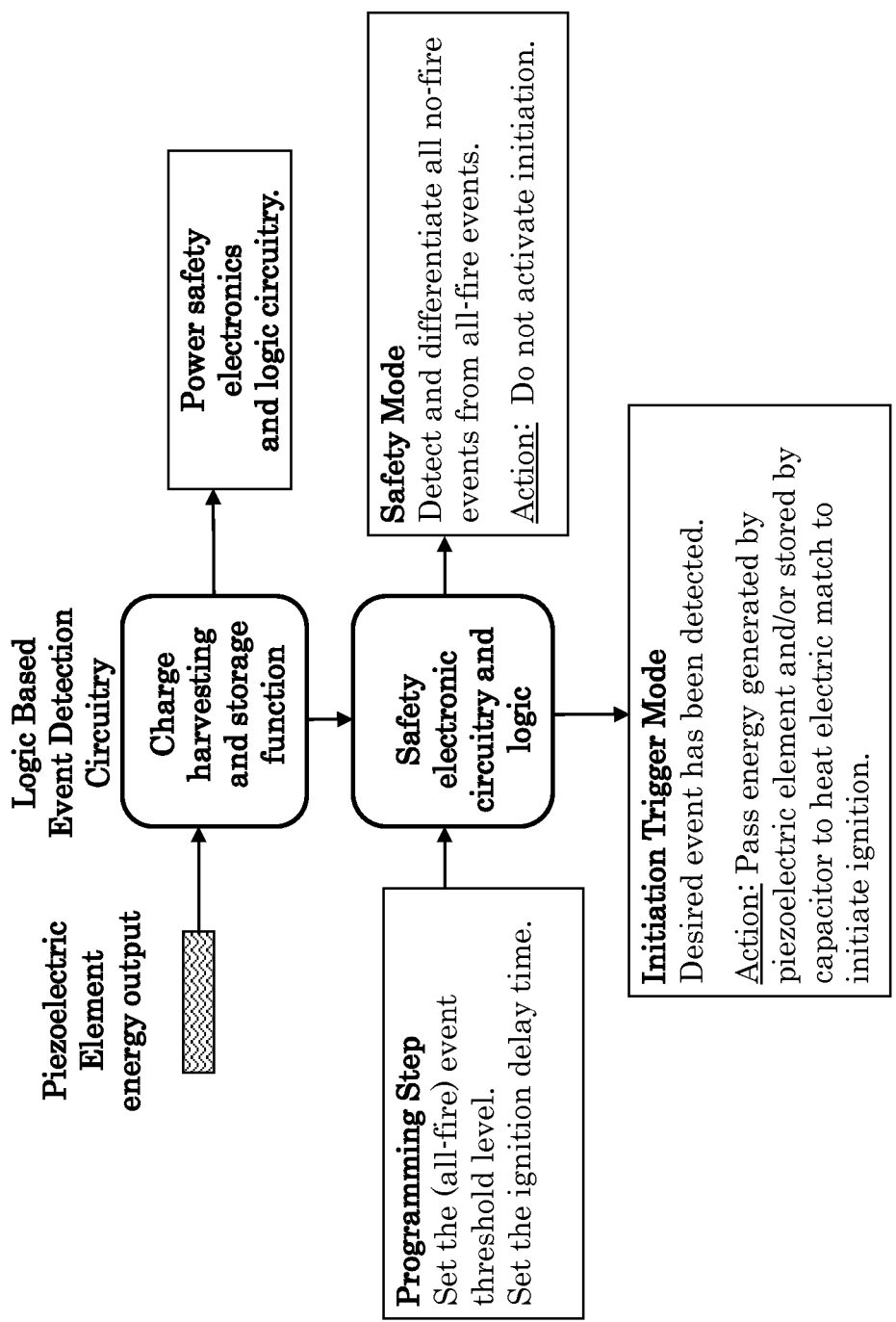
FIG. 1 illustrates the block diagram of the first class of the disclosed piezoelectric element based class of programmable electrically initiated inertial igniter embodiments.

The block diagram of a first embodiment of a programmable electrically initiated inertial igniter is shown in FIG. 1. In this embodiment, an appropriately sized piezoelectric element (different options of which are described later in this disclosure) is used, which responds to the axial accelerations and/or decelerations of the munitions or the like, to which it is affixed via a thermal battery or the like. In response to the aforementioned axial accelerations and/or decelerations of the piezoelectric element, a charge is generated on the piezoelectric element due to the resulting forces acting on the piezoelectric element due to its mass and the mass of other elements acting on the piezoelectric element (if any). As a result, the sign of the corresponding voltage on the piezoelectric element would readily indicate the direction of the axial acceleration that is applied to the munitions due to the firing or accidental dropping or other similar no-fire conditions.

However, the detection of the generated piezoelectric element voltage levels alone is not enough to ensure safety by distinguishing between no-fire and all-fire conditions. This is the case since in certain accidental events such as direct dropping of the igniter, thermal battery and/or the munitions, the acceleration levels that are experienced by the igniter may be well above that of the specified all-fire acceleration level requirements. For example, when an igniter is dropped over a hard surface, it might experience acceleration levels of up to 2000 Gs for an average duration of up to 0.5 msec. However, the all-fire acceleration level may be significantly lower, for example around 500 Gs, with the difference being in its duration, which may be around 8-15 msec.

In addition, it is desired to harvest the electrical energy generated by the piezoelectric elements and store the electrical energy in a storage device such as a capacitor to power the igniter electronics circuitry and logics and to initiate the electrical ignition element when all-fire conditions are detected. Then if the voltage of the storage device such as the capacitor is to be monitored for the detection of the all-fire conditions, then very long term vibration type oscillatory accelerations and decelerations of relatively low levels which may be experienced during transportation or the like may also bring the voltage of the storage capacitor to the level corresponding to the all-fire levels. It is therefore evident that the voltage levels generated by active elements such as piezoelectric elements alone, or total accumulated energy cannot be used to differentiate no-fire conditions from all-fire conditions in all munitions since it may have been generated over relatively long periods of time due to vibration or other oscillatory motions of the device during transportation or the like.

Thus, to achieve one single electrically initiated inertial igniter design that could work for different types of munitions and the like, the igniter has to be capable of differentiating no-fire high-G but low duration acceleration profiles from those of all-fire and significantly longer duration acceleration profiles. The device must also differentiate between low amplitude and long term acceleration profiles due to vibration and all-fire acceleration profiles.

Obviously, if in certain munitions the all-fire acceleration levels were significantly higher than the no-fire acceleration levels, then the aforementioned voltage levels of the piezoelectric element used in an igniter device could be used as a threshold to activate the heating element (wire electrode) to initiate the pyrotechnic material or initiate the initiation "delay timing clock". However, since the all-fire acceleration levels are lower than the no-fire acceleration levels in some munitions, therefore to achieve one single electrically initiated inertial igniter design that could work for all different types of munitions; the igniter has to be capable of differentiating the two events based on the duration of the experienced acceleration profile. In any case, the igniter device must still differentiate long term low acceleration vibration profiles from those of all-fire acceleration profiles.

The block diagram of FIG. 1 shows the general schematics of an embodiment of an electrically initiated inertial igniter. In the igniter of FIG. 1, at least one piezoelectric element is used to generate a charge (electrical energy) in response to the acceleration and/or deceleration profile that it experiences due to all no-fire and all-fire events. The charge generated by the piezoelectric element is then used to power the detection and safety electronics and logic circuitry and the detonation capacitor and its activation circuitry, as described later in this disclosure. In one embodiment, the electrical energy from the piezoelectric element is stored in a separate and relatively small capacitor that would act as a controlled power source to power the logic circuit. This power, supplied by the charged capacitor, would be used to activate the monitoring circuit logic to provide functionality, allowing for a range of triggering events to be detected from the piezoelectric element that are not directly coupled to peak voltage or energy detection of the piezoelectric element. In this way, circuits can be designed as described below to prevent detection of momentary spike voltage that could be accidentally generated by random vibrations or accidental droppings or other similar accidental events, indicating a false ignition condition.

The design of the electronics of a programmable electrically initiated inertial igniter is intended to address the following two basic requirements. The first requirement is to ensure safety and reliability of the thermal battery which must not be initiated during accidental drops, transportation vibration, manufacturing or other handling, miss-fire conditions and the like. The second requirement, which is achievable in a miniature igniter only with electronics circuitry, is related to one of the key benefits added by electrically operated ignition systems, i.e., the control of the time of battery initiation, which would allow munitions design engineer to have better control over the power budget and the mission profile of the guided rounds. Furthermore, by having the ability to initiate thermal battery at any point of time during the flight of a round allows munitions designer to optimize the size and efficiency of the thermal battery by operating it at optimum temperature and thereby reduce its required size.

The following two basic and general event detection, safety and ignition electronics and logic circuitry options may be used in the various embodiments disclosed herein. It is, however, appreciated by those skilled in the relevant art that other variations of the present detection and logic circuitry may also be constructed to perform the desired functions, which are intended to be within the scope and spirit of the present disclosure.

Figure 2:
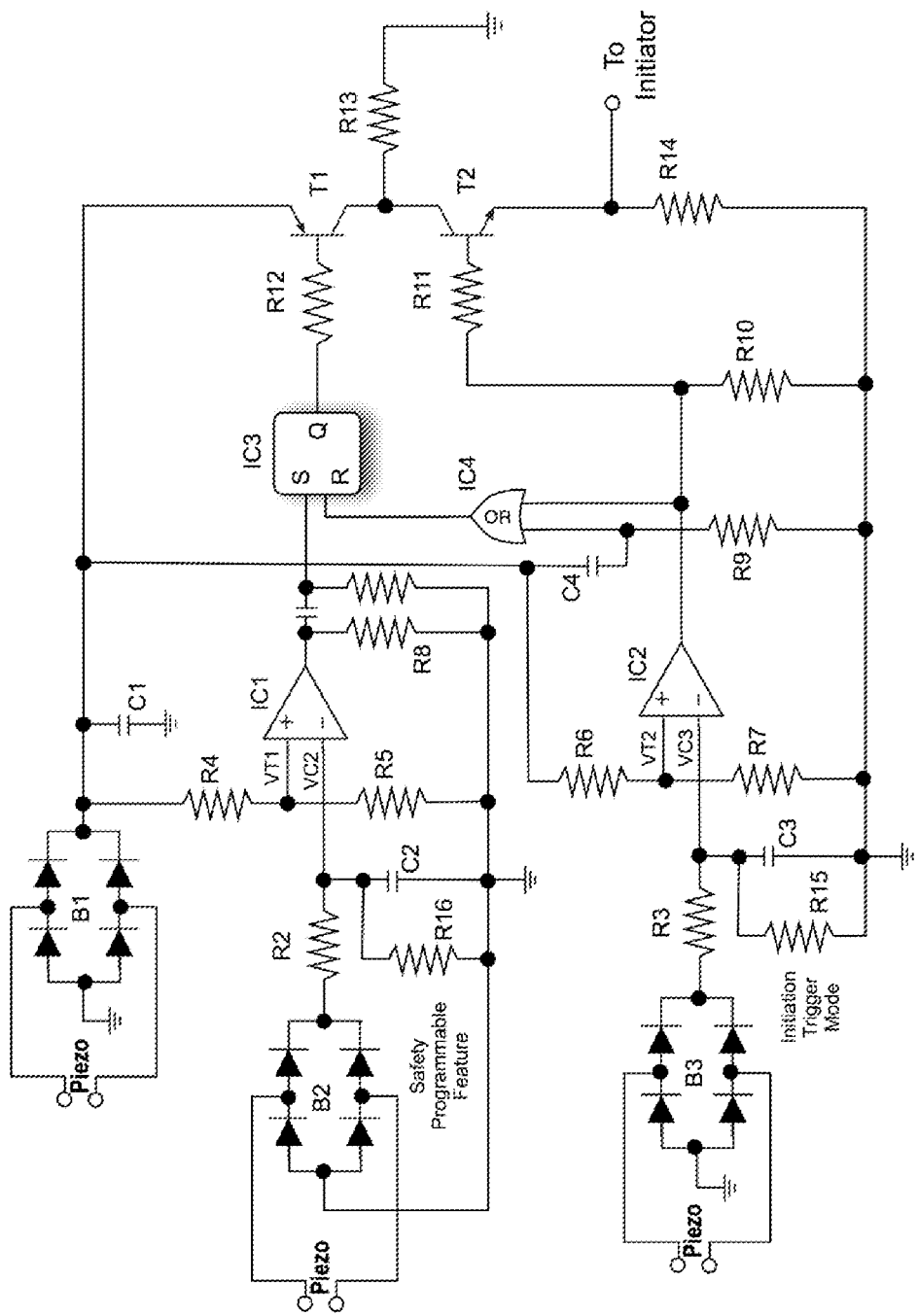
FIG. 2 illustrates the piezoelectric powered programmable event detection and logic circuitry for differentiating all no-fire events from all-fire events and to initiate igniter only when all-fire event is detected.

FIG. 2 shows the basic diagram of one possible design of the electronics circuitry for use in a piezoelectric element powered electrically initiated inertial igniter. The circuitry shown in FIG. 2 is not designed to provide a programmable initiation time delay. This feature is shown in a subsequent embodiment described below. The circuitry functions as a reusable power source based on harvesting energy from the at least one piezoelectric element and storing the harvested energy in the capacitor C1. A dedicated safety feature function (Safety Programming Feature) detects accidental drop or other accidental vibration or impact and determines when it is safe to initiate the battery. A third dedicated function (Initiation Trigger Mode) operates the initiation device which starts the battery initiation process, i.e., to ignite the igniter pyrotechnic material. The circuit incorporates circuitry to compare thresholds of energy generated by events and compares these thresholds with appropriately selected reference voltages at IC1 and IC2 to operate logic that drives the output switching stages T1 and T2.

The circuitry in FIG. 2 receives energy from at least one piezoelectric element that converts mechanical energy harvested from the firing acceleration into electrical charge. Diode bridge B1, rectifies this energy and dumps it into the capacitor C1 which is sufficiently large to serve as a power supply to the rest of the circuitry. The diode bridge B2 converts a very small portion of the energy generated by the piezoelectric generator to operate the Safety Programmable Feature and charges the capacitor C2. The energy stored in the capacitor C2 is measured by the resistor R2 and discharge resistor R16. The voltage at C2 (VC2) is compared with (VT1) at the midpoint of R4 and R5. When VC2 is higher than VT1, the output of IC1 become transitions to a high state and sets flip-flop IC3 and the flip-flop output Q transitions to a high state which causes switching transistor T1 to open and not allow power from reaching the initiator.

The initiator trigger mode operates in a similar fashion except that the time constant of R3 and C3 and bleed resistor R15 is significantly greater than the time constant of the Safety Programmable Feature. Similar to the operation of IC1, IC2 verifies that the voltage at C3 (VC3) is greater than the voltage VT2. When this occurs the output of IC2 transitions to a high state and causes switching transistor T2 to conduct and power the initiator. Note that this could only happen if the transistor T1 is enabled to conduct (IC1 output, Q, is low).

The logic circuits IC3 and IC4 operate to ensure that the initiator cannot be activated when accidental energy is generated by the piezoelectric element, such as during an accidental drop, transportation vibration or other handling situations. The sequence of operation is as follows: when the power first turns on, IC3 is reset by the OR circuit, this ensures that IC3 is now ready to detect accidental energy. Note that this enables T1 to provide power to T2. However, switching transistor T2 is open which prevents T2 from powering the initiator of the battery. The function of the OR circuit is to initialize IC3 when the power first turns on and also to initialize IC3 when an all-fire signal occurs. Initializing IC3 will allow the firing circuit comprised of switching transistor T1 and T2 to be able to power the initiator.

Figure 3:
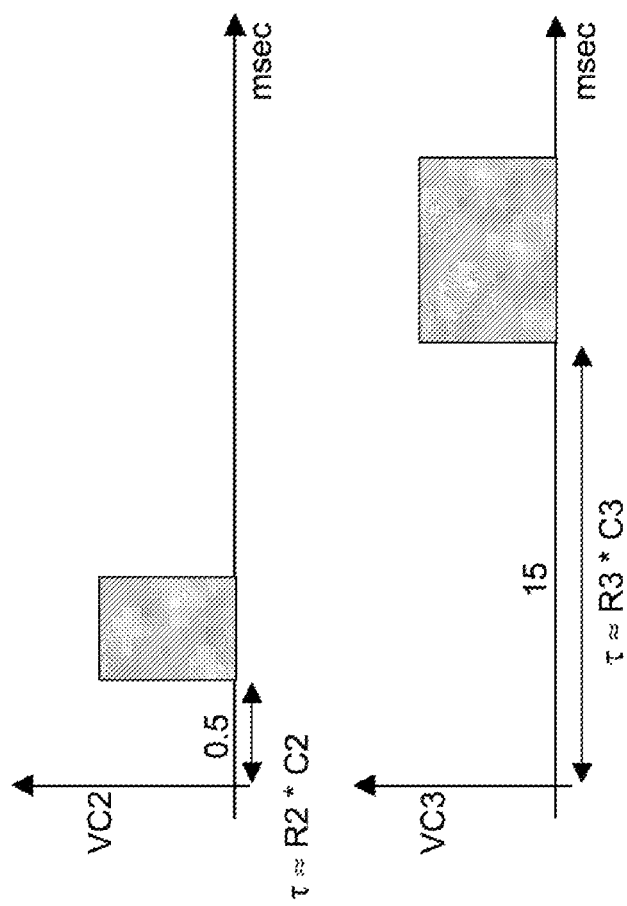
FIG. 3 illustrates a comparison of an accidental drop from the firing acceleration induced voltages.

The overall functionality of the electrically initiated inertial igniter circuitry is controlled by the Safety Programmable Feature (SPF) time constant and by the Initiation Trigger Mode (ITM) time function. For example, for the aforementioned no-fire and all-fire requirements, the SPF time constant is 0.5 msec and the ITM time constant is 15 msec. Thus the safety feature will always occur first as shown in FIG. 3. In situations such as transportation of the device in which the thermal battery or the like is mounted, the device will be subjected to continuing vibration or vibration like oscillatory loading. In such situations, when the vibration continues, the present device would still provide for safety and prevents the initiator from being powered. The safety cushion is governed by a time constant of 14.5 msec, which is controlled by both R2 and R3.

Figure 4:
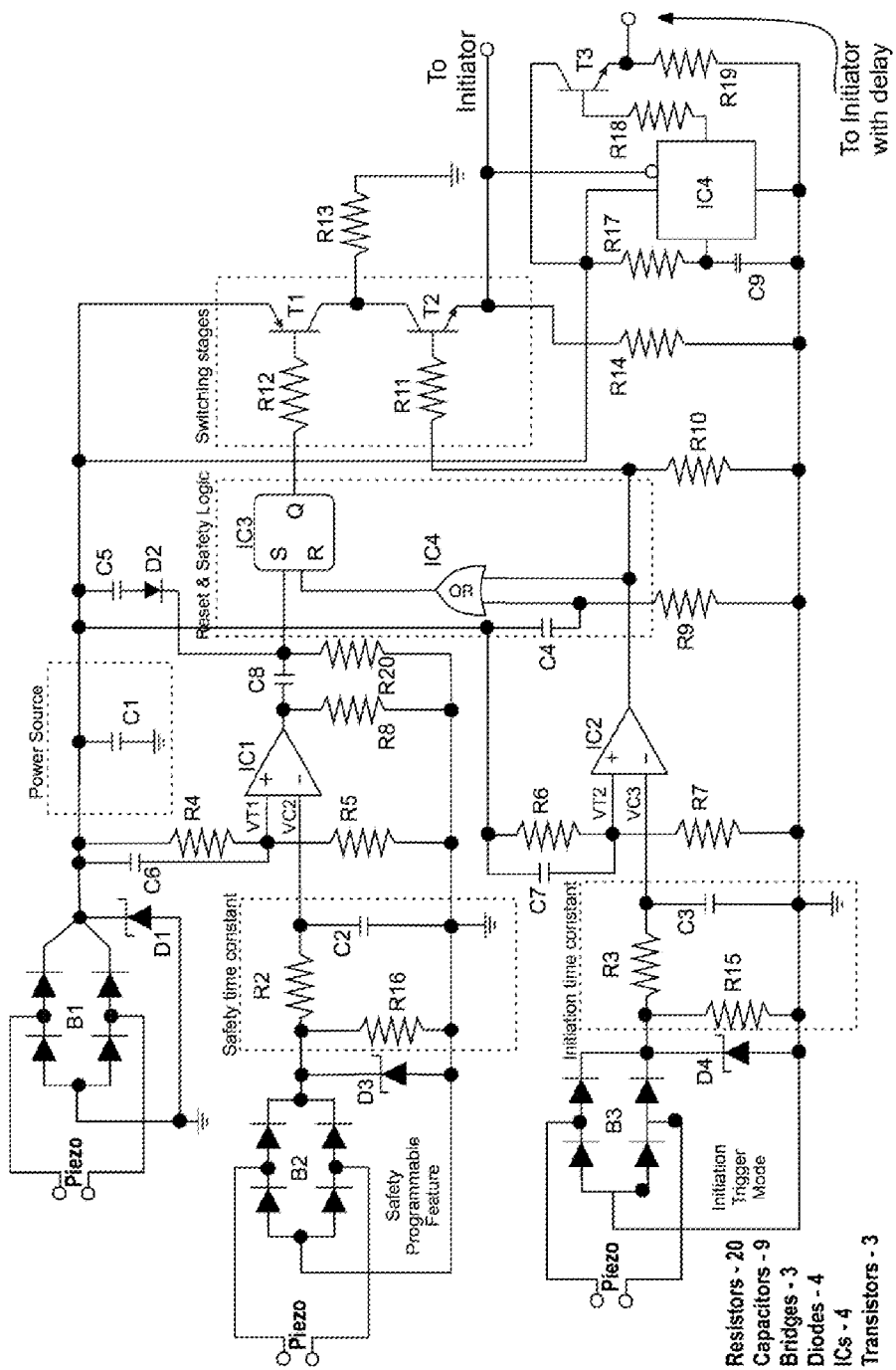
FIG. 4 illustrates an alternative piezoelectric powered programmable event detection and logic circuitry for differentiating all no-fire events from all-fire events and to initiate igniter with a programmed time delay following all-fire event detection.

FIG. 4 shows the diagram of another possible design of the piezoelectric element powered electronics circuitry with programmable initiation time delay feature for use in the disclosed electrically initiated inertial igniters. This design includes an integrated capability to delay the initiation signal by a selected (programmed) amount of time, which could be in seconds and even minutes or more.

In the design shown in FIG. 4, power stored in power supply capacitor C1 is harvested similarly from the at least one piezoelectric element and rectified by the bridge rectifier B1. The voltage at C1 rises to the operational value and it is now ready to start powering the electronics, however, during the transitional state it is very important that the comparator IC1 and IC2, and the OR gate be reset to its desired output value. Capacitors C6 and C7, stabilize and reset IC1 and IC2, respectively, and capacitor C4 resets the IC3, which ensures that switching transistor T1 is ready for operation. A second enhancement of the design shown in FIG. 4 compared to that of the design shown in FIG. 2 is related to the safe operation of the rectified output of the at least one piezoelectric element at the bridge rectifiers output. Diodes D1, D3 and D4 are clamping and transient suppression diodes. These devices ensure that high transient values of voltages produced by the piezoelectric elements do not reach the electronic circuits.

In the event detection and logic circuitry of FIG. 4, a programmable time delay capability to delay the signal to initiate the igniter is also incorporated. In this circuitry design, IC4, the resistor R17 and the capacitor C9 provide the time constant for the output of IC4 at R18 to provide a delayed output to the igniter initiator circuit. The delayed output is determined by the values of R17 and C9. This circuitry obviously offers for both non-delayed as well as delayed output depending on the application. Obviously any other programmable timing device may be used instead.

In certain applications such as medium caliber projectiles, the firing acceleration is very high, for example up to 55,000 Gs and even higher, therefore significantly higher than any accidental accelerations that may be experienced due to dropping. In addition, the volume available for the thermal battery and its igniter is very small.

For such applications, it is preferable that the battery be kept in its inactive state throughout the gun launch and until the acceleration forces resulting from setback and set forward have been significantly abated. For this reason, it is advantageous that initiation of the thermal battery be delayed after launch until the projectile has exited the gun barrel. For such applications, the event detection, safety and ignition electronics and logic and initiation time delay circuitry can be significantly simplified.

Figure 5:
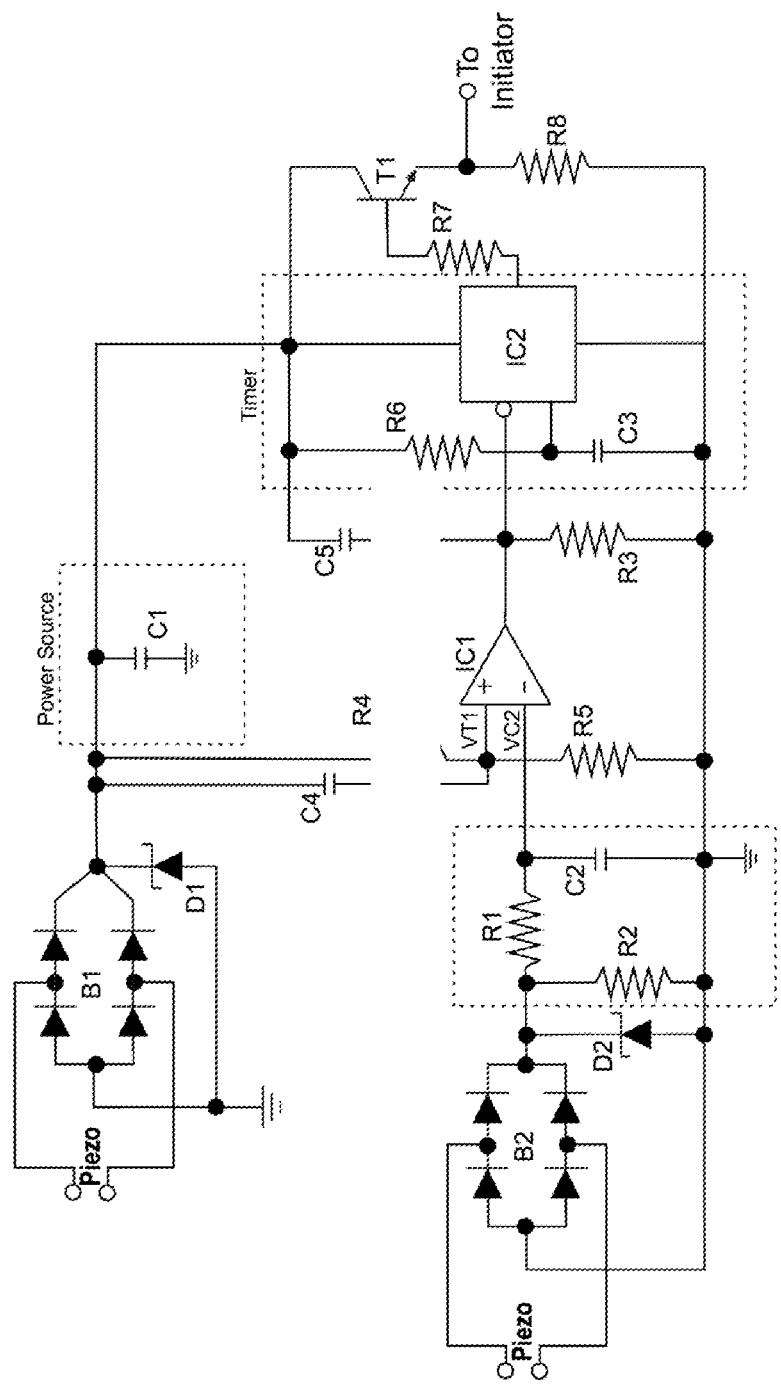

FIG. 5 shows a design of a circuit that will measure the setback acceleration by means of the at least one piezoelectric element. The signal produced by the piezoelectric element due to the setback acceleration is rectified and monitored by IC1 for peak amplitude and duration. These two parameters create a voltage (VC2) which will be compared by IC1. When voltage VC2 becomes higher than voltage VT1, IC1 will output a voltage which will reset IC2. At reset, IC2 will initiate a count of time which will be governed by the value of resistor R6 and capacitor C3. The output of IC2 will be buffered by switching transistor T1 which powers the initiator.

Figure 6:
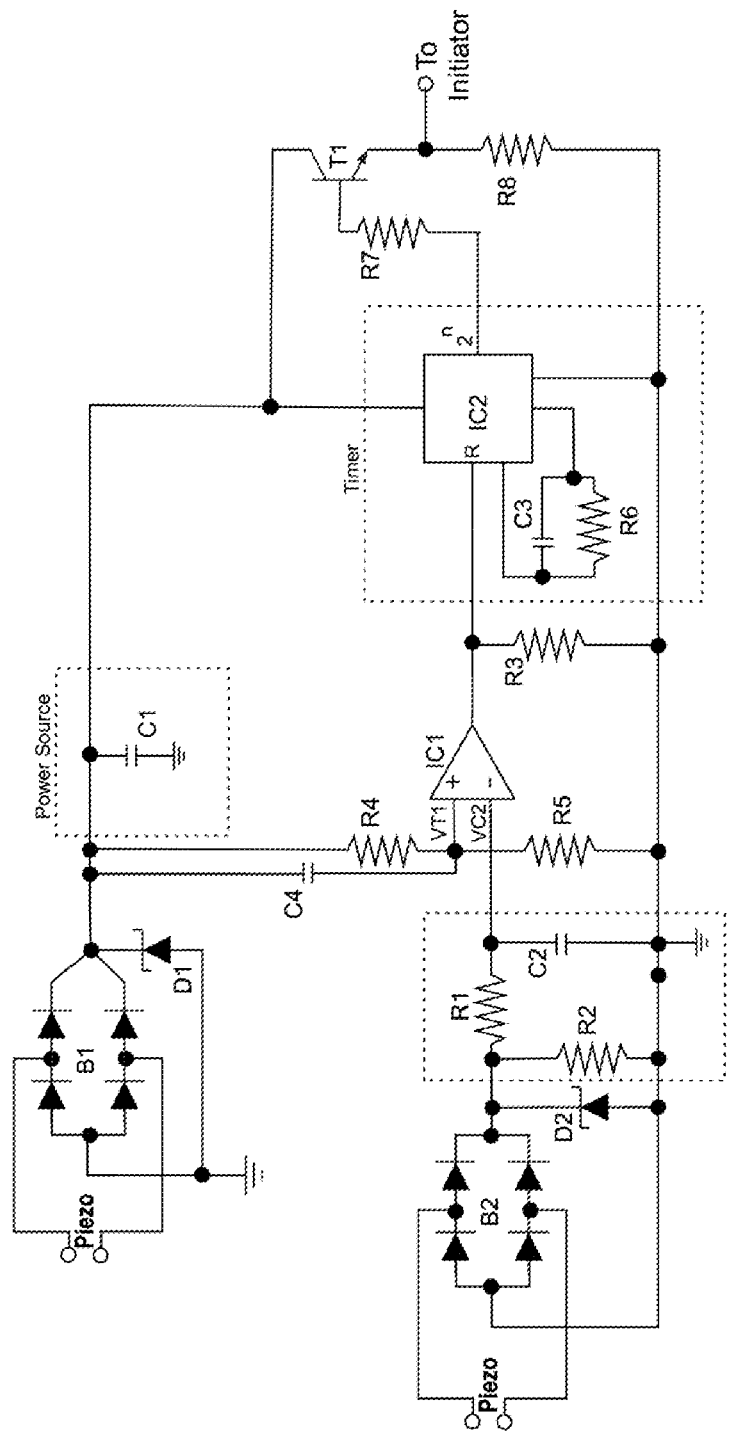
FIG. 6 illustrates a piezoelectric powered programmable event detection and logic circuitry design for event detection and initiation for operation over time periods ranging from minutes to days.

There are also military and civilian applications that require certain sensors be deployed and remain waiting for certain events for relatively long periods of time, ranging from minutes to hours or even days. To accomplish this purpose, a new type of timer will be employed to provide such a dynamic range (minutes to days) as shown in FIG. 6. IC2 can be programmed to deliver delay times from minutes to days by the use of a binary type counter which uses the clock generated by the parallel combination of R6 and C3 and multiplying it by a binary count depending on which output $2^n$ is used.

In the circuitry shown in FIG. 6, the piezoelectric element will detect a launch or impact induced acceleration and/or deceleration, and the signal produced by the launch and/or impact forces will be rectified and detected by R1 and C2. The time constant provided by R1 and C2 will test the signal from the piezoelectric element for duration, and the comparison of the threshold voltage VC2 compared with VT1 will test the signal for amplitude threshold. When the threshold has been detected, IC1 will reset the binary counter IC2 which will start counting time. When the selected time delay has been reached, the output of counter will switch T1, upon which the initiator is powered.

Figure 7:
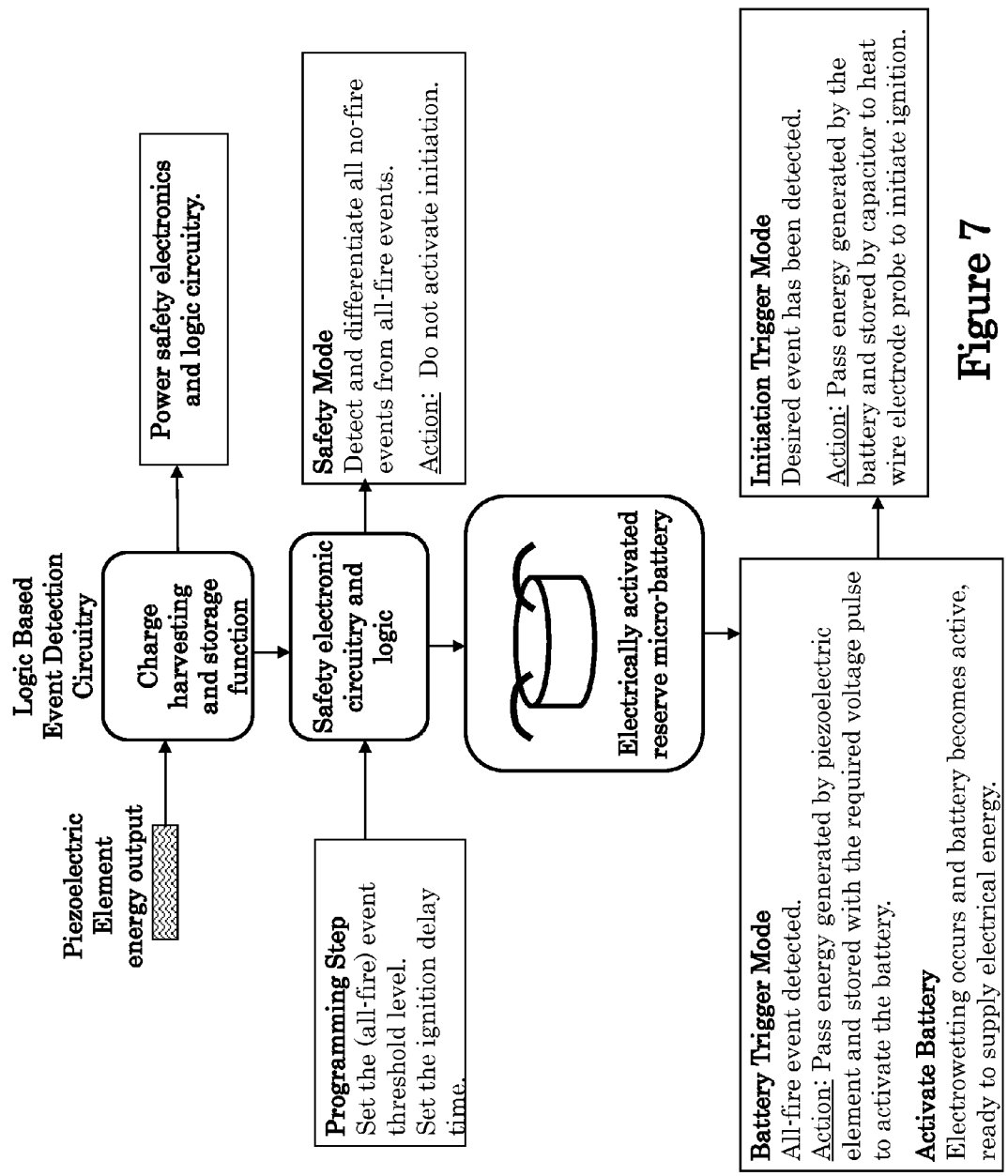
FIG. 7 illustrates the block diagram of the second class of the disclosed piezoelectric element based programmable electrically initiated inertial igniter embodiments employing reserve electrically activated micro-batteries for pyrotechnic initiation.

The block diagram of FIG. 7 shows the general schematics of another embodiment of electrically initiated inertial igniters. In this class of igniters, at least one piezoelectric element is used to generate a charge (electrical energy) in response to the acceleration and/or deceleration profile that it experiences due to all no-fire and all-fire events. The charge generated by the piezoelectric element is then used to power the detection and safety electronics and logic circuitry and possibly partially the detonation capacitor and its activation circuitry, as described later in this disclosure. This class of concepts are similar to the previous class of electrically initiated inertial igniter embodiments shown in FIG. 1, with the main difference being that the electrical energy required to heat the wire electrode probe to initiate ignition of the pyrotechnic paper is provided mainly by a reserve micro-power battery, preferably fabricated on the aforementioned logic-based detection and switching circuitry chip, thereby significantly reducing the amount of power that the at least one piezoelectric element has to produce. In addition, since the energy density of the reserve battery is generally significantly higher than that of the piezoelectric elements, the resulting electrically initiated inertial battery is also expected to be smaller.

In this class of electrically initiated inertial igniter embodiments, essentially the same event detection, safety and ignition initiation electronics and logic circuitry described for the aforementioned first class of electrically initiated inertial igniters shown in FIG. 1 is employed with the exception that the power to initiate the ignition of the pyrotechnics comes mostly from the micro-power battery rather than the piezoelectric generator. As a result, more piezoelectric generated power is available to power the electronics and logic circuitry; thereby it is possible to add more safety features and even active elements to the circuitry. More sophisticated detection schemes and more layers of safety may also become possible to add to the igniter electronics.

One type of reserve micro-power battery that is suitable for the present application is micro-batteries in which the electrode assembly is kept dry and away from the active liquid electrolyte by means of a nano-structured and superhydrophobic membrane from mPhase Technologies, Inc., 150 Clove Road 11th Floor, Little Falls, N.J. 07424. Then using a phenomenon called electro-wetting the electrolyte can be triggered by a voltage pulse to flow through the membrane and initiate the electrochemical energy generation. Such batteries have been fabricated with different chemistries.

In this class of electrically initiated inertial igniter embodiments, when the aforementioned event detection electronics circuitry and logic (such as those shown in FIGS. 2 and 4-6) detects the all-fire event, the circuit would then switch the required voltage to trigger and activate the reserve micro-power cell. In this concept, the piezoelectric element must only provide enough energy to the capacitor so that the required voltage is generated in the capacitor for activation of the reserve battery. For this purpose and for the aforementioned reserve micro-power cell, the capacitor may have to provide a brief voltage pulse of approximately 50 milliseconds duration of between 30-70 volts. It is important to note that the triggering activation voltages required for electrowetting technique to activate the reserve power cell requires negligible current from the storage capacitor.

The expected size and volume of the class of electrically initiated inertial igniter embodiments shown in the block diagram of FIG. 7 is expected to be less than those for the embodiments constructed based on the block diagram of FIG. 1. This is expected to be the case since a significantly smaller piezoelectric element will be needed for the activation of the aforementioned reserve micro-power battery, which could be of the order of 1 $mm^2$ surface area and integrated onto the logic and switching circuitry. In addition, the capacitor used for triggering the reserve micro-power battery is expected to be significantly smaller than that of the class of igniters shown in the block diagram of FIG. 1. In addition, the power required to activate the reserve micro-power battery is minimal.

In an alternative embodiment shown in the block diagram of FIG. 7, an electrically initiated thermal reserve micro-battery is used instead of the aforementioned micro-batteries in which the electrode assembly is kept dry and away from the active liquid electrolyte by means of a nano-structured and super-hydrophobic membrane. The thermal micro-battery can be very small since it has to provide a very small amount of electrical energy which is quickly stored in the device power capacitor (e.g., the capacitor C1 in FIGS. 2, 4-6). In fact, since in general the thermal micro-battery is required to provide a very small amount of electrical energy (usually 5-10 mJ to a maximum of 100-200 mJ of electrical energy), the battery may be constructed with minimal or even no insulation, thereby allowing it to be constructed in even smaller packages.

The use of piezoelectric elements (preferably in stacked configuration) for energy harvesting in gun-fired munitions, mortars and the like is well known in the art, such as at Rastegar, J., Murray, R., Pereira, C., and Nguyen, H-L., "Novel Piezoelectric-Based Energy-Harvesting Power Sources for Gun-Fired Munitions," *SPIE 14th Annual International Symposium on Smart Structures and Materials* 6527-32 (2007); Rastegar, J., Murray, R., Pereira, C., and Nguyen, H-L., "Novel Impact-Based Peak-Energy Locking Piezoelectric Generators for Munitions," *SPIE 14th Annual International Symposium on Smart Structures and Materials* 6527-31 (2007); Rastegar, J., and Murray, R., "Novel Vibration-Based Electrical Energy Generators for Low and Variable Speed Turbo-Machinery," *SPIE 14th Annual International Symposium on Smart Structures and Materials* 6527-33 (2007). Rastegar, J., Pereira, C., and H-L.; Nguyen, "Piezoelectric-Based Power Sources for Harvesting Energy from Platforms with Low Frequency Vibration," *SPIE 13th Annual International Symposium on Smart Structures and Materials* 6171-1 (2006) and U.S. Patent Application Publication No. 2008/0129151 filed on Dec. 3, 2007. In such energy harvesting power sources that use piezoelectric elements, the protection of the piezoelectric element from the harsh firing environment is essential and such methods are fully described in the above provided references.

Figure 8:
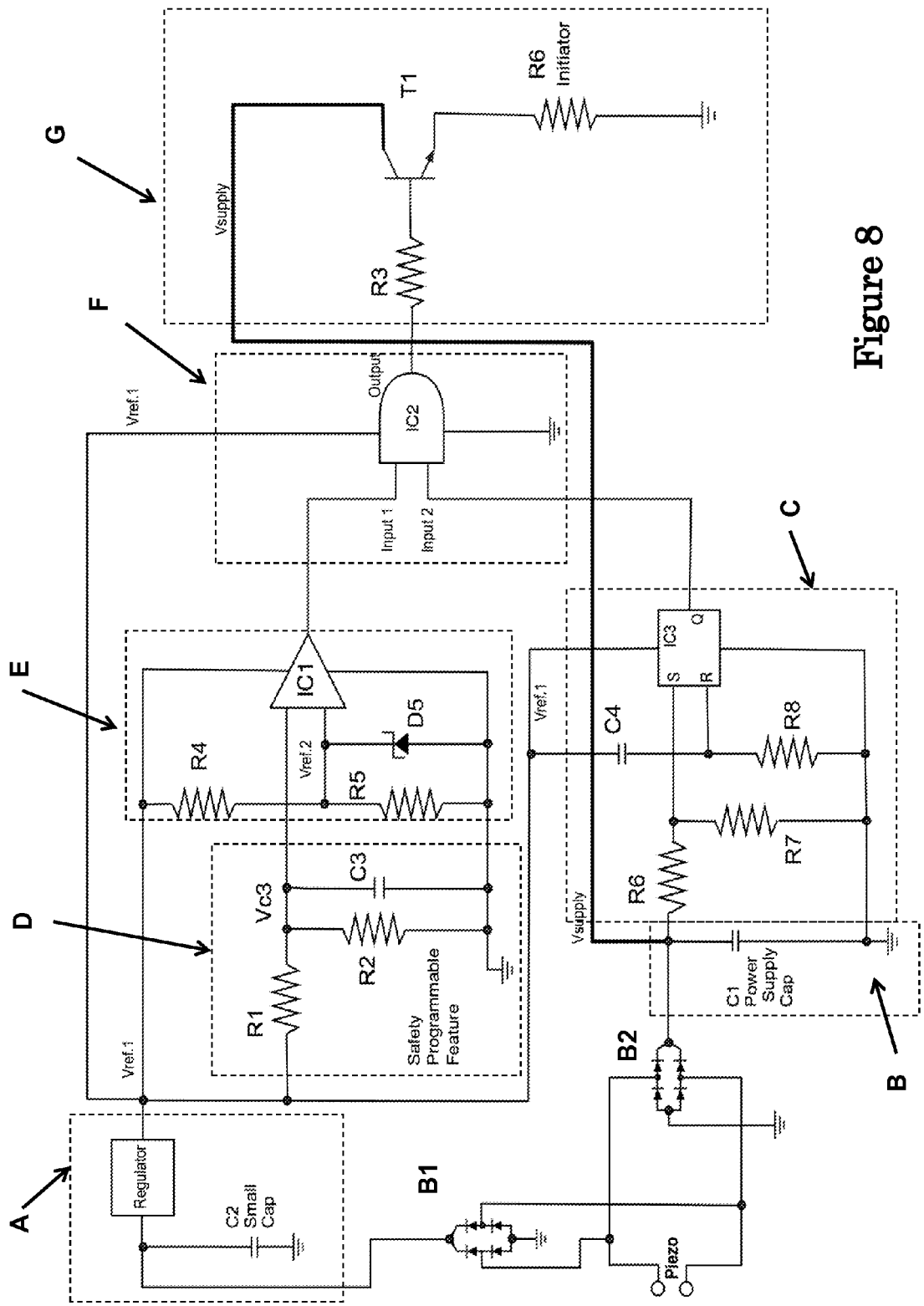
FIG. 8 illustrates an alternative piezoelectric powered programmable event detection and logic circuitry for differentiating all no-fire events from all-fire events and to initiate igniter following all-fire event detection.

Another alternative embodiment is shown in the diagram of FIG. 8. In this programmable inertial ignition device embodiment diagram, the circuitry design is divided into functional sections which when interconnected provide reliable methods to prevent unintentional and accidental initiation to achieve the prescribed no-fire and all-fire condition. In the diagram of FIG. 8, each of the aforementioned functional sections (shown in FIG. 8 with dashed rectangles and indicated by capital letters A-G) are described separately as well as how they are interconnected and function as a programmable inertial ignition device. In this embodiment of the programmable inertial ignition device, piezoelectric generators are also used to harvest energy to power the device electronics and logics circuitry as well as power the electrical initiator of the device.

Similar to the embodiments of FIGS. 2 and 4-6, at least one piezoelectric-based generator (indicated as piezo in the diagrams of FIGS. 2, 4-6 as well as 8) is provided. The generated electrical charges can be rectified by the diodes bridges B1 and B2 (only one diode bridge can be used and are shown in the above diagrams for ease of illustration only).

Section A:

When the piezoelectric generator is subjected to shock loading such as experienced by setback and/or acceleration and/or is subjected to mechanical vibration, its output is rectified by the diode bridge B1 and a small amount of the generated electrical energy is used to begin to charge a small capacitor [C2]. The voltage across C2 is regulated to a fixed reference voltage [Vref.1]. The regulated voltage [Vref.1] provides power to logic circuits [IC1, IC2, IC3].

Sections B, C, F:

The electrical output of the piezoelectric generator also feeds the power supply capacitor C1 (Section B) from diode bridge B2, which will charge much slower than capacitor C2 due to its significantly larger size. The voltage across C1 will not power the initiator until it reaches a controlled value, as follows: IC3 monitors the voltage across C1 by means of resistors R6 and R7 (part of Section C). When the voltage at the (S) input of IC3 reaches approximately 0.7 Vref.1, latch device IC3 output will switch to logic 1. The output of IC3 will provide a logic 1 condition at input 2 of IC2 (Section F). IC3 will always be initialized to a logic zero output when Vref.1 first comes on. The initialization is achieved by a very small burst of electrical energy from Vref.1 being fed to the reset (R) input of IC3 through capacitor C4 and resistor R8. Capacitor C4 charges very quickly and its impedance becomes infinite at full charge, therefore the voltage at the reset (R) pin of IC3 becomes zero in a few micro-seconds. The duration of the reset (R) pulse is directly controlled by C4*R8 (part of Section C).

Sections D, E, F:

The safety programmable feature (Section D) functions as previously described for the embodiments of FIGS. 2 and 4-6. In short, it uses the electrical energy generated by the piezoelectric generator to charge the capacitor C3. The capacitor C3 charges at a rate that is controlled by R1*C3. Resistor R2 leaks some of the charge built across C3, so that the voltage across C3 does not build up unless a sustained and high amount of electrical energy is generated by the piezoelectric generator, i.e., a large enough force is applied to the piezoelectric element long enough, as would be the case during the launch acceleration of munitions (corresponding to the all-fire condition). If the voltage across C3 (Vc3) reaches the same value or higher value than the voltage across R5 and D5 (Vref.2), then op-amp IC1 output will reach a logic 1. The diode D5 is a clamping and transient suppression diode. The output of IC1 is directly connected to the input 1 of IC2.

Sections F, G:

When both input 1 and input 2 conditions are met (Section F), the output of logic circuit IC2 will provide electrical energy to drive transistor T1 into saturation and therefore transistor T1 will operate as a switch thereby connecting the supply voltage across C1 (V supply) to the initiation device (indicated as resistor R6). Note that switch T1 will not connect "V supply" until it reaches a value of approximately 0.7Vref.1.

Figure 9:
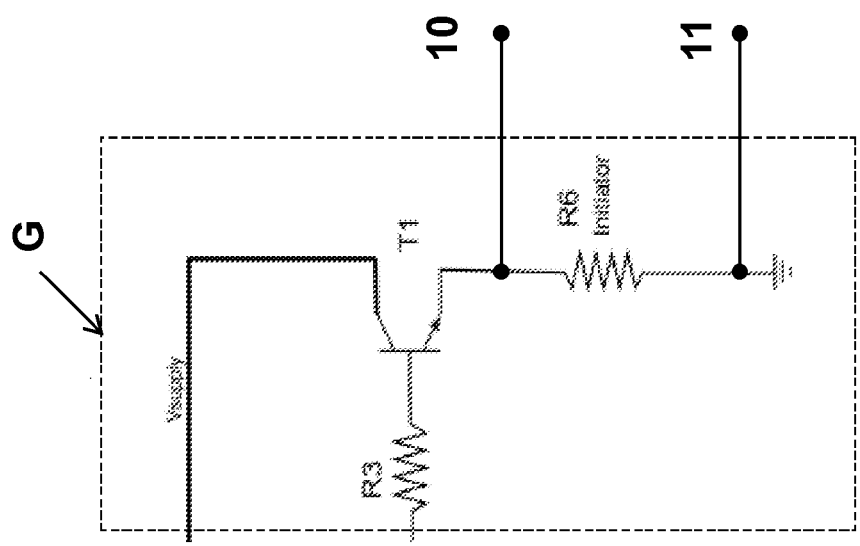
FIG. 9 illustrates the initiator circuitry portion of the piezoelectric element based class of programmable electrically initiated inertial igniter embodiments as modified to provide for detection of the thermal battery or the like activation status.

In the embodiments, the initiator (e.g., indicated as resistor R6 in the embodiment of FIG. 8) was shown to be used. It is noted that during the initiation process, the resistor R6 is heated up to initiate the pyrotechnic material that surrounds it. During this process, the resistor R6 filament or the like is burned, and thereby very low resistance (usually in the order of a few Ohms) measured of the resistor R6 is significantly increased (usually by orders of magnitude) depending on the pyrotechnic material used in the initiator. This change in the resistance of the initiator filament is readily detectable and can be used to determine if the initiator has been activated. For the example of the embodiment of FIG. 8, the resistance of the resistor R6 is readily measured between the terminals 10 and 11 as shown in the schematic of Section G of the FIG. 8 circuitry that is redrawn in FIG. 9.

It will be appreciated by those skilled in the art that in certain situations, for example following certain accidents such as dropping of munitions or when subjected to electrostatic discharge or the like or for health monitoring purposes, it is highly desirable for the user to be able to determine if the thermal battery has been activated or not without the need to disassemble the munitions and perform testing such as using x-rays to determine the activation state of the thermal battery. The above embodiment allows the user to interrogate the activation state of the thermal battery to determine if it has been already activated by measuring the resistance level of the initiator. It is noted that even if the thermal battery has been accidentally initiated by means other than the activation of the initiator (resistor R6 in FIGS. 8 and 9), upon activation of the thermal battery pyrotechnic materials, the initiator resistor would still be burned and the state of the thermal battery activation can still be determined by the measured changes in the initiator electrical resistance.

Figure 10:
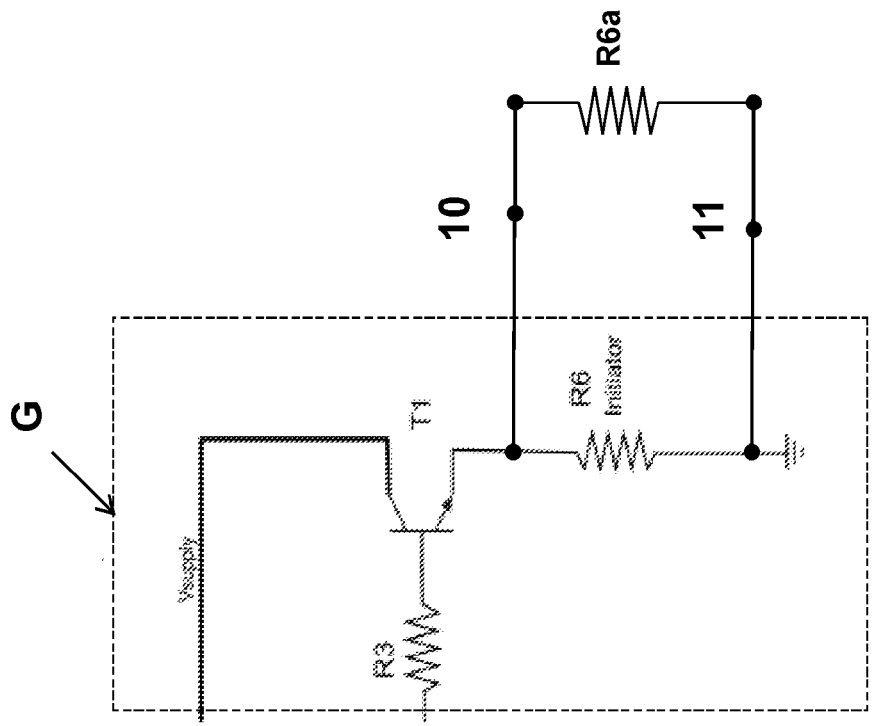
FIG. 10 illustrates the initiator circuitry portion of the piezoelectric element based class of programmable electrically initiated inertial igniter embodiments using at least two initiators to increase thermal battery or the like activation reliability.

It is a common practice in thermal batteries to use a single initiator for thermal battery activation, as was also described in the aforementioned embodiments. However, in certain applications when very high initiation reliability is desired, two or more initiators (e.g., similar to the initiator R6 in FIGS. 8 and 9) may be employed. For example, at least one additional initiator R6a may be provided in parallel with the initiator R6 as shown in the modified schematic of Section G of the circuitry of FIG. 8 as illustrated in the schematic of FIG. 10. With the addition of the least one additional initiator R6a, FIG. 10, by measuring the electrical resistance between the terminals 10 and 11, it is readily determined if at least one of the initiator resistors R6 or R6a has burned, i.e., its electrical resistance has been significantly increased, which indicates if the thermal battery has been activated.

Figure 11:
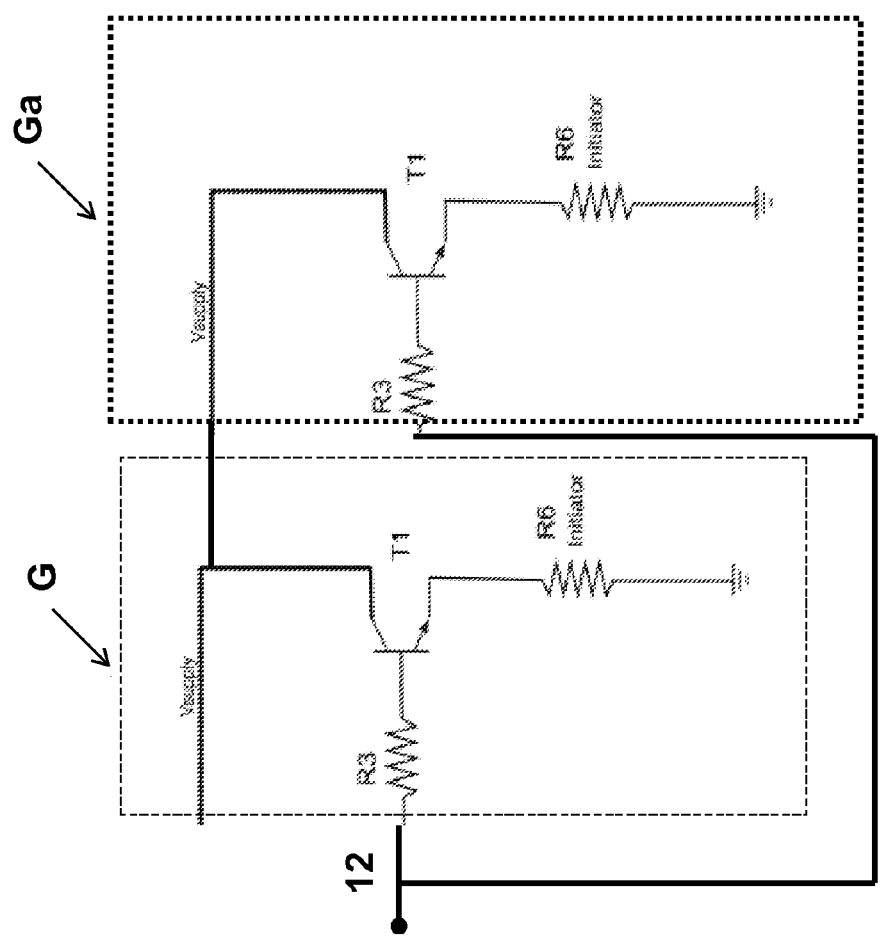
FIG. 11 illustrates the initiator circuitry portion of the piezoelectric element based class of programmable electrically initiated inertial igniter embodiments using at least two initiators with independent circuitry to further increase thermal battery or the like activation reliability.

When more than one initiator is being used to increase thermal battery activation reliability, it is highly desirable to provide the additional initiators with independent circuitry, and when possible, independent sources of power and safety and logics circuitry as described for the embodiments of FIGS. 2, 4-6 and 8. When it is not possible to provide such totally independent power source and circuitry, the at least one additional independent initiator circuitry needs to be powered by the same device power supply capacitor (e.g., the power supply cap C1 of Section B in FIG. 8). For the embodiment of FIG. 8 and with one additional independent initiator circuitry, the resulting Section G circuitry can be modified to that of FIG. 11. In FIG. 11, the aforementioned one additional independent initiator circuitry is indicated as Section Ga, and is shown to be constructed with identical components R3, T1 and initiator R6, but could obviously be constructed with any other appropriate components and circuitry, and is connected to the circuitry of the embodiment of FIG. 8 and its Section G as shown in FIG. 11.

It will be appreciated by those skilled in the art that for the latter embodiment shown in the schematic of FIG. 11, the more than one parallel initiator R6 (in the Section G) and R6a (in the at least one Section Ga) may be employed, such as the one shown in FIG. 10.

It is also appreciated by those skilled in the art that the provision of more than one initiator in a thermal battery has many advantages, including the following:
1. By providing more than one initiator, particularly if it has independent circuitry and when possible a totally independent initiation unit with its own power source and safety and initiation circuitry, the thermal batter activation reliability is significantly increased.
2. With more than one initiator, the initiators can be distributed in the thermal battery to ignite the thermal battery pyrotechnic materials at more than one location. This capability provides the means of achieving several objectives. Firstly, since the thermal battery rise time (the time that it takes for the battery to become functional following initial initiator activation) is dependent on the time that it takes for the thermal battery pyrotechnic (heat generating components) to burn and melt the solid electrolyte, by igniting the thermal battery pyrotechnic materials at more than one location, the total time that it takes for the pyrotechnic material to be burned is significantly reduced. As a result, the thermal battery becomes fully functional faster, i.e., the thermal battery rise time is significantly reduced. Fast rise time is a highly desirable characteristic in certain munitions, e.g., when the thermal battery power is required a very short time following firing. Secondly, by distributing multiple initiators in the thermal battery, a more uniform pattern of pyrotechnic material burn is achieved in the thermal battery and, thereby avoiding non-uniform heating and later cooling of the solid electrolyte, thereby achieving a better thermal battery performance.

In the aforementioned embodiments, active material based elements such as piezoelectric elements (FIGS. 1-2 and 4-8) can be used to generate electrical energy by harvesting electrical energy from the firing acceleration. It is, however, appreciated by those skilled in the art that other types of electrical generators such as coil and permanent magnet type generators may also be used for this purpose. Such coil and permanent magnet type electrical generators may be constructed to undergo linear or rotary or a combined linear and rotary motion, including a vibratory type of linear and rotary motions. In either case, the linear or rotary motion, including of vibratory type, are caused or initiated by the firing event of the munitions in which the thermal battery or the like equipped with such devices are mounted. As an example, coil and permanent magnet type generators that are designed to occupy relatively small volumes and generate electrical energy as a result of firing setback and/or set-forward accelerations and some even as a result of flight vibration and oscillatory motions are provided below.

Figure 12:
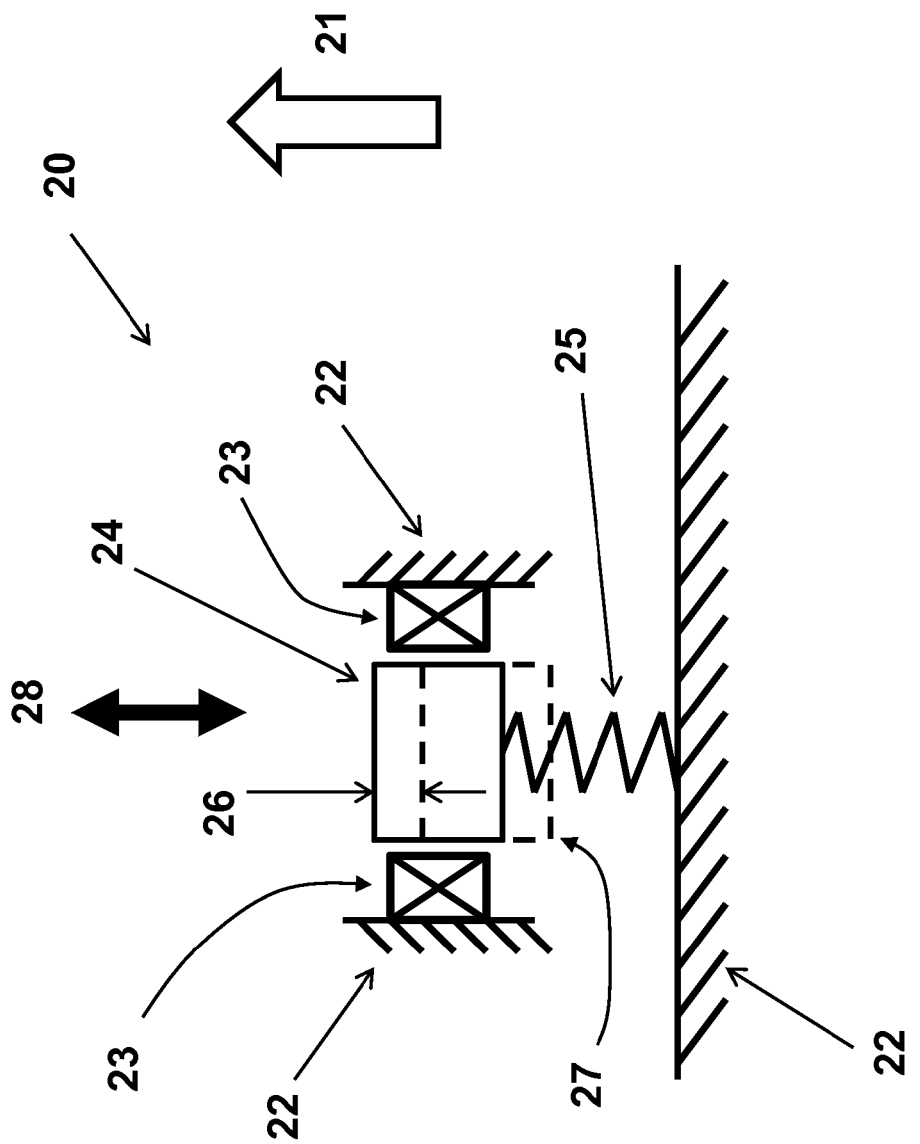
FIG. 12 illustrates a permanent magnet and coil type electrical power generator alternative to the piezoelectric element based power source used in the class of programmable electrically initiated inertial igniter embodiments of FIGS. 1-2 and 4-8.

In one embodiment, a magnet and coil generator 20 that forms a vibrating mass-spring system shown in the schematic of FIG. 12 is used to generate electrical energy as a result of firing acceleration in the direction of the arrow 21. The magnet and coil generator 20 is attached to the structure 22 of the device (generally the structure of the initiator), and consists of a coil 23 and magnet 24 elements, with the magnet 24 element (constructed with at least one permanent magnet) is preferably used to function as a mass element that together with the spring element 25 form a vibrating mass-spring unit, that is attached to the structure 22 of the initiator device. Then as the munitions using any one of the initiator embodiments shown in FIGS. 1-2 and 4-8 is fired, the firing setback acceleration acts on the mass (magnet portion) 24 of the generator 20, causing the spring element 25 to be deflected a distance indicated by 26, bringing the mass to the position 27, as indicated by dashed lines in FIG. 12. As the munition accelerates, such as after the munition exits the barrel, the mass-spring unit (elements 25 and 26, respectively) will begin to vibrate up and down in the direction shown by the arrows 28, and the generator will generate electrical energy as is well known in the art. It is noted that in general the firing set-forward acceleration and vibration of the munitions during the flight would also cause vibration of the generator mass-spring unit, thereby cause the generator 20 to generate more electrical energy. The spring element 25 is preferably made with at least 3 helical strands to minimize the tendency of the mass-spring element to displace laterally or bend to the side during longitudinal displacement and vibration in the direction of the arrow 21.

It will be appreciated by those skilled in the art that since electrical energy is generated in the coils 23, the vibrating component of such magnet and coil generators can be the permanent magnet(s) 24 of the magnet and coil generator 20. As a result, the generator output wires are fixed to the structure 22 of the device and the chances of them breaking is minimized.

In another embodiment, the spring element 25 is preloaded and the permanent magnet(s) 24 (mass element) of the mass-spring unit of the magnet and coil generator 20 is locked in its displaced position 27 shown by dashed lines in FIG. 12 by at least one locking element that is provided to lock the spring 25 in its compressed (preloaded) configuration. Then during firing of the projectile, the munitions structure to which the present device magnet and coil generator 20 is rigidly attached is accelerated in the direction of the arrow 21, causing the aforementioned at least one locking element to release permanent magnet(s) 24 (mass element) of the mass-spring unit of the magnet and coil generator 20. Once the permanent magnet(s) 24 (mass element) of the mass-spring unit of the magnet and coil generator 20 is released, the mechanical potential energy stored in the spring 25, i.e., the mechanical potential energy stored in the "mechanical reserve power sources" 20, is released. The released mechanical potential energy will then cause the mass-spring unit) to vibrate, thereby causing the magnet and coil generator 20 to generate electrical energy. Such locking elements for locking preloaded mass-spring units (here, for the permanent magnet(s) 24, i.e., the mass element, of the mass-spring unit of the magnet and coil generator 20) that lock preloaded linearly or rotationally or flexural vibrating units and that are released due to axial acceleration (setback or set-forward acceleration in munitions), or rotational (spin) accelerations or spin rate (due to centrifugal force) are fully described in the U.S. Pat. No. 8,183,746, the entire contents of which is incorporated herein by reference.

Figure 13:
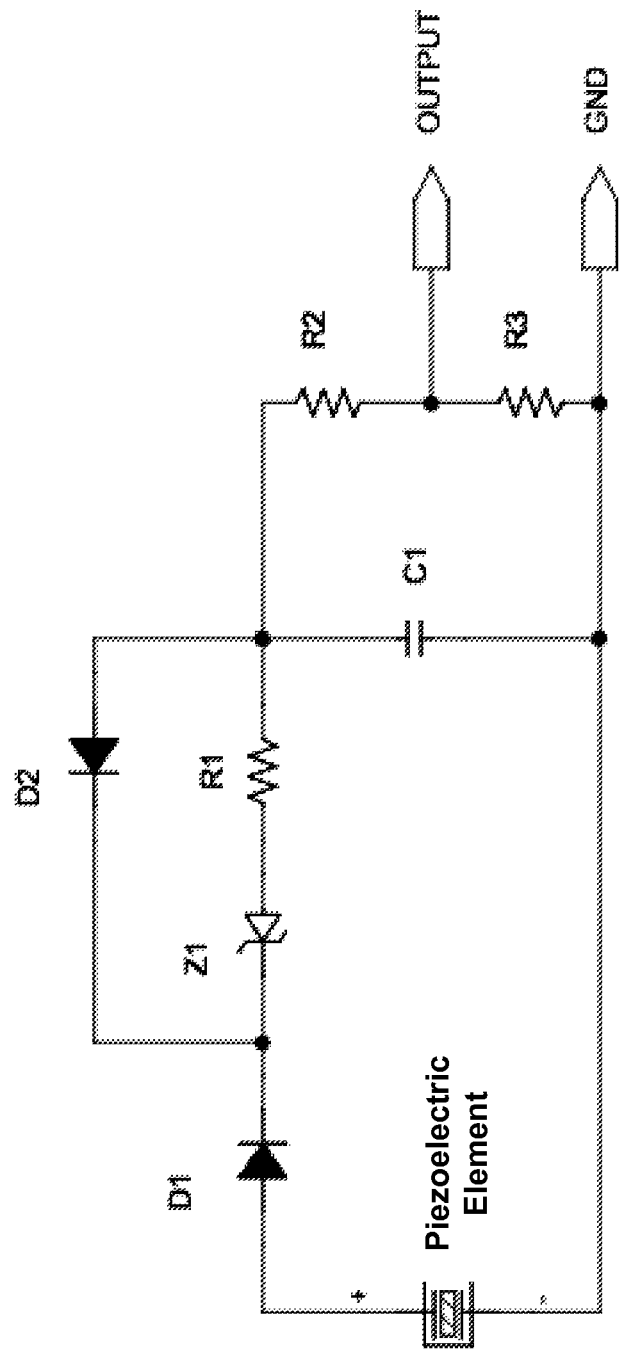
FIG. 13 illustrates an alternative embodiment of the programmable safety and all-fire detection circuitry.

In another alternative embodiment, the aforementioned safety and all-fire detection circuitry (such as the "safety programmable feature" of FIG. 8 and marked "D") is provided with additional beneficial features herein being described. In this embodiment, the general circuitry of the safety and all-fire detection is as shown in FIG. 13. The circuitry is considered to be passive since it does not require any external source of power or batteries or other similar sources of chemical or externally charged power sources for its operation. In a manner similar to those described for the previous safety and all-fire detection circuitry, the firing setback or other shock loading and/or vibrations of the device in which the present circuitry is used would induce charges in the piezoelectric (preferably stack) element. The present circuitry is designed to differentiate firing setback induced shock (high-G accelerations with relatively long duration) from all other no-fire accelerations such as high-G but short duration pulse(s), relatively low peak G but long term vibration loading such as experienced during transportation and the like.

In the safety and all-fire detection circuitry of FIG. 13, electrical energy (charge) is provided by at least one piezoelectric (preferably stack) element. All-fire setback condition is detected by the voltage level of the capacitor C1 while the circuitry prevents the charging of the capacitor C1 to the prescribed voltage level if the generated piezoelectric charges are due to the aforementioned no-fire conditions as described below.

In the safety and all-fire detection circuitry embodiment of FIG. 13, the diode D1 (preferably a Schottky or a similar diode with a low forward voltage drop and a very fast switching action is used as a rectifier. The indicated feature of the diode D1 reduces energy loss in the circuitry. The indicated diode D1 also has a high backward leakage, which is used as a safety feature in the present embodiment for discharging collected charges in the capacitor C1 when the voltage of the piezoelectric element drops below the prescribed all-fire voltage level.

After rectified, the current due to the charges generated by the piezoelectric element passes through diode Z1 (preferably a Zener or a similar diode) and resistor R1 to charge the capacitor C1 and also pass through resistors R2 and R3 to the ground. During this time, the diode D2 is under reverse bias, thereby passing a very small amount of current. The voltage on the capacitor C1 indicates the amount of energy generated by the piezoelectric element due to its (shock or vibration) loading, less the amount of energy drainage through the resistors R2 and R3 and the losses in the diode Z1 and smaller amounts in the remaining circuit elements. The resistors R2 and R3 also act as a programmable divider that can be used to adjust the output voltage level corresponding to the all-fire condition as demanded by the device/circuitry at the circuitry output shown in FIG. 13. It is also noted that the output and ground can also be used as a differential output.

When a device using the circuitry shown in FIG. 13 is subjected to a relatively short duration shock loading such as due to accidental dropping, the piezoelectric element would generate relatively high voltage pulses with very short duration. The generated voltages may even be higher than the voltage level that are generated as the device is subjected to the prescribed all-fire setback acceleration, but the duration of such pulses is significantly shorter than those of the all-fire setback acceleration pulse. For example, an all-fire acceleration may be around 900 G with 10 msec of duration while an accidental drop may cause a shock loading of up to 2,000 G but for a very short duration of less than 0.5 msec. In the present circuitry embodiment, the capacitor C1 and the resistor R1 are sized such that the resulting charging time constant (R1C0 for the capacitor C1 is significantly longer than such "high voltage and short duration" pulses, thereby ensuring that the capacitor C1 is not charged to the aforementioned "all-fire voltage level" due to any no-fire shock loading event. In addition, to ensure that the charges due to several such "high voltage and short duration" pulses do not accumulate in the capacitor C1 and provide a false "all-fire voltage level" indication, the diode D2 is provided to discharge all accumulated charges in the capacitor C1 once the piezoelectric voltage drops below the voltage level on C1.

In certain application, however, when the piezoelectric voltage drops, the amount of discharge through the diode D2 is desired to be limited to a drop of the capacitor C1 voltage to certain threshold. The voltage threshold may be desired, for example, for allowing the voltage at the circuitry OUTPUT not to drop below certain limit. As an example and without intending to indicate any limitation on the use of other components and circuitry to perform the same functionality, such a goal can be readily achieved by the addition of a Zener diode Z2 between the diodes D1 and D2 as shown in the alternative "safety and all-fire detection circuitry" embodiment of FIG. 19. As a result, piezoelectric voltage drops, the charges accumulated in the capacitor C1 is discharged through the diode D2, but only to the breakdown voltage level of the Zener diode Z2 instead of dropping to essentially the voltage level of the piezoelectric element.

Figure 19:
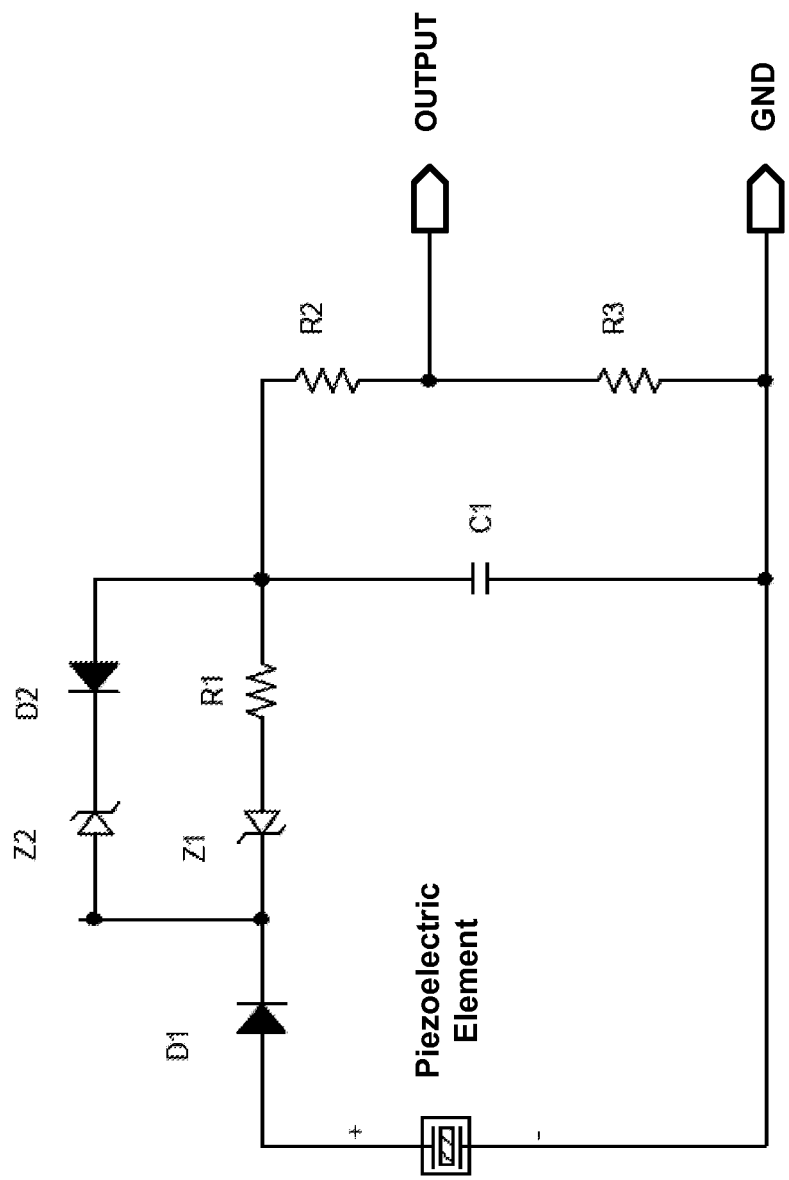
FIG. 19 illustrates an alternative embodiment of the programmable safety and all-fire detection circuitry of the embodiment of FIG. 13.
Figure 19A:
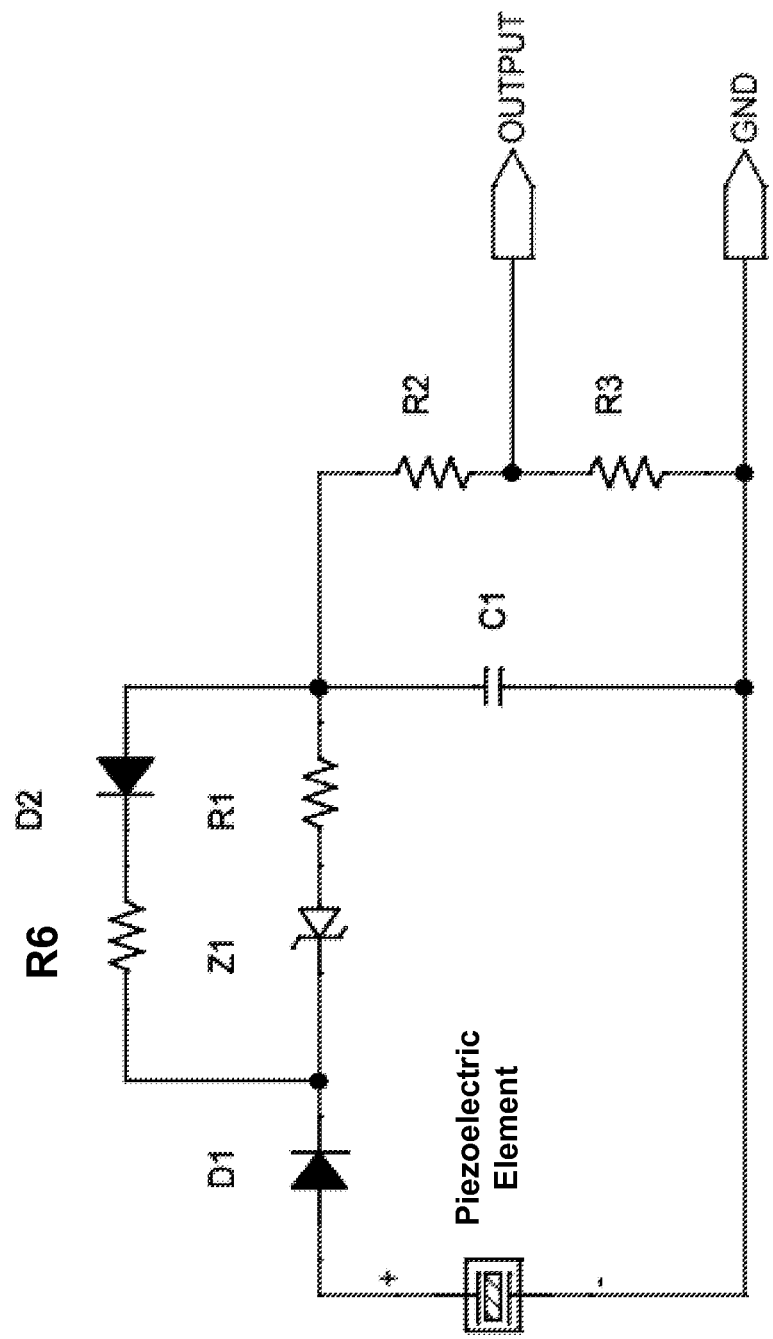
FIG. 19A illustrates an alternative embodiment of the programmable safety and all-fire detection circuitry of the embodiment of FIG. 19.

In addition, in both the circuits of FIGS. 13 and 19, when the diode D2 is under reverse bias, it passes a very small amount of current. If in certain applications the amount of this current is needed to be reduced, this can be readily accomplished by the addition of the serial resistor R6 as shown in the schematic of FIG. 19A. Then in the resulting circuit, when the diode D2 is under forward bias, the resistor R6 would control the time that it would take for the charges collected on the capacitor C1 to be discharged back to the piezoelectric element.

It is noted that leaking through resistors R2 and R3 is also used to lengthen the amount of time that is needed for the piezoelectric element to charge the capacitor C1. This capability provides a simple tool to readily adjust ("program") the device to the desired "all-fire" condition. The leakage through resistors R2 and R3 would also provide additional means of ensuring that the aforementioned high voltage and short duration pulses do not accumulate charge in the capacitor C1 to trigger a false all-fire detection signal.

It is also noted that vibration loading (usually with peak G loadings that are usually significantly lower than those of accidental drops or the like) for long periods of time such as those experienced during transportation or other similar conditions, even if they are accompanied with aforementioned higher G but short duration shock loading pulses are similarly rejected by the Zener diode Z1 and the leaking resistors R2 and R3. The breakdown voltage of the Zener diode Z1 is generally selected depending on the selected all-fire indicating voltage of the capacitor C1.

The piezoelectric element powered safety and all-fire detection circuitry shown in FIGS. 13, 19 and 19A provide a voltage at the indicated output that can be monitored by the user device/circuitry to detect no-fire condition based on the prescribed ("programmed") all-fire setback acceleration condition. In the following, the method of using the safety and all-fire detection circuitry embodiment of FIG. 13 or FIG. 19 or 19A to design passive initiators for igniting pyrotechnic material or the like is described. Examples of other applications for munitions all-fire condition detection and other commercial and industrial applications in which a prescribed shock or vibration loading is to be safely detected are described later in this disclosure.

A method of using the safety and all-fire detection circuitry embodiment of FIG. 13 (or similarly the safety and all-fire detection circuitry embodiment of FIG. 19 or 19A) to design passive initiators for pyrotechnic material or the like is herein described and examples of its implementation are provided. The safety and all-fire detection circuitry of the embodiment of FIG. 13 is redrawn in FIG. 14. In the present method, the circuit output is connected to the indicated "output voltage threshold detection and switching element", which is designed to detect when the output voltage threshold corresponding to the prescribed all-fire condition has been reached. When the all-fire voltage threshold is detected, the "output voltage threshold detection and switching element" would then close the indicated circuit and allow direct flow of current from the piezoelectric element through the indicated "initiator bridge wire" to the ground. The initiator bridge wires currently used are very low resistance (commonly around 1-3 Ohm) bridge wires that are heated by the passing current, which would then usually ignite certain (usually primary) pyrotechnic material. Initiator bridge wires of different types such as those made out of ultra-thin wires or wires printed/deposited/etched on certain substrate or semi-conductor type such as those fabricated using semi-conductor manufacturing processes are commonly used in electrical initiators and could be used in the present embodiment.

The "output voltage threshold detection and switching element" may be designed in a number of ways and with and without external power. In the munitions applications, however, one of the main objectives is safety, i.e., total or nearly total elimination of the chances that initiation could occur in the absence of all-fire detection. The other objectives in munitions application include passive circuitry, i.e., the initiator circuitry not requiring external power; and miniaturization, which requires very low power circuitry that can be powered with very small piezoelectric elements. The following embodiments are examples of passive electrical initiators for pyrotechnic material or the like constructed with the safety and all-fire detection circuitry embodiment of FIG. 13.

The method of using the safety and all-fire detection circuitry embodiment of FIG. 13 to design passive initiators for pyrotechnic material or the like is herein described and examples of its implementation are provided. The safety and all-fire detection circuitry of the embodiment of FIG. 13 is redrawn in FIG. 14. In the present method, the circuit output is connected to the indicated "output voltage threshold detection and switching element", which is designed to detect when the output voltage threshold corresponding to the prescribed all-fire condition has been reached. When the all-fire voltage threshold is detected, the "output voltage threshold detection and switching element" would then close the indicated circuit and allow direct flow of current from the piezoelectric element through the indicated "initiator bridge wire" to the ground. The initiator bridge wires currently used are very low resistance (commonly around 1-3 Ohm) bridge wires that are heated by the passing current, which would then usually ignite certain (usually primary) pyrotechnic material. Initiator bridge wires of different types such as those made out of ultra-thin wires or wires printed/deposited/etched on certain substrate or semi-conductor type those fabricated using semi-conductor manufacturing processes are commonly used in electrical initiators and could be used in the present embodiment.

Figure 14:
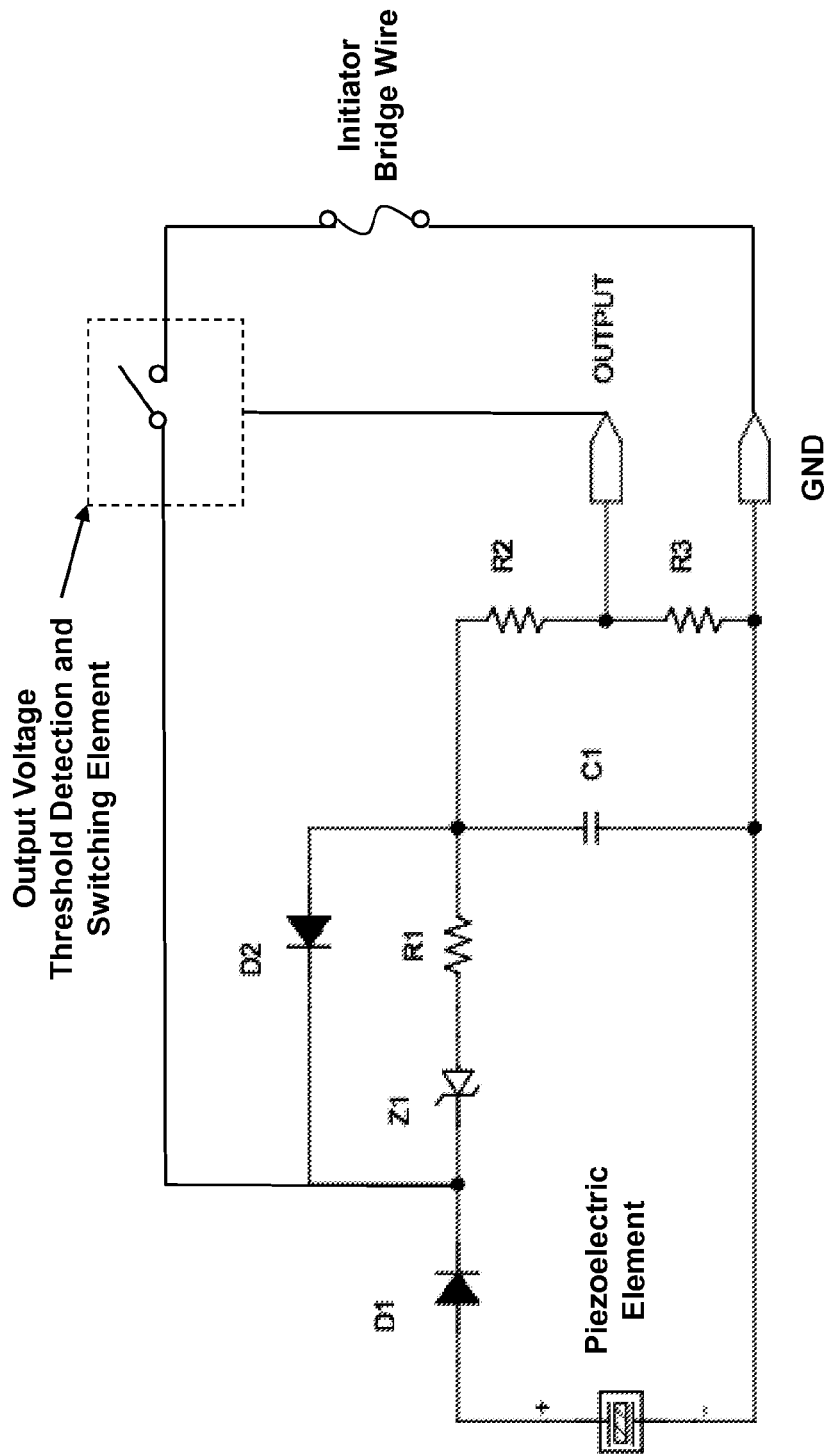

As was previously indicated, for most munitions and other similar applications, the "output voltage threshold detection and switching element" of the embodiment of FIG. 14 is to be designed with a very high level of safety, i.e., for total or nearly total elimination of the chances that initiation occurs in the absence of all-fire condition. Other important objectives in munitions and other similar applications include passive circuitry, i.e., the initiator circuitry not requiring external power; and miniaturization capability, which requires very low power circuitry that can be powered with very small piezoelectric elements. The following two basic embodiments are examples of the implementation of the embodiment of FIG. 14 for such passive electrical initiators for pyrotechnic material or the like that are constructed with the safety and all-fire detection circuitry embodiment of FIG. 13.

Figure 15:
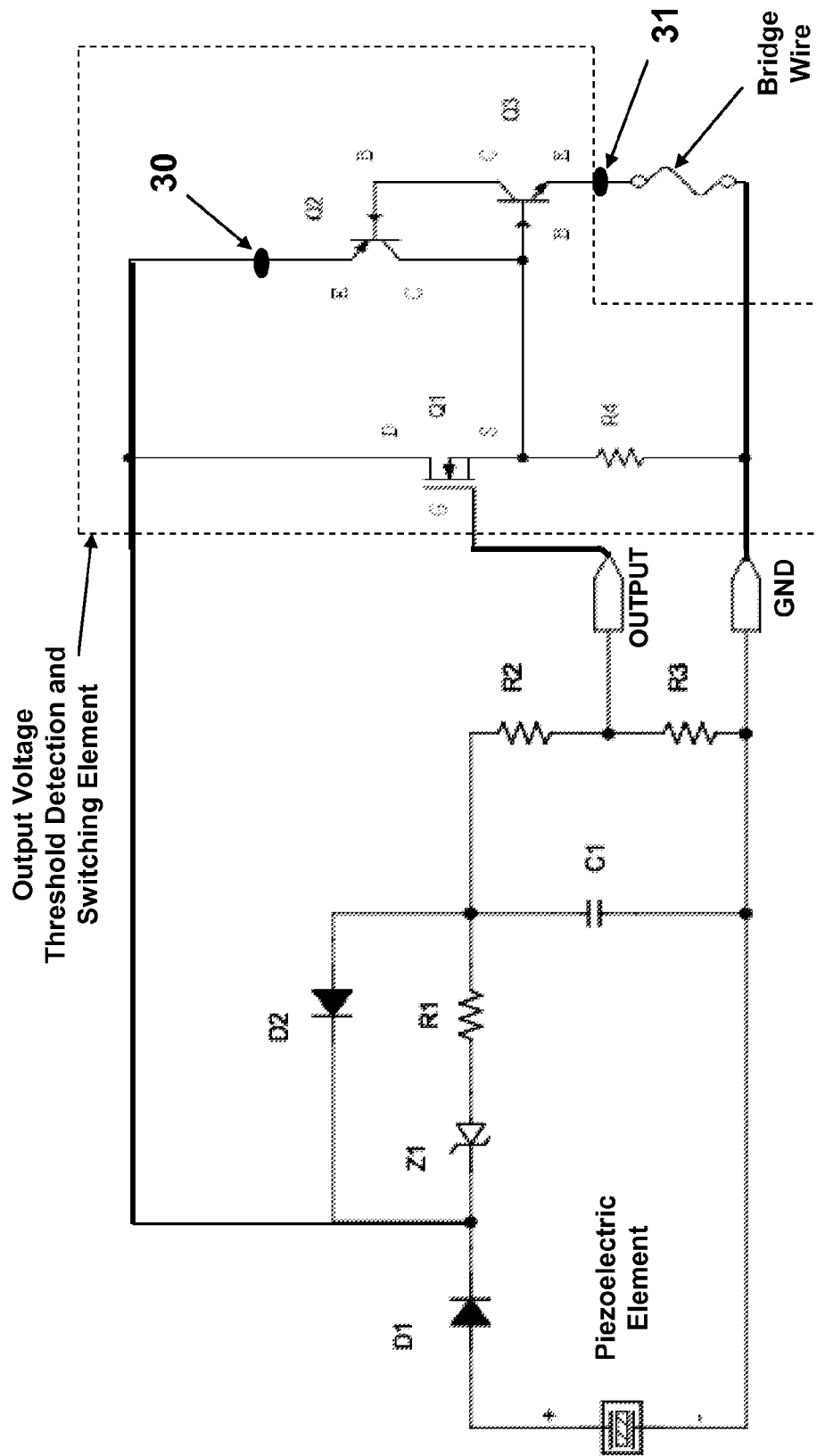
FIG. 15 illustrates the first embodiment of the passive initiators for pyrotechnic material or the like that is particularly suitable for munitions and other similar applications.

The first embodiment of the passive initiators for pyrotechnic material or the like with the above safety and low power characteristics which makes it particularly suitable for munitions and other similar initiator applications is shown in FIG. 15. In this embodiment, the safety and all-fire detection circuitry embodiment of FIG. 13 is provided with the "output voltage threshold detection and switching element" described for the embodiment of FIG. 14 designed with the circuitry shown inside the box with dashed lines. As can be seen in the "output voltage threshold detection and switching element" shown in FIG. 15, by appropriately selecting the component parameters of the circuitry, when the voltage at the OUTPUT of the safety and all-fire detection circuitry (FIGS. 13 and 15) reaches the prescribed all-fire threshold, the N-MOS (indicated as Q1 in FIG. 15) is switched on. During this switching-on process, the voltage on the resistor R4 increases and produces a current $I_{BE}$ on NPN transistor (indicated as Q3 in FIG. 15), in the direction of the arrow at B). The NPN transistor Q3 amplifies the current and introduces current $I_{BE}$ on PNP transistor Q2, while the PNP transistor Q2 amplifies the current and sends it back to the NPN transistor Q3. This positive feedback configuration of the two transistors Q2 and Q3 at certain saturates the two transistors, making them act as a "switch" that has been closed between the points 30 and 31 in the circuit of FIG. 15, thereby allowing the charges generated by the piezoelectric element to be discharged through the indicated "bridge wire" to the ground (GND). The very low resistance initiator bridge wire is then heated by the passing current, which would then ignite the provided (usually primary) pyrotechnic material.

It will be appreciated by those skilled in the art that when the transistors Q2 and Q3 saturate, the closed circuit between the points 30 and 31 stay closed since the positive feedback between the transistors Q2 and Q3 maintains the discharging current loop from the piezoelectric element through the bridge wire to the ground. This is an important feature of the current embodiment since the safety and the "safety and all-fire detection circuitry" portion (embodiment of FIG. 13) of the passive initiators embodiment of FIG. 15 is also powered by the device piezoelectric element, which means the detected all-fire signal voltage (at the indicated OUTPUT) will drop instantly as the transistors Q2 and Q3 saturate and the circuit ("switch") between the points 30 and 31 is closed and the piezoelectric element charges begin to discharge through the "bridge wire" to the ground. It will be appreciated by those skilled in the art that if the current to be passed through the "bridge wire" would have been routed through the indicated OUTPUT of the "safety and all-fire detection circuitry" portion of the device, the drop of the voltage at the OUTPUT point below the all-fire threshold level would have again suddenly blocked the current from reaching the "bridge wire" by reverting the "safety and all-fire detection circuitry" portion back to its no-fire state.

It will be appreciated by those skilled in the art that in the circuitry of FIG. 15, the resistance of the resistor R4 determines the input impedance of the bridge wire initiator circuitry. The resistor R4 resistance level is very important for reducing the sensitivity of the positive feedback against noise such as electromagenetic interference (EMI) and electromagnetic pulse (EMP) and the like. In a slightly modified circuitry, RC filters may be added between Q2 and Q3 to control the gain of positive feedback.

Figure 16:
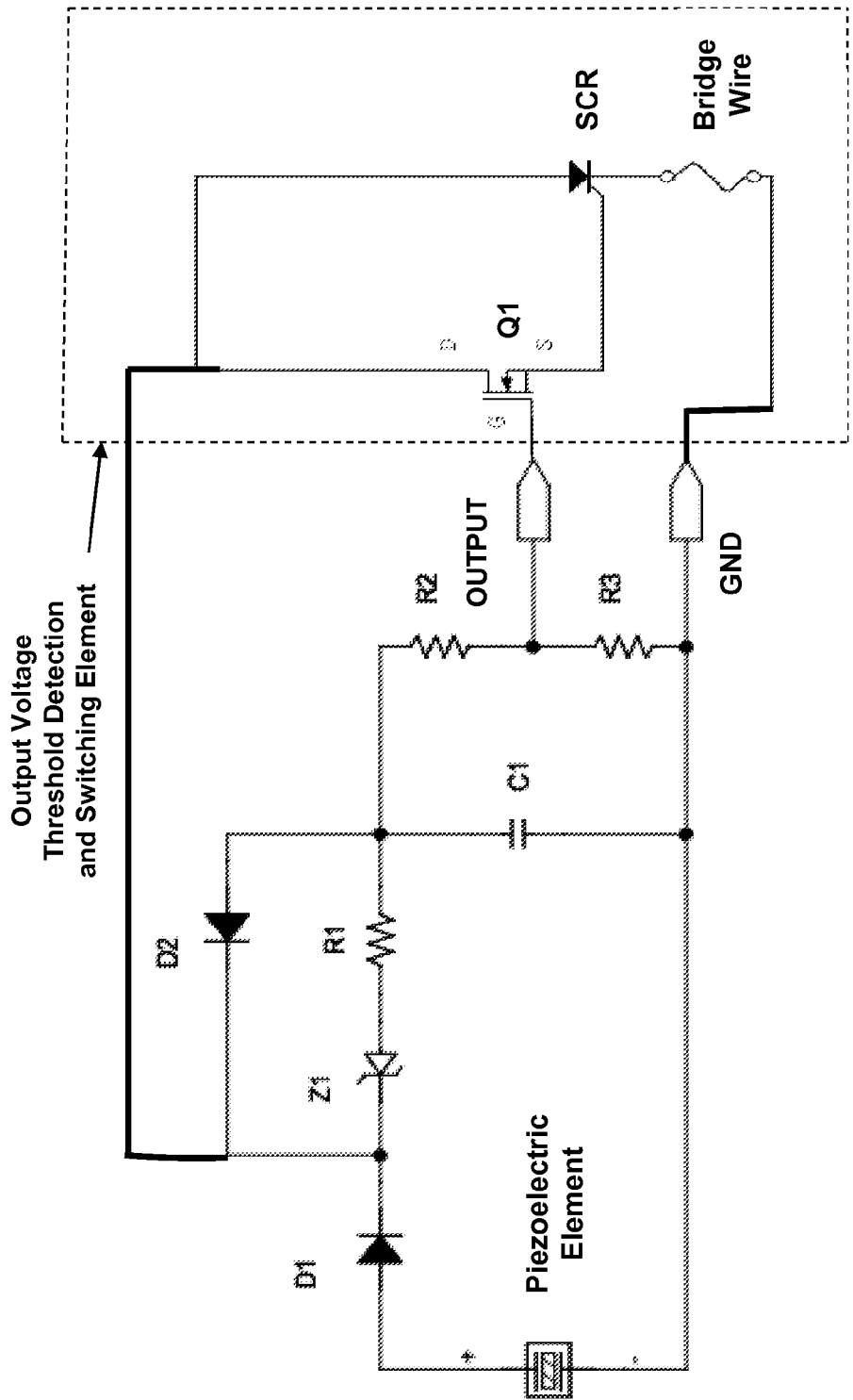
FIG. 16 illustrates the second embodiment of the passive initiators for pyrotechnic material or the like that is particularly suitable for munitions and other similar applications.

In a second embodiment of the passive initiators for pyrotechnic material or the like with the above safety and low power characteristics, when the noise due to sources such as electromagenetic interference (EMI) and electromagnetic pulse (EMP) and other internal and external sources is either very low or has been taken care of using appropriate shielding and filtering, then a Silicon Controlled Rectifier (SCR) may be used in place of the two transistors Q2 and Q3 in the embodiment of FIG. 14 as shown in the circuitry of FIG. 16. The SCR is a switch driven by gate current and would stay enabled while a current is being passed through it.

Then as was described for the embodiment of FIG. 15, by appropriately selecting the component parameters of the "output voltage threshold detection and switching element" portion of the circuitry shown in FIG. 16, when the voltage at the OUTPUT of the safety and all-fire detection circuitry (FIGS. 13 and 16) reaches the prescribed all-fire threshold, the N-MOS (indicated as Q1 in FIGS. 15 and 16) is switched on. When the N-MOS (Q1) is switched on, the SCR receives enough gate current $I_G$ and becomes a path to release all the charges from the piezoelectric element through the bridge wire to the ground (GND). The SCR will stay enabled until essentially all charges from the piezoelectric element are discharged and the aforementioned current $I_G$ is diminished. As a result, the flow of charges from the piezoelectric element through the bridge wire cannot be interrupted. The very low resistance initiator bridge wire is then heated by the passing current, which would then ignite the provided (usually primary) pyrotechnic material.

As was previously indicated, the piezoelectric element powered safety and all-fire detection circuitry shown in FIG. 13 provides a voltage at the indicated output that can be monitored by the user device/circuitry to detect no-fire condition based on the prescribed ("programmed') all-fire setback acceleration condition. The method of using the all-fire detection circuitry embodiment of FIG. 13 to design passive initiators for igniting pyrotechnic material or the like and a number of its practical implementation embodiments that are particularly suitable for munitions applications were disclosed above. In the following, the method of using the safety and all-fire detection circuitry embodiment of FIG. 13 to design "passive all-fire detection sensors" that would output a signal indicating that a prescribed all-fire condition or other similar events such as lower level impact or shock or sudden jerk or outset of vibration or the like has been detected is described. As previously indicated, these devices differentiate no-fire conditions such as accidental drops which can induce high G levels with short durations and transportation related shock and vibration loadings. The output signal could be of many different types, a few of which are described below, but other types appropriate for matching a user need, for example a flag, a switch and hold or the like, can generally be accommodated. The present devices are considered to be passive since they do not require external power sources for their operation. In the present devices, the sensory information as well as electrical energy to power the electronic circuitry is provided by an appropriately sized piezoelectric element(s).

The safety and all-fire detection circuitry shown in FIG. 13 may be used directly to provide a voltage output that can be monitored by the user device/circuitry to detect all-fire condition based on the prescribed all-fire setback acceleration and the selected circuit elements. It is noted that in general, the circuit elements are selected to minimize the power consumption and thereby minimize the size of the piezoelectric assembly. For the same reason, the voltage monitoring device is also desired to have very high impedance.

The safety and all-fire detection circuitry shown in FIG. 13 may also be used with other added logic circuitry and elements to provide the desired sensory information or sensory based actions such as the initiation described for the embodiments of FIGS. 14-16 and other purposes such as to provide a signal flag; provide multiple signal flags when different levels of firing setback accelerations are detected; or activate a switching device; or initiate the process of storing electrical energy in a storage device such as a capacitor; or numerous other applications.

Figure 17:
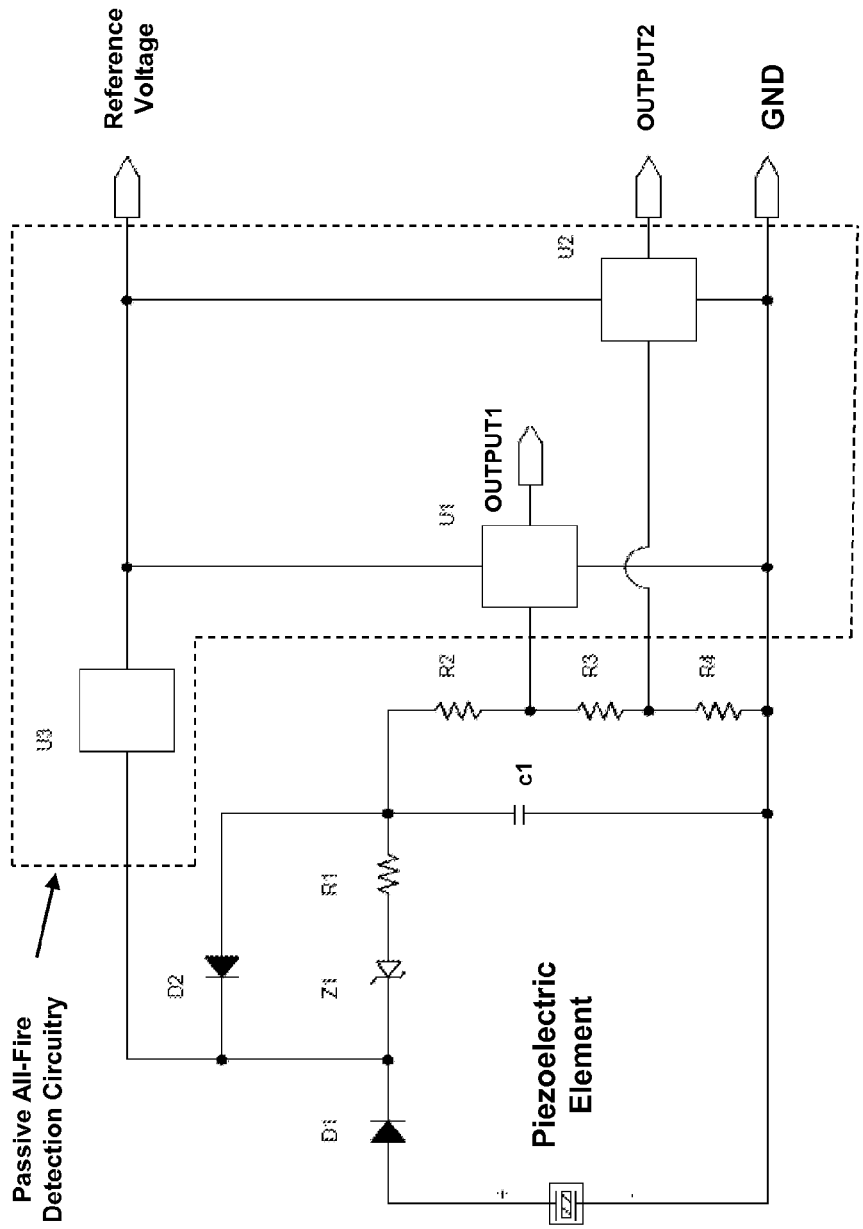
FIG. 17 illustrates the basic method for the design of a passive all-fire setback acceleration (shock) level detection sensor designed with the safety and all-fire detection circuitry of the embodiment of FIG. 13.

The method of designing the aforementioned "passive all-fire detection sensors" is shown in the schematic of FIG. 17. In FIG. 17, the "passive all-fire detection circuitry" portion of the circuitry enclosed by dashed lines. In this method, safety and all-fire detection circuitry shown in FIG. 13 is used provide logic signal flags when one or more firing setback acceleration (shock) levels are detected. In the schematic of FIG. 17, the circuitry provides logic signal flags for one or multiple firing setback acceleration levels (in the schematic of FIG. 17 for two firing setback or the like acceleration levels) that can be directly read by other devices through digital ports. In the circuitry of FIG. 17, this capability is provided by the addition of the indicated logic level comparators U1 and U2 to compare the outputs OUTPUT 1 and OUTPUT 2 of the safety and all-fire detection circuitry shown in FIG. 13 (with the addition of the voltage divider resistor R4 for the indication of the second prescribed firing setback or the like acceleration level indicated by OUTPUT 2) with the output level from a reference voltage supply (U3) and generate compatible logic level outputs (preferably a logic signal voltage level appropriate for the detecting device electronics). It will be appreciated by those skilled in the art that by providing appropriate additional resistors (in addition to the resistor R4), other voltage levels (i.e., other firing setback or the like acceleration levels) may be similarly detected.

It will be appreciated by those skilled in the art that there are many methods and means to implement the aforementioned logic level comparator components of the passive all-fire detection sensor circuitry of FIG. 17 such as the use of an op-amp. However, in a preferred embodiment, Schmitt triggers are used since in these devices the threshold voltage to which the signal is compared depends on the state of output. This feature is particularly advantageous when the signal rises (or falls) through the switching region in a "noisy" or fluctuating manner since a Schmitt trigger would provide only one switching output, unless the fluctuations are of amplitudes greater than its threshold range.

Figure 18:
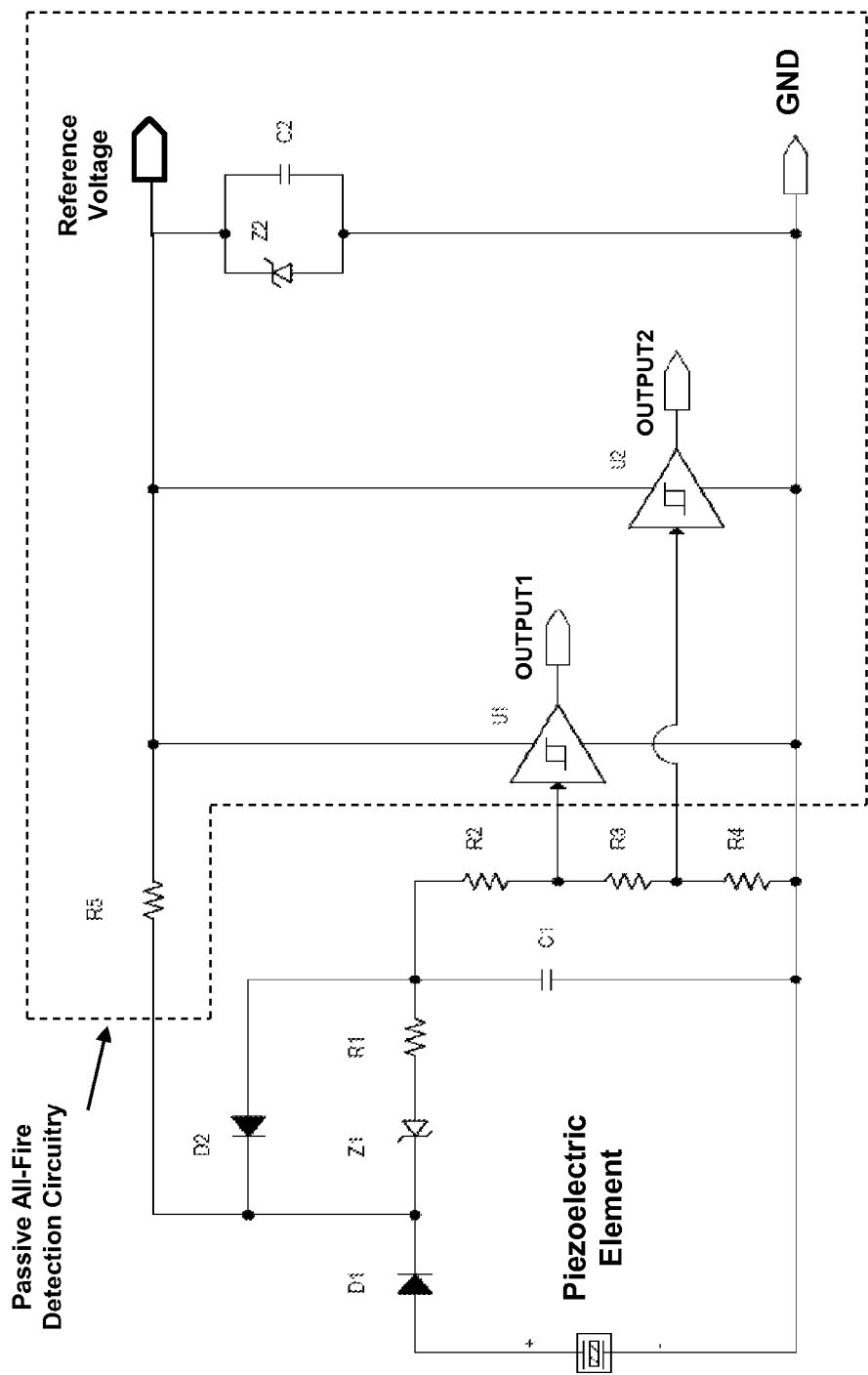
FIG. 18 illustrates an embodiment of the passive all-fire setback acceleration (shock) level detection sensor of FIG. 17 as implemented with Schmitt triggers suitable for use in munitions or other similar applications with environmental noise and/or high shock level fluctuations.

A typical preferred implementation of the passive all-fire detection sensor circuitry of FIG. 17 with the aforementioned Schmitt triggers for detection of two firing setback acceleration (shock) levels is shown in the schematic of FIG. 18. This embodiment of the present "passive all-fire detection sensors" is also designed to operate with very low power to make it possible to package the device in a very small volume. In this embodiment, the "passive all-fire detection circuitry" enclosed by dashed lines is designed to provide logic signal flag(s) for one or multiple firing setback acceleration (shock) levels, in the particular case of the embodiment of FIG. 18 for two firing setback acceleration (shock) levels, that can be directly read/detected by other devices, preferably through digital ports.

It will be appreciated by those skilled in the art that in the safety and all-fire detection circuitry shown in FIG. 13, the proportion of the resistors R2 and R3 were indicated to be selected to provide the desired voltage level at the indicated OUTPUT when the voltage on the capacitor C1 reaches the level corresponding to the prescribed all-fire setback acceleration (shock) level. The voltage at the circuit OUTPUT can then be designed to correspond to any desired voltage level for detection in the case of the present embodiment or any other similar purposes. In a similar manner, the proportions of the resistors R2, R3 and R4 are selected to provide the desired voltage level at the indicated OUTPUT 1 (FIGS. 17 and 18) when the voltage on the capacitor C1 reaches the level corresponding to the prescribed all-fire setback acceleration (shock) level. However, if the experienced all-fire setback acceleration (shock) level is higher than that indicated by the OUTPUT1, then when the voltage at the capacitor C1 reached to a voltage corresponding to the higher (second) voltage level corresponding to the higher (second) all-fire setback acceleration (shock) level, then the voltage at the indicated OUTPUT2 would increase and reach a higher (second) desired voltage level (FIGS. 17 and 18). The voltage level at the OUTPUT2 would then provide the indication of the second (higher) all-fire setback acceleration (shock) level having been reached. It will be appreciated by those skilled in the art that more resistors may be similarly provide (in series with the resistors R2, R3 and R4) to divide the voltage at the capacitor C1 to more different voltage levels, each corresponding to increasing levels of all-fire setback acceleration (shock) levels experienced by the disclosed passive all-fire detection sensors of the embodiments of FIGS. 17 and 18.

It will be appreciated by those skilled in the art that typical current logic signal voltage levels are 3.3V and 5V CMOS level or +/−12V. To provide such compatible voltage levels at the OUTPUT 1 and OUTPUT2 (and other output levels if present) in the embodiments of FIGS. 17 and 18 or the like; a reference voltage supply is also required. Such a reference voltage supply may be provided in a number of ways. In a preferred embodiment shown in the schematic of FIG. 18, the Zener diode Z2 together with the current limiting resistor R5 and the capacitor C2 provide a desired reference voltage level to the Schmitt triggers U1 and U2 from the rectified piezoelectric output. Here the low leakage Zener diode Z2 clips the reference voltage to its breakdown voltage to provide a precise desired reference voltage level. The Schmitt triggers U1 and U2 also reduce noise impact on the high input impedance logic gates of the user provided circuitry.

The operation of the "safety and all-fire detection circuitry" embodiments of FIGS. 13, 19 and 19A were described for the detection of prescribed all-fire conditions in terms of the munitions firing setback acceleration level and its duration. All other no-fire conditions, such as lower level shock loading and vibration due to transportation or short duration shock loading due to accidental drops and other similar events and high noise are differentiated from the prescribed all-fire condition. The operation of the "safety and all-fire detection circuitry" embodiments of FIGS. 13, 19 and 19A when used with an "output voltage threshold detection and switching element" to allow direct flow of current from the piezoelectric element through the indicated "initiator bridge wire" (or any other electrical or electronic or the like elements) to the ground as previously described for the embodiments of FIGS. 14-16 and the operation of the passive "passive all-fire detection sensor" embodiments of FIGS. 17 and 18 were also described for prescribed munitions all-fire setback accelerations level and duration (all-fire condition) detection and operation while rejecting all aforementioned "no-fire" conditions. It is, however, appreciated by those skilled in the art that any one of the above embodiments may also be used to detect other shock or vibration or acoustic noise or other similar acceleration levels instead of the all-fire setback acceleration (shock) levels and similarly operate the circuitry of embodiments of FIGS. 13-19 and 19A.

In certain munitions applications, instead of detecting firing setback (shock) loading, it is highly desirable to provide a sensor that can detect one or more impacts of the munitions with the target and their time history. The munitions may encounter more than one impact, for example, by impacting more than one barrier such as a building wall or ceiling or other multi-layer structures provided to protect the target. In such applications, particularly when multiple impacts are encountered, it is usually also desired for to for the munitions electronics and logics circuitry and/or processor(s) to also have an indication of the impact time, duration and level. In such applications, the munitions is generally provided with the source of electrical energy such as charged capacitors or super-capacitors and/or chemical batteries and/or electrical energy generated by devices harvesting energy from the environment such as shock loading or vibration or vibratory motions or the like to power its microprocessor(s), electronic and logics circuitry and other electrically powered devices.

In the following, the methods of employing the aforementioned "safety and all-fire detection circuitry" of embodiments of FIG. 13 or 19 or 19A to design sensors for detecting one or more target impact (shock) loading and preferably their impact levels as a function of time are described and examples of their preferred implementation are provided. Hereinafter in the present disclosure such sensors are generally referred to as the "impact detection and time history sensors". It will be appreciated by those skilled in the art that such a sensor which is designed to detect (usually significant) barriers, are in fact also detecting (relatively) free space (or void) between such barriers, and are therefore hereinafter may also be referred to as "void detectors" or "void counter".

Figure 20:
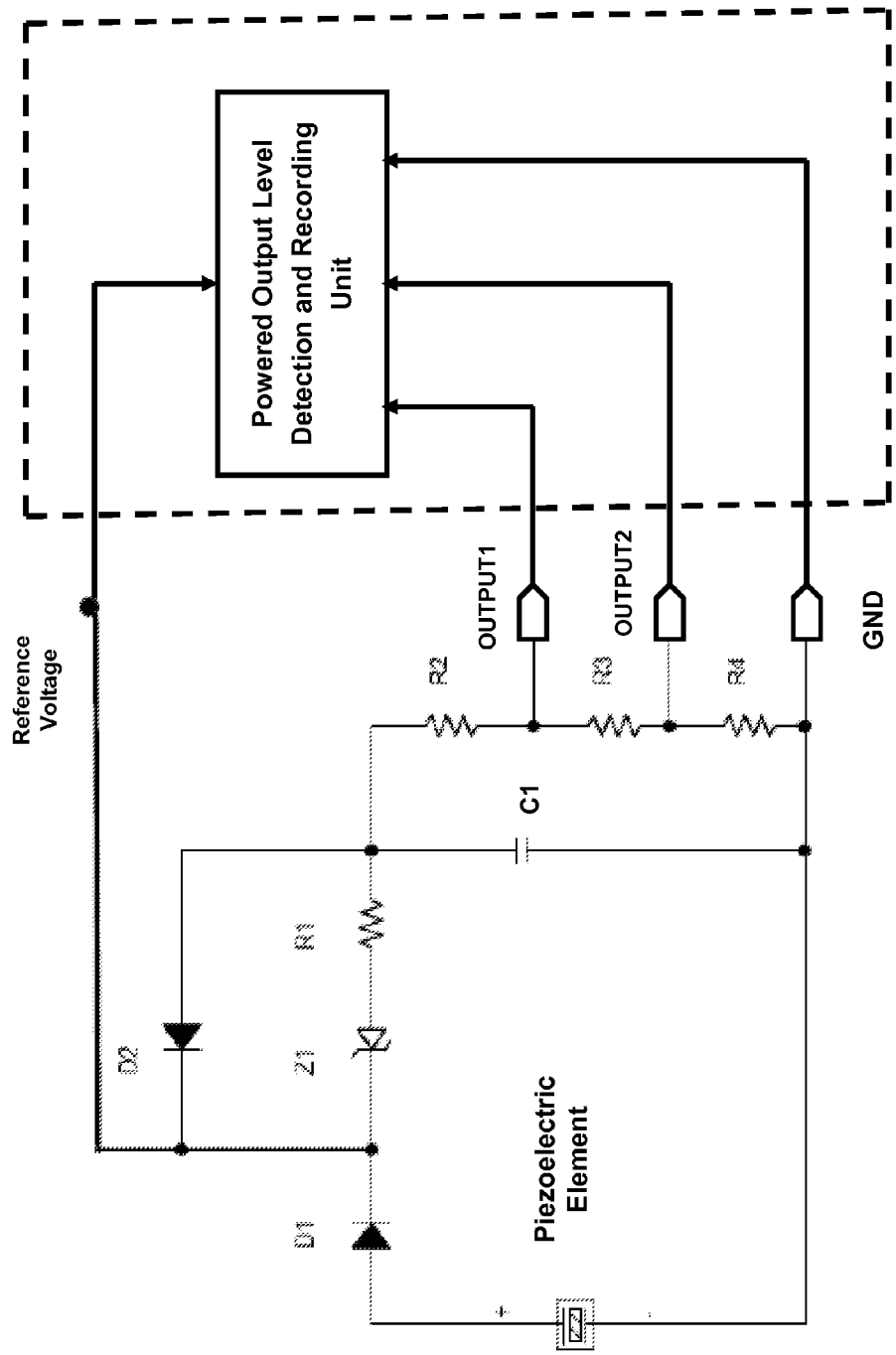
FIG. 20 illustrates an embodiment of the "impact detection and time history sensor" used to detect and "record" the numbers and levels of impacts that are encountered by munitions or the like over a period of time.

The method of designing the aforementioned "impact detection and time history sensors" (or alternatively indicated as "void detector" or "void counter") is described with the schematic shown in FIG. 20. As can be observed, the sensor employs the previously described "safety and all-fire detection circuitry" of the embodiment of FIG. 13 (or its alternative embodiments of FIGS. 19 and 19A). In the schematic of FIG. 20, the "impact detection and time history sensor" circuitry portion of the sensor embodiment is shown enclosed by dashed lines. In this method, the "safety and all-fire detection circuitry" of the embodiment of FIG. 13 (or its alternative embodiments of 19 and 19A) is to detect target impact by the munitions in which the sensor is mounted and "record" the time history of the detected impacts. The process of detecting impact is identical to those described for the embodiments of FIGS. 13, 19 and 19A for the detection of all-fire setback (shock) acceleration except that all-fire setback acceleration is applied to munitions in the direction of their travel for them to gain velocity while the target impact-based deceleration (hereinafter, acceleration and deceleration may be used interchangeably—i.e., without regard to the sign of the rate of change of the sensor velocity) is essentially in the opposite direction and acts to decelerate the munitions along its path of travel (neglecting any generally present sideway acceleration due to an angled target impact or impact with a target with non-uniform resistance to the impact). In general, the "impact detection and time history sensor" embodiment of FIG. 20 may be designed to detect either only the target impacts or both all-fire setback (shock) acceleration as well as target impacts.

It is also appreciated by those skilled in the art that the circuitry output(s) may be similarly used to provide logic signal flags when a target impact of one or more prescribed shock levels and durations is encountered, as for example implemented in the low power circuitry of FIG. 18. Then as shown in the schematic of FIG. 17 and its example of implementation in FIG. 18, the circuitry provides logic signal flags for one or multiple target impact shock acceleration levels that can be directly read by other devices through digital ports. The use of the and previously described logic signal flags, minimal detection electronics and computational capability are required to be provided in the "powered output level detection and recording unit" of the "impact detection and time history sensor" of the embodiment of FIG. 20.

The operation of the "safety and all-fire detection circuitry" embodiments of FIGS. 13, 19 and 19A were described for the detection of prescribed all-fire conditions in terms of the munitions firing setback acceleration level and its duration. In the "impact detection and time history sensor" of the embodiment of FIG. 20, target impact(s) to one or more prescribed impact shock levels are similarly detected. All other "non-impact" conditions, such as lower level shock loading due to encounters with very light structures or objects and vibration during the flight and other similar events and high noise are differentiated from the prescribed impact conditions (usually shock levels and durations). The "passive all-fire detection sensor" embodiments of FIGS. 17 and 18 can also be used as described previously for the detection of prescribed munitions all-fire setback accelerations level and duration (all-fire condition) and rejection of all aforementioned "no-fire" conditions to detect munitions target impact(s) to one or more prescribed impact shock levels (thresholds) while differentiating them from all other "non-impact" conditions.

In the schematic of the basic embodiment of the "impact detection and time history sensors" (or alternatively indicated as "void detector" or "void counter") shown in FIG. 20, as was previously described for the "safety and all-fire detection circuitry" of the embodiment of FIG. 13 (or its alternative embodiments of 19 and 19A), when the munitions equipped with the present "impact detection and time history sensor" impacts a target (here considered to be a significant barrier like a bunker wall or the like—with a significant barrier hereinafter defined as those that cause at least the first prescribed impact threshold level and duration of the "impact detection and time history sensor" to detect it as an impact event), a prescribed impact condition is similarly detected by the voltage level of the capacitor C1 while the circuitry prevents the charging of the capacitor C1 to the prescribed voltage level if the generated piezoelectric charges are due to the aforementioned non-impact conditions (no-fire conditions for the case of the for the case of embodiments of FIGS. 13, 19 and 19A) are encountered. Once an impact condition is detected, the provided "powered output level detection and recording unit" of the "impact detection and time history sensor" shown in FIG. 20 "records" the event and its relative time of occurrence. The detection and "recording" capabilities of the "impact detection and time history sensors" may be implemented in numerous different schemes and using different electronics components and logics circuitry and/or microprocessor most appropriate for the application at hand and the device(s) using the generated information. In munitions applications, however, the main issues of concern in addition to reliability and safety also include low power requirement, volume efficiency (i.e., miniaturization capability), firing setback and harsh environment survivability.

Examples of the implementation of the present "impact detection and time history sensors" of the embodiment of FIG. 20 are provided. It will be appreciated by those skilled in the art that the following embodiments of the present "impact detection and time history sensors" (or alternatively indicated as "void detector" or "void counter") inventions are provided only as examples of their possible implementation, particularly for munitions applications, and should not be considered as an intention to exclude other implementations of the sensor design.

In the schematic of the embodiment of FIG. 20, the "powered output level detection and recording unit" portion of the "impact detection and time history sensor" embodiment is shown enclosed by dashed lines. In the present method, the "safety and all-fire detection circuitry" of the embodiment of FIG. 13 (or its alternative embodiments of 19 and 19A) is used as previously described to detect target impact by the munitions in which the sensor is mounted and "record" the time history of the detected impacts. In the embodiment of FIG. 20, the "safety and all-fire (in this case target impact) detection circuitry" (hereinafter also referred to as "safety and target impact detection circuitry") as is shown to be used to detect two levels of target impact shock levels at OUTPUT1 and OUTPUT2, even though as it was previously described for the embodiment of FIGS. 17 and 18, more than two target impact levels may also be similarly made detectable.

Figure 21:
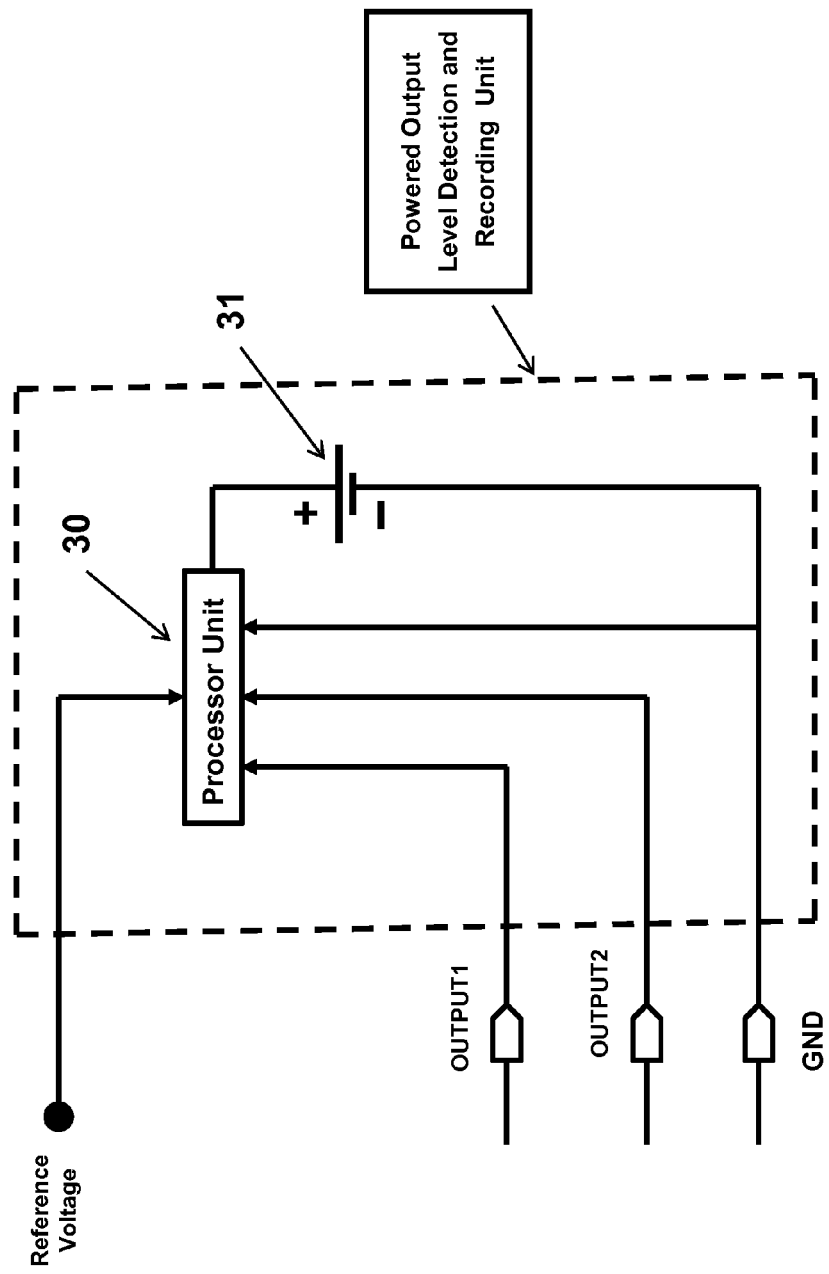
FIG. 21 illustrates an embodiment of the implementation of the "impact detection and time history sensor" of FIG. 20.

In one "impact detection and time history sensor" embodiment, the "safety and target impact detection circuitry" of the embodiment of FIG. 20 is used to provide logic signal flags (for example, as was described for the embodiment of FIG. 18) for one or multiple target impact shock acceleration levels (in the schematic of FIG. 20 for two target impact shock or the like acceleration levels) that can be directly read by the processor unit 30 (or other appropriate logic circuitry or devices) through digital ports as shown in FIG. 21. The processor unit 30 is considered to be equipped with input digital ports, appropriately sized memory, timing source, etc., that are commonly provided on such signal processing units as is well known in the art. As examples, the processor unit 30 may be constructed with CY8C21334-12PVXE from Cypress Semiconductor Corporation which has an internal RC clock and that can work in a wide range of temperatures can be used. For this In FIG. 21, the "powered output level detection and recording unit" portion of the present "impact detection and time history sensor" embodiment (see FIG. 18) is indicated by dashed lines.

In the schematic of FIG. 21, the indicated outputs OUTPUT 1 and OUTPUT 2 are considered to be outputs of the logic level comparators U1 and U2 (see the schematic of FIG. 18). The reference voltage (FIG. 18) may be provided as shown for the embodiment of FIG. 18 or directly from the power source 31 of the "powered output level detection and recording unit" as shown in FIG. 20. As a result, when the munitions impacts a target, when the impact shock acceleration level reaches the prescribed threshold of the first logic level comparator U1, the OUTPUT1 provides a signal indicating the event (preferably by a logic signal voltage level appropriate for the detecting device electronics, for example a 3.3V or 5V or +/−12V as described for the embodiments of FIGS. 17 and 18). Similarly, if the impact shock acceleration level increased further and reaches the prescribed threshold of the second logic level comparator U2, the OUTPUT2 would then provide a signal indicating the event. In a similar manner, if more than two logic level comparators are provided in the "safety and all-fire detection circuitry" of the embodiment of FIG. 20 (as described for the embodiment of FIG. 13 or its alternative of FIGS. 19 and 19A and the embodiments of FIGS. 17 and 18), each prescribed impact shock acceleration level that is reached generates a signal indicating the event to the processor unit 30. The processor would then "record" each event and their relative time.

It will be appreciated by those skilled in the art that as was previously described for the embodiments of FIGS. 13-19 and 19A, when the when the munitions encounter with a significant barrier ends, i.e., when the munitions exits the barrier, the piezoelectric voltage drops (to near zero) below the voltage level on C1 and the diode D2 causes essentially all charges accumulated in the capacitor C1 to be discharged. As a result, the outputs OUTPUT 1 and OUTPUT 2 of all logic level comparators U1 and U2 will drop to near zero, indicating to the processor unit 30 that the target has been essentially exited (at least up to its softer portion indicated to be below the threshold of the first logic level comparator U1). Similarly, once the impact threshold level falls below the level indicated by the logic level comparator U2, the OUTPUT2 of the comparator drops to near zero, thereby similarly indicating the event to the processor unit 30.

Figure 22:
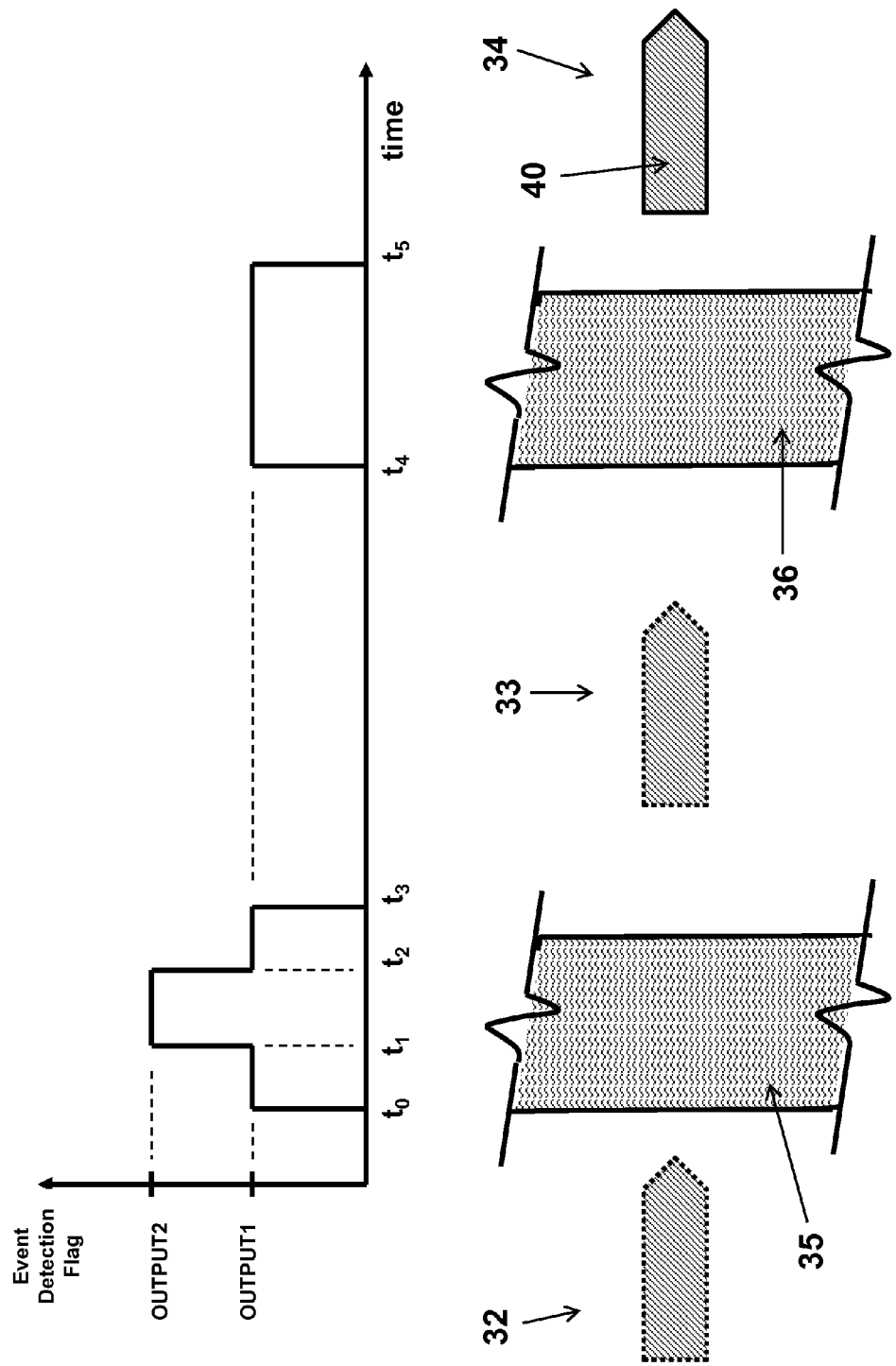
FIG. 22 is a plot of the "impact detection and time history sensor" of the embodiment of FIG. 20 "recording" of the encounter of the munitions using the sensor with two significant barriers.

As an example, if the munitions in which the present "impact detection and time history sensor" embodiment of FIGS. 20-21 is mounted encounters two significant barriers (i.e., barriers that cause at least the first prescribed impact level and duration of the "impact detection and time history sensor" to detect it as an impact event), then the time history of the detected events may look as shown in the plot of FIG. 22. In the plot of FIG. 22, the munitions 40 is shown in the positions 32, 33 and 34, corresponding to its position prior to encountering the significant barrier 35, after having encountered the significant barrier 35 and prior to encountering the significant barrier 36 and after having encountered the significant barrier 36, respectively. The top graph of FIG. 22 is intended to show the output flag activation condition as a function of time as the munitions 40 travels from its position 32 through the significant barrier 35 and then travels through its position 33 to the significant barrier 36 and through it to its position 34. In the top graph of FIG. 22, the "impact detection and time history sensor" that is mounted in the munitions 40 is considered to experience the impact with the significant barrier 35 and at the indicated time $t_0$ detect the aforementioned first target impact shock level and thereby generate an output flag at the OUTPUT1, with the impact shock level increasing to the aforementioned second target impact shock level and thereby generating an output flag at the OUTPUT2 at the indicated time $t_1$. The impact shock level experienced by the munitions 40 is then considered to stay around the aforementioned second impact shock level until the time $t_2$, at which time the impact shock level drops below the second but above the first impact shock level and stays in the same region until the time $t_3$, at which time the impact shock level drops below that of the aforementioned first impact shock level. The munitions 40 then travels towards the second significant barrier 36 and at the time $t_4$ the "impact detection and time history sensor" is considered to detect the aforementioned first target impact shock level and thereby generate an output flag at the OUTPUT1 until the time $t_5$, at which time the impact shock level drops below that of the aforementioned first impact shock level.

In an embodiment, processor unit 30 of the "impact detection and time history sensor" embodiment of FIGS. 20-21 is provided with a timing clock, I/O ports and the related components and enough memory capacity to record the events indicated in the top graph of FIG. 22 in terms of the generated output flags and their relative times of occurrence $t_0$-$t_5$ for use for other electrical and electronics units of the munitions.

It will be appreciated by those skilled in the art that the aforementioned time $t_0$ and $t_4$ would usually occur slightly after the munitions impact with the significant barriers 35 and 36, respectively, and that the amount of such delays is dependent on the resistance of the encountered significant barrier surfaces and the strength characteristics of the munitions structure, particularly around its impacting surfaces to the location of the "impact detection and time history sensor" mounting.

Figure 23:
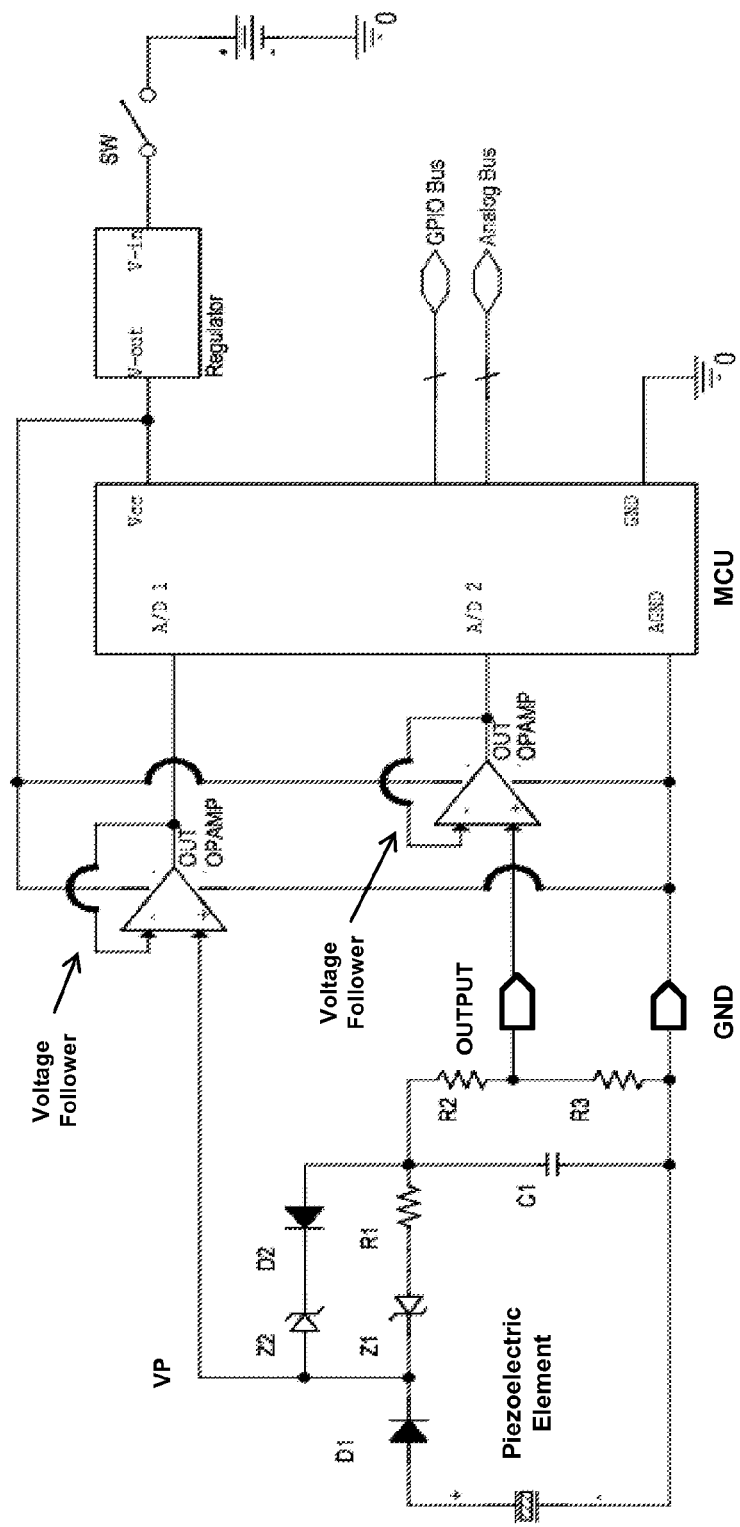
FIG. 23 illustrates another embodiment of the implementation of the "impact detection and time history sensor" of FIG. 20.

A schematic of an alternative embodiment of the "impact detection and time history sensor" of FIGS. 20 and 21 is shown in the schematic of FIG. 23. This embodiment employs one of the basic "safety and all-fire detection circuitry" of embodiments of FIG. 13 or 19 or 19A to design sensors for detecting one or more target impact (shock) loading and their impact level profiles as a function of time. It will be appreciated by those skilled in the art that as was previously indicated, such sensors which are designed to detect (usually significant) barriers, are in fact also detecting (relatively) free space (or void) between such barriers and can also be referred to as "void detectors" or "void counter". In the example of basic implementation of the present embodiment shown in FIG. 23, the voltage signals from the "safety and all-fire detection circuitry" output (indicated as OUTPUT in the schematic of FIG. 23) and the piezoelectric element voltage output (indicated as VP in the schematic of FIG. 23) are connected to the analog-to-digital converter (A/D) inputs of the MCU (micro-controller unit) via voltage followers, which can be implemented with the Texas Instruments OPA2277 high precision operational amplifier as is well known in the art.

The ground "safety and all-fire detection circuitry" (GND) is connected to the analog ground of the MCU. It is noticed that the voltage followers can also be configured to specific gain with resistors, so that they scale the voltage to be measured at the OUTPUT of the "safety and all-fire detection circuitry" as well as the voltage VP of the piezoelectric element (usually down) to the measurement range of A/D converters of the MCU.

The micro-controller unit (MCU) may be of any type appropriate of the specific application. As an example, we may use a model CY8C28243-24PVXI from Cypress Semiconductor Corporation for this purpose. Such a MCU features on-chip RC clock of up to 48 MHz with 2.5% fabrication accuracy, and is integrated with 16 KB flash memory, 1 KB SRAM memory and A/D modules (up to 15.6 k sample rate at 6 bit resolution). Additional memory may also be added depending on the selected sampling rates and the total length of time that sampling is desired to be continued.

In general, a voltage regulator can provide proper voltage source from power supplier (a battery or capacitor or supercapacitor or the like) to the MCU. The switch SW enables the MCU to start the program. The switch can for example be a simple manual on/off switch when the system is used in the laboratory for testing purposes, or when used in munitions, it could be an electronic switching device similar to the one described for the embodiment of FIG. 16, which is similarly powered by the piezoelectric element or could be a latching G-switch that is turned on by the firing setback acceleration and would stay on following activation.

Once the switch SW is closed, the MCU would continuously sample voltage signals ay A/D 1 and A/D 2, FIG. 23, and store the information as a function of time in the device internal and external (if provided) memory or is transmitted directly to the host processor (munitions control system processor, which may be the MCU itself) for processing. As a result, essentially continuous time history of impact shock levels are provided by the device once such impacts with levels above the prescribed levels are detected. For example, considering significant barrier encounters shown in the schematic of FIG. 22, the MCU is preferably programmed to ignore the A/D 1 input until it reaches the aforementioned prescribed level indicating an encounter with a significant barrier (time $t_0$ in the plot of FIG. 22), and sample/record or process impact shock levels until the time $t_3$, when the munitions 32 has exited the significant barrier 35. As a result, a nearly continuous profile of impact shock level, i.e., barrier "strength", as a function of time is measured (as compared to the step-wise output shown in the plot of FIG. 22 for the portion of the shock levels between the indicated OUTPUT1 and OUTPUT2). It is also appreciated by those skilled in the art that since the munitions velocity is approximately known or readily calculated, the impact shock level profile as a function of the barrier thickness is also approximately determined. The impact shock level is similarly measured during the round 32 encounter with the second significant barrier 36, FIG. 22.

When a relatively short string of data is to be recorded, a circular buffer can be formed. Algorithms well known in the art can then be run in the MCU processor to monitor the buffer. Then when the buffer indicates a valid event sequence, for example for the case of munitions, when a prescribed type and number of encounters with previously described significant barriers are detected, the algorithm would pass the information to the munitions control processor for decision making purposes or in testing equipment, would save the data on its non-volatile memory.

The rest of the available GPIO (general purpose input/output) bus and analog (A/D and D/A) bus of the MCU can be used to input/output digital flags and analog control signals. For example, by using two GPIO pins as SCLK and SDATA, an I2C serial port can be implemented for communicating with host processor (if provided) to upload the samples stored in MCU's memory.

It will be appreciated by those skilled in the art that the "impact detection and time history sensor" embodiment of FIG. 23 has the advantage of being capable of providing essentially continuous impact shock level information once the prescribed impact threshold level and duration has been reached. In contrast, the embodiments of FIGS. 20 and 21 provide a step-wise, multi-level indication of the impact shock level information. The latter information is usually sufficient in many applications. In addition, the embodiments of FIGS. 20 and 21 also have the advantage of requiring relatively simple electronics to construct without the need of MCUs and A/Ds and the like. Thereby these devices become significantly less complex, less costly and faster in response.

It is also appreciated by those skilled in the art that more than one "impact detection and time history sensor" (of either one of the embodiments of FIG. 20, 21 or 23) may be mounted in munitions (e.g., round 32 shown in FIG. 22) to detect/measure impact shock levels along the path of travel of the round (see FIG. 22) as well as in the lateral direction(s). In a preferred embodiment, at least three such "impact detection and time history sensors" are used and at least one is oriented to detect/measure impact shock level in the axial direction (i.e., along the path of travel of the round) and at least two are used to detect/measure impact shock levels in two independent lateral directions (preferably orthogonal directions). In such configurations, the impact detection and time history sensors are capable of providing information as to the direction of target impact and/or the structural characteristics of the impacted and penetrated target.

It is noted that the piezoelectric elements used in the embodiments of FIGS. 13-21 and 23 are in fact electrical energy generators that convert mechanical energy to electrical energy (charges) that are then used to power the described circuitry and elements. It is also noted that the indicated piezoelectric elements are assemblies containing piezoelectric (preferably stack) elements and in general other elements such as mass and spring (elastic) elements that are packaged in a particular manner to allow them to generate the electrical energy when subjected to a prescribed shock loading direction. In the following, the basic methods of packaging to construct such piezoelectric-based electrical energy generators suitable for the present applications are described in detail. It is, however, noted that the provided example of such packaging is provided only for describing the disclosed basic methods and are not intended to limit this disclosure to this particular packaging configuration.

Figure 24:
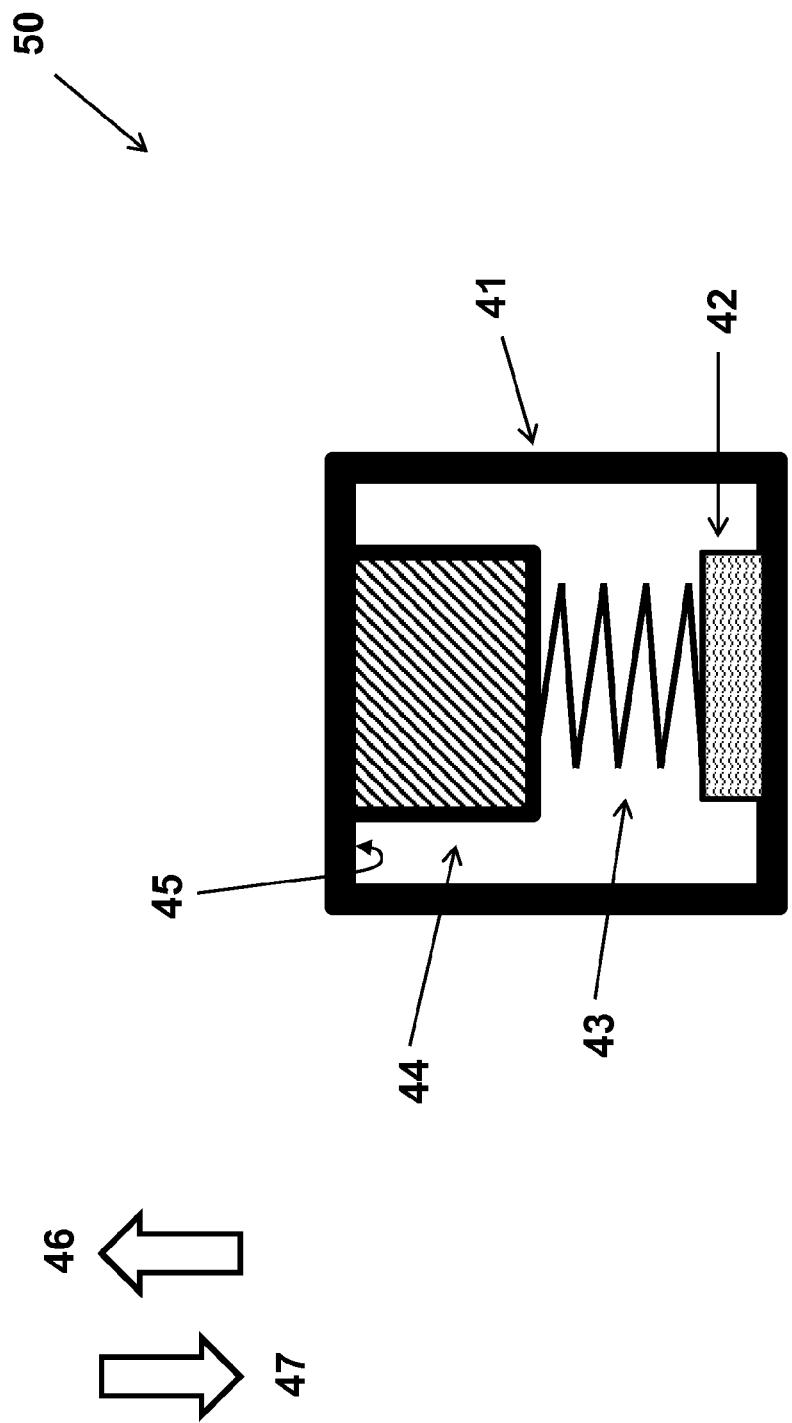
FIG. 24 is the schematic of the embodiment of a piezoelectric-based powering source for use in the embodiments of FIGS. 13-21 and 23.

In one embodiment, the aforementioned piezoelectric-based electrical energy generator 50 (herein referred to as "piezoelectric element") of the embodiments of FIGS. 13-21 and 23 is packaged as illustrated schematically in FIG. 24. The piezoelectric element 50 is provided with a housing 41, which could for example cylindrically shaped or any other shape that best matches the available space in the device it is being mounted. At least one piezoelectric (preferably stack) member 42 is fixedly attached to one side of the housing 41 (in the schematic of FIG. 24 to the bottom surface of the housing 41 as seen in the illustration). A mass 44 is then positioned above the piezoelectric member 42 together with the spring (elastic) element 43, which separates the mass 44 from the piezoelectric member 42 as shown in the schematic of FIG. 24. The spring element 43 is preferably preloaded in compression so that the mass element 44 is normally in contact with the top surface 45 of the housing 41, even when the subjected to certain level of acceleration in the direction of the arrow 46.

When the piezoelectric element 50 is used in the embodiments of FIGS. 14-16 to initiate pyrotechnic materials via the provided bridge wires as a result of the all-fire setback shock acceleration, or for the detection of one or more firing setback acceleration (shock) levels as was described for the embodiments of FIGS. 17 and 18, or for other firing setback acceleration (shock) purposes in the "safety and all-fire detection circuitry" embodiments of FIGS. 13, 19 and 19A, then the piezoelectric element 50 is mounted in the munitions such that it is oriented to experience the firing setback acceleration essentially in the direction of the arrow 46. The spring element 43 is generally selected to have relatively high stiffness and preloaded to keep the mass 44 in contact with the surface 45 of the housing 41. And if the device is subjected to acceleration (shock) loading in the direction of the arrow 47 (direction of the firing set-forward acceleration) or in the lateral directions, then level of forces acting on the piezoelectric member 42 is minimally changed, thereby the piezoelectric member would generate minimal charges. However, if the piezoelectric element 50 is subjected to shock loading due to the firing setback in the direction of the arrow 46, then the acceleration would act on the inertial of the mass 44 and applies a force on the piezoelectric member 42 proportional to the mass of the mass 44 and the setback acceleration and thereby causes it to generate electrical charges to operate the aforementioned circuitry.

On the other hand, when the piezoelectric element 50 is used in the "impact detection and time history sensor" embodiments of FIG. 20, 21 or 23, then the piezoelectric element 50 is mounted in the munitions oriented such that it experiences the impact shock acceleration in the direction of the arrow 46. As a result, the firing setback acceleration will not generate a significant loading of the piezoelectric member 42 and thereby would not generate a significant amount of electrical charges to activate the "impact detection and time history sensors".

It will be appreciated by those skilled in the art that the aforementioned methods of designing the disclosed "safety and all-fire detection circuitry" embodiments of FIGS. 13, 19 and 19A; the embodiments of FIGS. 14-16 to initiate pyrotechnic materials via the provided bridge wires as a result of the all-fire setback shock acceleration; the passive shock detection embodiments of FIGS. 17 and 18; and the "impact detection and time history sensor" embodiments of FIG. 20, 21 or 23 as well as their similar implementations may be used to for non-munitions, including many industrial as well as commercial applications.

For example, the passive all-fire setback acceleration (shock) level detection sensors of the embodiments of FIGS. 17 and 18 may be used to detect vibration in machinery when its amplitude exceeds a prescribed threshold and provide input to the system control to take appropriate action such as reduce power or undergo emergency stop. In a similar manner, the sensors may be used to detect the start of a process in machinery and initiate certain processes; for example detect the start of drilling process at the drilling head of an oil or gas drilling equipment and thereby turn-on certain processes such turning on the sensory and control and data acquisition and transmission electronics to minimize power consumption or the like or perform other on/off switching or flagging action.

Even the embodiments of FIGS. 14-16 to initiate pyrotechnic materials via the provided bridge wires as a result of the all-fire setback shock acceleration can be used to initiate pyrotechnics and/or explosives used to actuate certain Cartridge Actuated Devices (CAD) for emergency actuation of valves or door/exits or ejection of pilot or initiate other emergency actions when an explosion or earthquake or other high-shock producing events have occurred.

It will be appreciated by those skilled in the art that the safety and all-fire detection circuitries of FIGS. 13, 19 and 19A may be used in any of the embodiments of FIGS. 14-18, 20 and 23 depending on the application.

It is also appreciated by those skilled in the art that implementations other that the circuitry shown in the schematics of FIGS. 13-21 and 23 for the disclosed methods are also possible for achieving essentially the same functionalities. As such, the disclosed implementations of the disclosed methods as shown in the schematics of FIGS. 13-23 are to provide examples of their preferred embodiments and are not intended to limit their implementations only to the disclosed implementations.

It is also appreciated by those skilled in the art that as was described for previous embodiments, a magnet and coil generator 20 that forms a vibrating mass-spring system shown in the schematic of FIG. 12 may be similarly used in place of or in addition to the piezoelectric elements of the embodiments of FIGS. 13-20 and 23.

Figure 25A:
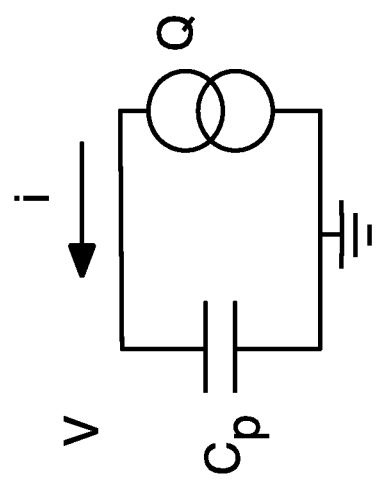
FIG. 25A illustrates a model of a piezoelectric element used in the disclosed embodiments for generating electrical charges for harvesting and sensing when subjected to external loading.

A stand-alone piezoelectric (usually in stack form) element can be modeled as a capacitor $C_p$ connected in parallel to a charge source Q as shown in FIG. 25A. The charge source Q generates charge proportional to the axial (normal) strain of the piezoelectric element as it is subjected to axial (normal) loading, and thereby sends the charge as current i to the capacitor $C_p$ of the piezoelectric element. The charges accumulated on the capacitor $C_p$ produces a voltage V, which is the so-called open circuit voltage of the piezoelectric element. When the piezoelectric element is connected to another circuitry, the generated charge and current are the same, but due to the resulting charge exchange with the other circuitry, the in circuit voltage of the piezoelectric element may be different from the open circuit voltage V.

Figure 25B:
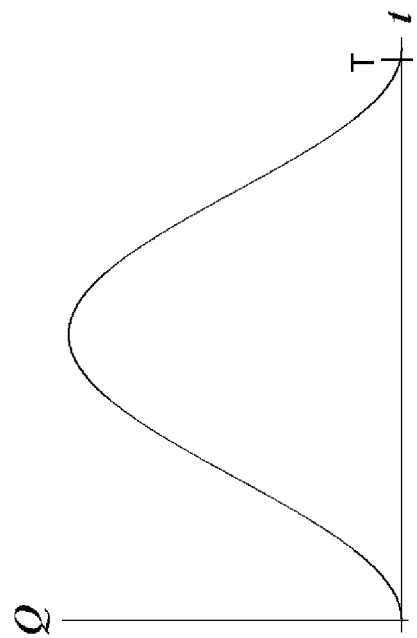
FIG. 25B is a plot of the generated piezoelectric charge as a function time during a typical short duration impact (pulsed) loading.

A typical plot of the profile of the charge level on the piezoelectric element (FIG. 25A) as it is subjected to a short duration impact loading as a function of time is shown in FIG. 25B. The maximum amount of charges Q (in Coulomb) is dependent on the size of the piezoelectric element and the applied impact force levels. In most cases of interest, the impact loading duration may be as low as 10-100 microseconds.

It will be appreciated by those skilled in the art that when harvesting electrical energy from shock loading impact or other similar very short duration "pulsed" loading, the mechanical to electrical energy converting elements such as piezoelectric elements or magnet and coil elements used for this purpose are subjected to very short duration "pulsed" excitation. Currently used electrical energy collection and capacitor storage methods are, however, extremely inefficient when the "pulse" duration is very short and sometimes in the order of tens of microseconds or even less. Methods and devices are therefore highly desirable for efficient harvesting the electrical energy that is generated by electrical energy generators such as piezoelectric elements or magnet and coil elements when subjected to such very short duration "pulsed" loading.

Figure 26:
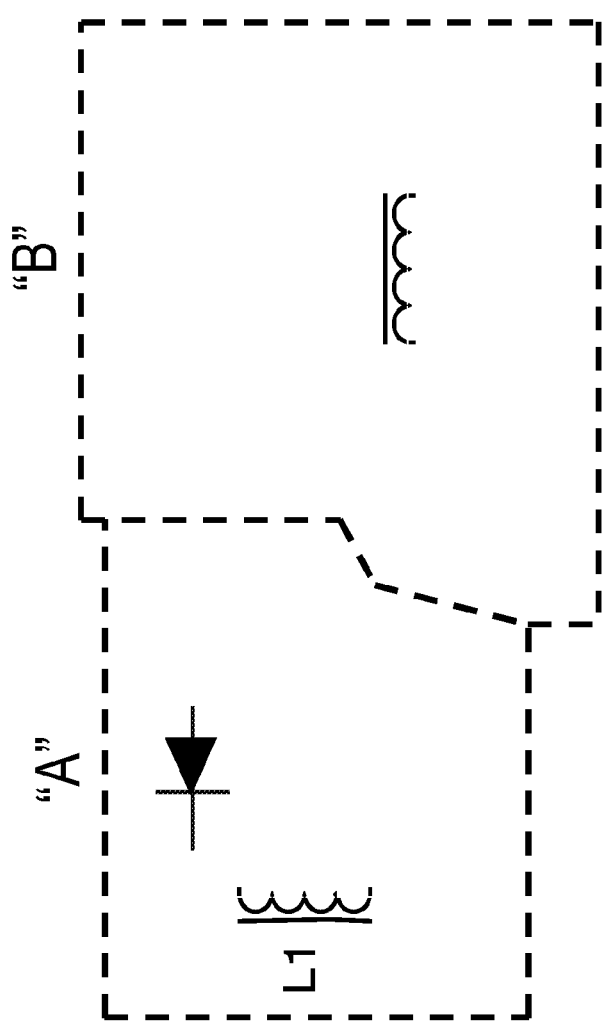
FIG. 26 illustrates circuitry of an embodiment for high efficiency harvesting of electrical energy generated by piezoelectric or magnet and coil elements of a generator device when subjected to very short duration pulses.

The method and devices of providing a highly efficient energy harvesting device is shown in the basic circuitry of the embodiment of FIG. 26. Here the circuitry of FIG. 26 and its operation is described for the very short duration charges that are generated by a piezoelectric element when it is subjected to very short duration loading, such as those experienced as a result of very short duration impact loading. In addition, in the circuitry of FIG. 26 only the very basic elements that are needed for its proper operation are shown. But it will be appreciated by those skilled in the art that a user may add other elements to adapt this circuitry to many other specific applications at hand.

The novel very short duration pulse energy harvesting circuitry of the embodiment of FIG. 26 harvests energy from short duration charges generated by the device piezoelectric element (indicated in short as piezo in FIG. 26) in two distinct stage. In the first stage, the electrical energy (charges) generated by the piezoelectric element due to the very short duration impact loading (a transient pulse) is stored in the piezoelectric element (acting as an electrical energy storage capacitor). In the second stage, the electrical energy stored in the piezoelectric element is transferred to the energy harvester capacitor(s).

The basic energy harvesting circuitry for very short duration loading of piezoelectric elements shown in FIG. 26 may be divided into two sub-circuits "A" and "B" as indicated by dashed lines in FIG. 26. As can be seen in FIG. 26, the sub-circuit "A" includes the inductor L1, diode D1 and the piezoelectric element. This circuit and without the diode D1 would form an LC resonant circuitry, and its resonance frequency is selected based on the range of the duration of the piezoelectric loading as seen in FIG. 25B, with the period of the resonant frequency being preferably around 0.5 to 1.5 times the maximum duration of the piezoelectric element loading (indicated by the duration of the charge in FIG. 25B).

The inductor L2 and capacitor C of the sub-circuit "B" form another LC circuitry (without the diodes D3) with the natural frequency, which is selected to be significantly lower than that of the natural frequency of the sub-circuit "A". As a result, during the aforementioned very short duration loading of the piezoelectric element, FIG. 26, which would result in a very short duration generated charge pulse of the type shown FIG. 25B, only the sub-circuit "A" of the device (FIG. 26) would provide a significant response to the generated "pulsed" charge. That is, during the short duration of the generated "pulsed" charge, FIG. 25B, the effects of the presence of the sub-circuit "B" can be neglected.

Figure 27:
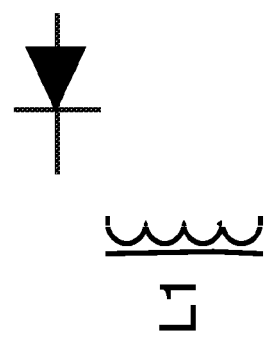
FIG. 27 illustrates the one sub-circuitry of the basic circuitry of the embodiment of FIG. 26 for high efficiency harvesting of electrical energy from piezoelectric elements subjected to very short duration pulses.

The sub-circuit "A", FIG. 26, with the piezoelectric element model of FIG. 25A is shown in FIG. 27. As was previously described, as the piezoelectric element of this circuitry is subjected to a very short duration loading, it would produce charges essentially proportional to the level of subjected loading, a typical such charge level profile having been illustrated in the plot of FIG. 25B. Here, as the charges build up on the piezoelectric element due to the applied short duration loading, as indicated in FIG. 27, a current $i_1$ is generated by the piezoelectric equivalent charge source Q; resulting in a current $i_2$ passing through the inductor L1; and a current $i_3$ that would result in charging (or discharging) the equivalent capacitor $C_p$ of the piezoelectric element, with the relationship $i_1 = i_2 + i_3$ having to be satisfied at all times. In the circuit diagram of FIG. 27, $V_p$ is the circuit voltage of the piezoelectric element.

Figure 28:
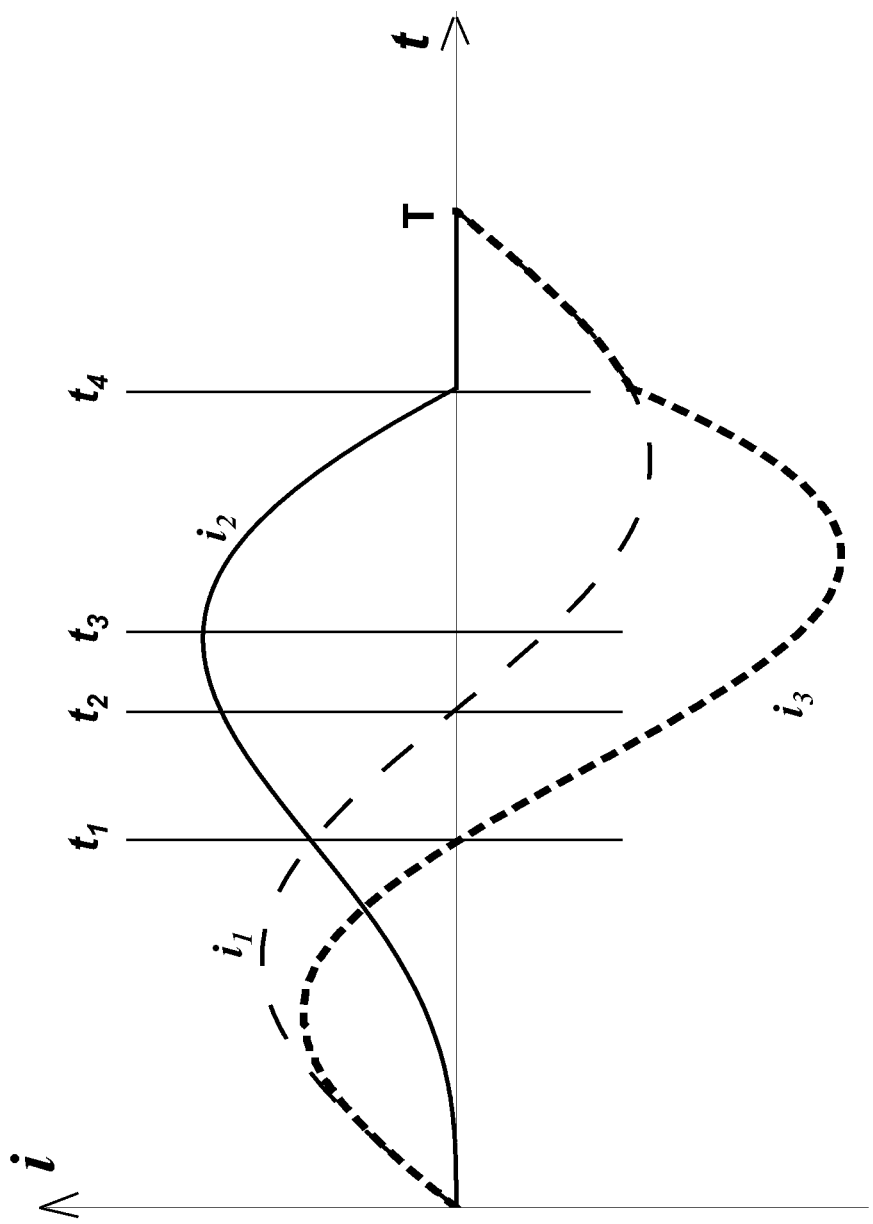
FIG. 28 illustrates the plot of typical currents i1, i2 and i3 shown in FIG. 27 generated during short duration loading of the piezoelectric element of FIG. 26.
Figure 29:
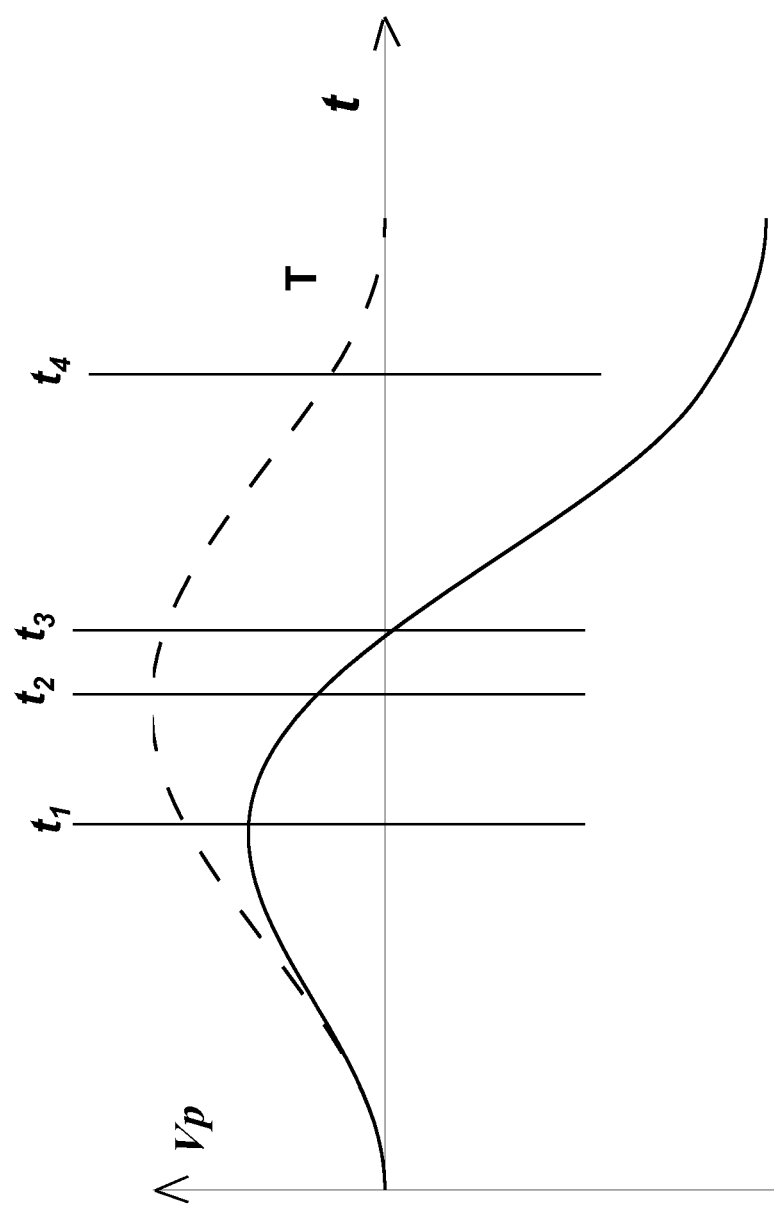
FIG. 29 illustrates the plot of typical voltages corresponding profiles of the voltage $V_p$ for the open circuit case of the piezoelectric element as shown in its equivalent circuit of FIG. 25A (dashed line) and in circuit (FIG. 27) voltage during the short duration impact loading of the piezoelectric element (solid line).

As an example, consider the case in which the period of the natural frequency of oscillation of the LC circuit formed by the inductor L1 and the equivalent capacitor $C_p$ is 75% of the impact duration T (FIG. 25B). The resulting currents $i_1$, $i_2$, and $i_3$ during the impact would then have typical profiles as shown in the plot of FIG. 28. FIG. 29 is the plots of the corresponding profiles of the voltage $V_p$ for the open circuit case, i.e., for the piezoelectric element alone as shown with its equivalent circuit in FIG. 25A (dashed line) and in circuit (FIG. 27) voltage during the short duration impact loading of the piezoelectric element (solid line).

At the beginning of the process of short duration impact loading of the piezoelectric element (FIG. 26), the charges generated by the piezoelectric element produces a current $i_1$, FIG. 27. The current $i_1$ will then branches into the current $i_2$ and $i_3$ as shown in FIG. 28. The positive current $i_3$ begins to accumulate charges on the piezoelectric equivalent capacitor $C_p$, thereby the voltage $V_p$ begins to increase. The current $i_2$ cannot increase instantly due to the presence of the inductor L1, which limits the change of current to stay proportional to the voltage across the inductor. Thus, the electrical energy generated by the piezoelectric element loading due to the generated charges is transferred to the inductor L1 and the capacitor $C_p$. The energy stored in the capacitor $C_p$ being proportional to the square of the voltage $V_p$, and the energy stored in the inductor L1 being proportional to the square of the current $i_2$.

During the process of short duration impact loading of the piezoelectric element (FIG. 26), at certain time $t_1$, the inductor current $i_2$ catches up with the current $i_1$, and since the voltage $V_p$ is still positive, $i_2$ would still keep on increasing, FIGS. 27 and 28. At this point, the current $i_1$ is generally still positive but decreasing. Therefore, at the time t1, the current $i_3$ becomes zero and begins to flow in the opposite direction, i.e., becoming negative, FIG. 28. During the process of short duration impact loading of the piezoelectric element, the (circuit) voltage $V_p$ of the piezoelectric element (FIG. 27) will vary as shown with solid line in the plot of FIG. 29. As can be seen in the plot of FIG. 29, as long as the current $i_3$ is positive, the capacitor $C_p$ is charged, thereby at the time $t_1$ when the current $i_3$ becomes zero and begins to become negative, the voltage $V_p$ reaches its positive peak level. From that point on, since the current $i_3$ is always negative during the remaining of the short duration impact loading of the piezoelectric element, the current $i_3$ keep on negatively charge the capacitor $C_p$. The voltage $V_p$ would thereby begin to decrease as shown in FIG. 29 until it becomes zero at the time $t_3$. It is noted that after the time $t1$, the electrical energy generated by the piezoelectric element as well as the electrical energy stored in the capacitor $C_p$ begin to be transferred to inductor L1.

At the time $t_2$, FIGS. 28 and 29, the piezoelectric element has experienced its peak loading, thereby generating its maximum open circuit voltage (FIG. 29) and charges (FIG. 25B). From this point on, the piezoelectric element will begin to absorb charges, and the current $i_1$ would therefore change direction and becomes negative as shown in FIG. 28. Noting that since the voltage $V_p$ is still positive at this time, i.e., at time $t_2$, the current $i_2$ is still positive and increasing. As a result, from the time $t_2$, the current $i_1$ continues to become more negative (i.e., the flow of the current $i_1$ increases in opposite direction of that shown in FIG. 27) and will generally cause the current $i_3$ to keep on becoming more negative due to the flattening of the level of the current $i_2$, FIG. 28, thereby continuing to decrease the voltage $V_p$, FIG. 29. From the time $t_2$ and as long as the voltage $V_p$ is still positive, part of the energy stored in the capacitor $C_p$ is being transferred to the inductor L1 while part of the energy (charges stored in the capacitor $C_p$) is returned back to the piezoelectric element.

At time $t_3$, the voltage $V_p$ reduces to zero while the current $i_2$ reaches its maximum and the current $i_3$ keeps its negative trend. The energy stored in the inductor L1 will also reach its maximum and the charges in the capacitor $C_p$ are fully discharged. At this time $t_3$, the capacitor $C_p$ is ready to collect negative charges. The currents $i_1$ and $i_2$ are combined and begin to negatively charge the capacitor $C_p$, until the time $t_4$, when all the energy in the inductor L1 has been transferred to the capacitor $C_p$, FIG. 28. At this time, i.e., at the time $t_4$, the current $i_2$ becomes zero, FIG. 28, and would generally tends to go negative and draw energy from capacitor $C_p$. However, the presence of the diode D1, FIG. 27, prevents the return current. As a result, from this time ($t_4$) on, the inductor L1 is effectively disconnected from the circuitry and the charge source Q (FIG. 27) produces negative current $i_1=i_3$, and keeps on accumulating negative charges on the capacitor $C_p$ until the short duration impact ends at the time T.

As can be seen from the voltage plots of FIG. 29, the open circuit voltage (dashed line) and in circuit voltage $V_p$ of the piezoelectric element has the same profile as the generated charge Q shown in the plot of 25B since they are proportional to each other. The in circuit voltage (solid line in FIG. 29) however reaches its positive maximum very early on at time $t_1$, when the current $i_3$ becomes zero (FIG. 28). After the time $t_1$ the current $i_3$ is always negative, and hence the in circuit voltage keeps dropping until the end of impact loading, i.e., at time T. It will be appreciated by those skilled in the art that that the area under the $i_3$ curve corresponds to the amount of charges that are finally stored in the equivalent capacitor $C_p$ of the piezoelectric element and that the final in circuit voltage is higher than the maximum open circuit voltage.

It will be appreciated by those skilled in the art that in the above example, all components of the provided circuitry are considered to be ideal and linearly behaving. In addition, the piezoelectric element is considered to produce charges proportional to the applied short duration impact loading, i.e., its own dynamic behavior is also neglected. These assumptions are obviously not totally true and the described response of a real system is expected to vary slightly from its idealized model. For example, inductors usually also provide certain amount of resistive load and the equivalent capacitance $C_p$ of the piezoelectric element would also exhibit leakage. However, the above idealized model (FIG. 27) still does clearly show the disclosed novel method of harvesting a very high percentage of the total charges generated by a piezoelectric element when it is subjected to very short duration pulses, which is not possible to achieve by any of the currently available methods of energy harvesting from piezoelectric elements when subjected to short duration (usually related to impact or other similar type of) loading.

It will also be appreciated by those skilled in the art that neglecting commonly encountered losses in actual components such as those mentioned above, at the end of the imparted very short duration (usually impact type) loading of the piezoelectric element, FIGS. 26 and 27, the absolute value of the final (negative) voltage $V_p$ of the equivalent capacitor $C_p$ of the piezoelectric element will be significantly higher than the maximum open circuit voltage that can be achieved. This is obviously the case with the present novel circuitry since the charges generated during loading portion of the loading cycle (during which the piezoelectric element is subjected to increasing compressive loading) is summed up with the charges being "returned" to the piezoelectric element during the unloading portion of the loading cycle (during which the applied compressive load on the piezoelectric element is reduced to zero by the end of the loading cycle). In fact, if we neglect all losses, at the end of the short duration impact loading of the piezoelectric element, the final amount of charges stored on the equivalent capacitor $C_p$ of the piezoelectric element is equal to twice the peak value of charges generated by the piezoelectric element at its peak loading, i.e., the present novel circuitry can theoretically deliver 100% energy harvesting efficiency.

In the present disclosure, the short duration loading of piezoelectric elements are indicated mostly as those resulting from impact type of loading. This is usually the case since impact type of loading between relatively stiff objects would generate such short duration compressive stresses. It is, however, appreciated by those skilled in the art that any other mechanism by which very short duration loading is imparted on the energy harvesting piezoelectric elements can also use the disclosed novel method highly efficient charge collection and storage. In general, the duration of the shock is considered to be short and in the order of tens or at most hundreds of microseconds since such very short duration charges is very difficult to collect and store using currently available methods. In addition, with very short duration loading (generated charge "pulses"), the required inductor L1 (FIGS. 26 and 27) are relatively small.

It is also appreciated by those skilled in the art that the reason for only considering compressive loading during short duration axial (normal) loading of the piezoelectric elements is the fact that due to their brittle nature, piezoelectric elements can only be subjected to relatively small tensile stresses. Thereby, for energy harvesting purposes in particular, piezoelectric elements should be designed to be subjected to compressive loading to maximize the level of stresses (strains) that they are subjected to and thereby have them generate their maximum amount of electrical charges. It is, however, appreciated by those skilled in the art that properly poles piezoelectric elements may also be used in energy harvesting devices that subject them to other modes of stresses such as in shear. In any case, the novel method of harvesting the generated charges (electrical energy) can still be used to collect the generated electrical charges for storage in capacitors or for other direct usage.

At the completion of the short duration (usually impact) loading of the piezoelectric element, FIG. 26, the generated charges were shown to be stored in the equivalent capacitor $C_p$ of the piezoelectric element, FIGS. 25A and 27. The function of the sub-circuit "B" of device of FIG. 26 is to transfer the stored electrical energy to the device storage capacitor C.

In the sub-circuit "B" of the energy harvesting device of FIG. 26, the inductor L2, diodes D2 and D3 and the capacitor C make a capacitance energy transfer circuitry to harvest the energy stored in the equivalent capacitor $C_p$ of the piezoelectric element, FIGS. 25A and 27. As was previously noted, the natural frequency of the sub-circuit "B" (without the diodes D2 and D3) is considered to be significantly lower than that of the sub-circuit "A" (without the diode D1), therefore the sub-circuit "B" would have negligible influence on the aforementioned process of storing charges (electrical energy) generated by the piezoelectric element as it is subjected to a very short duration loading to its equivalent capacitor $C_p$. Thus, after the completion of the very short duration impact loading of the piezoelectric element, the charges accumulated in the equivalent capacitor $C_p$ of the piezoelectric element can with relatively high accuracy be considered as a "step" input for this sub-circuit "B" of the energy harvesting device of FIG. 26.

With the step input, the energy is transferred to the capacitor C and inductor L2, FIG. 26, from the equivalent capacitor $C_p$ of the piezoelectric element, FIG. 27. When the equivalent capacitor $C_p$ has discharges essentially all its charges, the diode D2 prevent the energy to be transferred back to the piezoelectric equivalent capacitor $C_p$. The diode D3 allows for the transfer of the energy stored in the inductor L2 to capacitor C. However, when essentially no more energy is left in the inductor L2, the diode D3 prevents the flow of energy from the capacitor C back to the inductor L2. As a result, assuming ideal components, theoretically all the energy stored in the equivalent capacitor $C_p$ of the piezoelectric element can be transferred to the device storage capacitor C. It will be appreciated by those skilled in the art that when using commonly available components, depending on their actual characteristics, for example, resistances in the device inductors and leakage in the capacitors, etc., the actual energy transfer efficiency as well as the overall efficiency of the energy harvesting device of FIG. 26 will be less than their ideal levels.

The process described above for the basic circuitry of the piezoelectric based energy harvesting device was for harvesting the electrical energy that is generated by the piezoelectric element of the device when it is subjected to a very short duration impact type loading and transferring it to a storage capacitor C, FIG. 26, or for using it directly in an electrical or electronic circuitry. It is, however, appreciated by those skilled in the art that once the generated electrical energy is transferred to the storage capacitor C, the piezoelectric element of the device may be subjected to a series of short duration impact type loadings to generate more electrical energy and transfer to the device capacitor C. In the meantime, the electrical energy stored in the storage capacitor C can be used to drive any other electrical or electronic device or charge rechargeable batteries or capacitors or used for any other similar usage. The only requirement is that the short duration charges should be separated enough in time $t_0$ allow the charges stored in the equivalent capacitor $C_p$ of the piezoelectric element, FIGS. 25A and 27, to be essentially transferred to the storage capacitor C. The required time interval between consecutive short duration impact loadings of the piezoelectric element is generally about half the period of the natural oscillation of the LC circuit (inductor L2 and capacitor C) of the sub-circuit "B" of FIG. 26.

It will be appreciated by those skilled in the art that the voltage generated by the compressively loading a piezoelectric element increases (mostly linearly) with the increased level of loading. The electrical energy available in for harvesting is also proportional to the square of the generated voltage. It is therefore highly desirable to achieve as high a voltage as possible in compressive loading of piezoelectric elements to make larger amounts of electrical energy available for harvesting. In certain applications such as in munitions piezoelectric elements where electrical energy is intended to be generated during firing setback acceleration of the munitions or during target impact as were previously described, then the piezoelectric element is subjected to only a single shock loading. In such applications, it is highly desirable to subject the energy harvesting piezoelectric element to a very high compressive loading. However, since the level of compressive loading at which each individual piezoelectric element would fail (be damaged, crushed, broken, fractured or the like) is not exactly known a priori, it is highly desirable to develop a method and means of effectively harvesting electrical energy by high levels of compressive loading that could even cause its complete structural failure. As a result, maximum voltage and therefore electrical energy can be provided by the piezoelectric element for harvesting. Such a method and means are described below.

It will be appreciated by those skilled in the art that when a piezoelectric element is subjected to the aforementioned compressive loading that could be well above its compressive strength, then the piezoelectric element would fail in one of its possible modes of failure, for example, it could be crushed considering the brittle nature of most piezoelectric (ceramic) elements, or fail in shear or other similar modes. As a result of one of the modes of failures, the piezoelectric equivalent capacitor $C_p$, FIG. 25A, may be shorted (closed) or opened (disconnected from the circuit, FIGS. 25A, 26 and 27). However, as it was mentioned previously, since the level of compressive loading at which each individual piezoelectric element would fail and its mode of failure is not exactly known a priori and also since for each mode of failure the result may either be an open or short said circuit equivalent capacitor $C_p$, therefore it is highly desirable to develop a method and means of effectively harvesting electrical energy that is independent of the mode structural failure of the piezoelectric element as well as whether the final state of piezoelectric element equivalent capacitor $C_p$ is a short or open circuitry.

It will be appreciated by those skilled in the art that due to the brittleness of most piezoelectric elements, they can withstand only a fraction of their compressive loading in tension. For this reason, most piezoelectric based energy harvesting devices are designed to subject their piezoelectric elements essentially in compression. The present methods and means of harvesting electrical energy by their high level of loading that can cause their structural failure is therefore described for their compressive loading. The same methods and means can be similarly be utilized to harvest electrical energy from piezoelectric elements when they are subjected to tensile loading that can cause them to structurally fail.

In general, the present one-time-use energy harvesting devices using the present methods and means of harvesting electrical energy from high levels of loading of piezoelectric elements are of interest in munitions for harvesting electrical energy during the firing setback and/or during target impact. The present effectively one-time-use energy harvesting devices may also be of interest in machinery or other structures for powering sensors or the like (or even to act as sensors) for detecting failure or other emergency conditions and transmitting appropriate signals to the machine controls or operators or to appropriate monitoring systems for taking appropriate measures to minimize damage to the affected machinery or perform maintenance or service and the like to prevent a chain of failures in structures or the like. In any case, such events are expected to occur very rapidly and are thereby so assumed in the following embodiments.

Figure 30:
FIG. 30 illustrates circuitry of another piezoelectric-based energy harvesting embodiment for harvesting electrical energy when the device piezoelectric element is subjected to high compressive loads that could cause its structural failure.

The basic circuitry of a piezoelectric-based energy harvesting device embodiment for harvesting electrical energy when the device piezoelectric element is subjected to high compressive loads that could cause its structure to fail is shown in FIG. 30. As was previously described, the stand-alone piezoelectric (usually in stack form) element of this device can also be modeled as a capacitor $C_p$ connected in parallel to a charge source Q as shown in FIG. 25A, and the element would also function as was described for the model of FIG. 25A.

The energy harvesting device described by the circuit diagram of FIG. 30 also operates in two stages as will be described in more detail. In the first stage, the energy generated by the piezoelectric element upon being subjected to rapidly increasing compressive loading such as those that would be experienced during firing setback or (target) impact or other similar events is partly stored in the inductor L due to the generated current pulse and partly in the storage capacitor $C_s$, FIG. 30. In the second stage, the energy stored in the inductor L is also transferred to the storage capacitor $C_s$.

Figure 31:
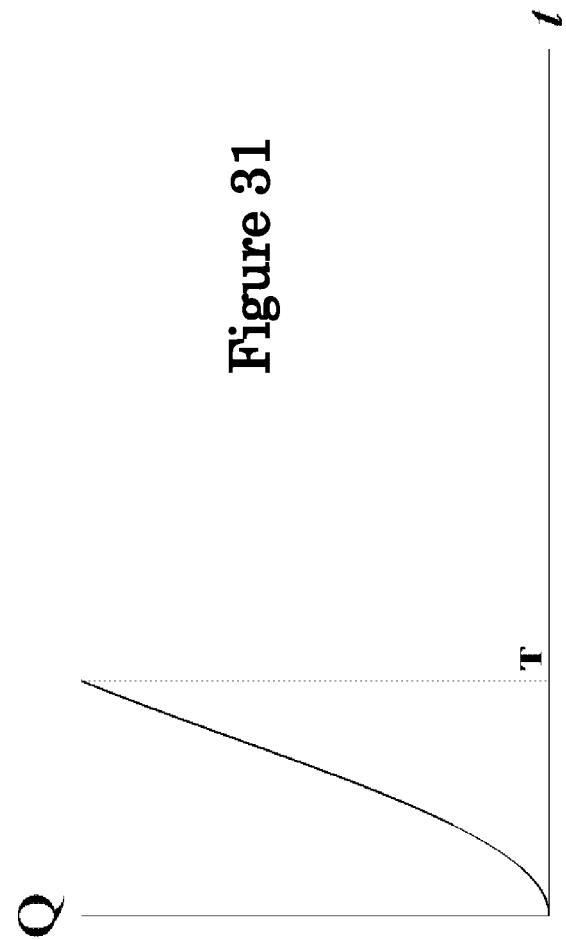
FIG. 31 is the plot of the generated piezoelectric charge profile as a function time during a typical rapid compressive loading of the piezoelectric element up to its structural failure.

A typical plot of the charges generated by a piezoelectric element as a function of time when subjected to a rapidly applied compressive loading is shown in FIG. 31. In this plot, the applied compressive load is considered to be rapidly increasing until at a time T the piezoelectric element fails (breaks, is crushed, or the like), when the as a result of said structural failure, the piezoelectric equivalent capacitor $C_p$, FIG. 25A, may be shorted (closed) or opened (disconnected from the circuit, FIGS. 25A, 26, 27 and 32). In the plot of FIG. 31, the essentially vertical voltage drop at the time T indicates that after the failure event, the charges generated by the piezoelectric element are no longer available for harvesting.

In the aforementioned first stage, the piezoelectric element is being subjected to rapidly increasing compressive loading and would generate increasing amounts of charges as shown in the plot of FIG. 31. During this time period, since the voltage $V_p$ is always positive, the diode D1 can be treated as open loop and the diode D2 can be treated as a close loop since the current flow is always in the direction of the inductor L towards and through the capacitor $C_s$, FIG. 30. As a result during the time period, the circuitry of FIG. 30 functions as its equivalent circuitry shown in FIG. 32. During this stage, the energy generated by the piezoelectric element as it is being subjected to rapidly increasing compressive loading such as those that would be experienced during firing setback or (target) impact or other similar events is partly stored in the inductor L due to the generated current (pulse) and is partly stored in the storage capacitor $C_s$, FIG. 32.

Figure 33:
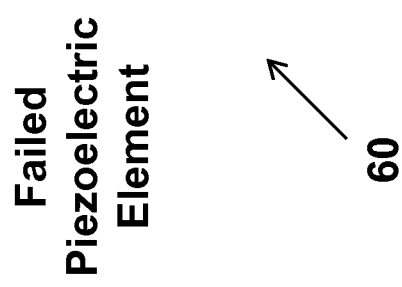
FIG. 33 illustrates the equivalent circuitry of the device of FIG. 30 after the piezoelectric element of the device has structurally failed.

At the time T, FIG. 31, the piezoelectric element is considered to fail structurally, and as it was described previously, depending on the mode of failure experienced and final state of the piezoelectric element, the piezoelectric equivalent capacitor $C_p$, FIG. 25A, may be shorted (closed) or opened (disconnected from the circuit, FIGS. 25A, 26 and 27). Thus, from the time T, i.e., after the piezoelectric element has structurally failed, the piezoelectric element may be modeled as a switch in the device circuitry of FIG. 30 as shown in FIG. 33, in which it is also indicated by the numeral 60. The switch 60 may, however, be either open or closed as it was described depending on its mode of failure and its actual construction and it final state and the like (in FIG. 33 it is shown as being open). As can be seen in FIG. 33, once the piezoelectric element has failed, the diodes D1 and D2 must be considered present in the circuitry and function as will be described below, noting that the diode D2 forces the current $i_2$ to stay positive or be zero and that diode D1 will be connected in parallel to the failed piezoelectric element (and its equivalent switch 60), as a result the current $i_2$ can still flow either through the diode D1 (when the switch 60 is open) or both the diode D1 and the switch 60 when the switch 60 is closed. Thus, the status (open or closed) of the switch 60 will not affect the operation of this circuitry as is described below.

In general and to achieve high energy harvesting efficiency, the period of oscillation of the LCs circuit (without the diodes D1 and D2) must be at least twice the impact time duration T. In addition, since the piezoelectric element can produce high voltage levels at the aforementioned compressive load levels (sometimes well over 200 Volts), therefore the capacitance of the storage capacitor $C_s$ must be significantly higher than that of the equivalent piezoelectric element capacitance $C_p$.

The operation of the basic circuitry of the energy harvesting device shown in the circuit diagram of FIG. 30 during its aforementioned two stages can be described as follows. As the process of compressive loading of the piezoelectric element begins, the charges generated by its compressive loading produces current the $i_1$, FIG. 32, which would branch into the currents $i_2$ and $i_3$. The (positive) current $i_3$ will then begin to accumulate charges in the equivalent piezoelectric element capacitor $C_p$, thereby causing the voltage $V_p$ to keep to increase. The current $i_2$ cannot increase instantly in response to the current $i_1$ due to the presence of the inductor L which limits the rate of change in the current passing through it (i.e., the current $i_2$) and keeps it proportional to the voltage across the inductor L. Thereby the energy generated by the piezoelectric element during this period is transferred to the inductor L as well as the capacitors $C_p$ and $C_s$. Here the energy stored in the capacitor $C_p$ is proportional to the square of the voltage $V_p$, and the energy stored in the inductor L is proportional to the square of the current $i_2$.

Figure 34:
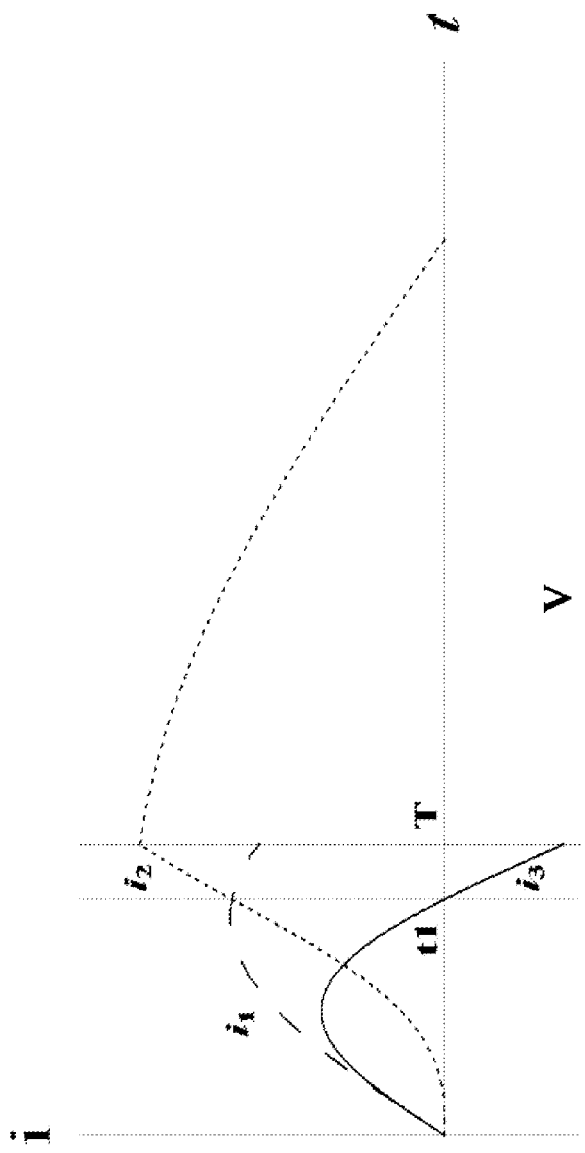
FIG. 34 is a typical plot of the generated currents in the circuitry of the piezoelectric-based energy harvesting device of FIG. 30 when subjected to a rapidly increasing compressive load until its structural failure.
Figure 35:
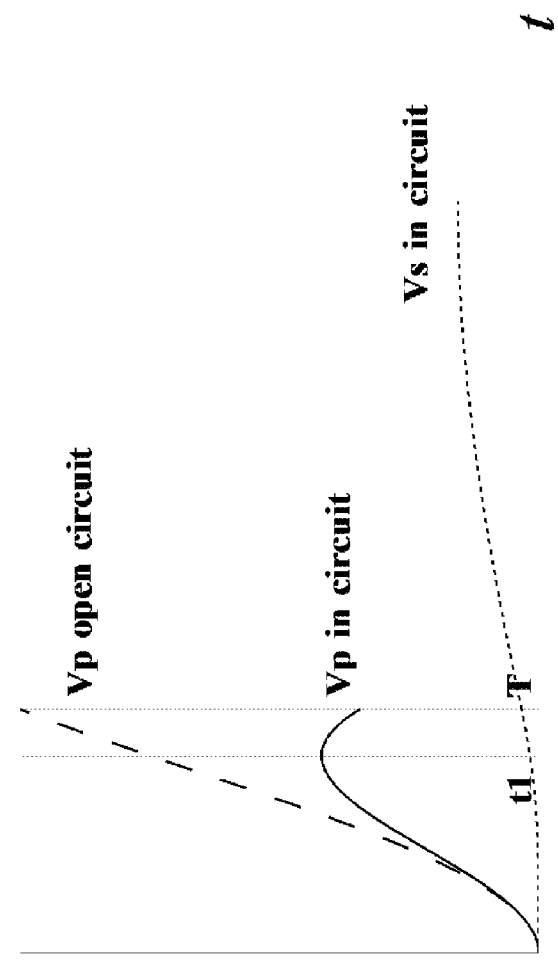
FIG. 35 is a typical plot of the generated voltages in the circuitry of the piezoelectric-based energy harvesting device of FIG. 30 when subjected to a rapidly increasing compressive load until its structural failure.

The general current and voltage profiles when an energy harvesting device with basic circuitry shown in FIG. 30 is subjected to rapidly increasing compressive loading until its structural failure as was previously described are shown in the plots of FIGS. 34 and 35, respectively. In this example, the period of oscillation of the LCs circuit (without the diodes D1 and D2) is considered to be twice the impact time duration T and the capacitance of the storage capacitor $C_s$ is considered to be 20 times that of the capacitance of the equivalent piezoelectric element capacitor $C_p$.

During the time period up to the failure of the piezoelectric element at time T, the open circuit voltage $V_p$ of the piezoelectric element and the stored voltage on the storage capacitor $V_s$ would have the typical profile shown in FIG. 35, noting that since the capacitance of the storage capacitor $C_s$ is considered to be significantly higher (in this case about 20 times higher) than the capacitance of the equivalent piezoelectric capacitor, the storage capacitor voltage $V_s$ will be significantly lower than lower than that of the open and closed circuit voltage $V_p$ of the equivalent piezoelectric element capacitor $C_p$.

As can be observed in the plots of FIGS. 34 and 35, at a time t1 (before the piezoelectric element time of failure T), the inductor current $i_2$ catches up with the piezoelectric current $i_1$, and since the voltage $V_p-V_s$ (FIGS. 32 and 35) is still positive, therefore the current $i_2$ will still keep on increasing after the time t1. Therefore at the time t1, the current $i_3$ becomes zero and begins to become negative, i.e., the equivalent piezoelectric capacitor $C_p$ begins to discharge into the inductor L. At the time t1, the in circuit voltage $V_p$ on the piezoelectric element also reaches its positive maximum. From the time t1, since the current $i_3$ becomes negative, i.e., since the equivalent piezoelectric capacitor $C_p$ begins to discharge, the in circuit voltage $V_p$ of the capacitor $C_p$ begins to decrease. After the time t1 and until the time of piezoelectric failure T, the energy generated by the piezoelectric element and the energy stored in the equivalent piezoelectric capacitor $C_p$ are transferred to inductor L and the storage capacitor $C_s$.

Figure 32:
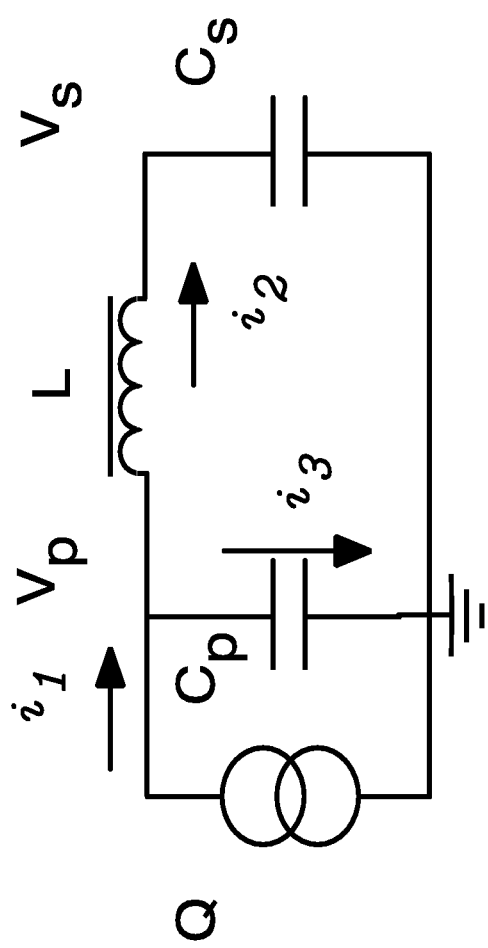
FIG. 32 illustrates an equivalent circuitry of the circuitry of FIG. 30 that is valid during rapid compressive loading of the piezoelectric element prior its structural failure.

At the time T the piezoelectric element is considered to have been structurally failed (i.e., crushed or fractured or the like), thereby the remaining electrical energy that is stored in the equivalent piezoelectric capacitor $C_p$ is no longer available and the charge source is no longer generating any electrical energy. Such a state of the piezoelectric-based energy harvesting device of FIGS. 30 and 32 is shown in the schematic circuit of FIG. 33, with the failed piezoelectric element illustrated as the switch 60 which has been suddenly opened at the time T. As a result, the current $i_2$ can only flow in the direction of charging the storage capacitor $C_s$, FIG. 33. At this time, the voltage across the inductor L suddenly changes from $V_p-V_s$ to $-V_s$ by the failure of the piezoelectric element (as $V_p$ is suddenly dropped to zero), and the energy stored in the inductor L continues to be transferred to the capacitor $C_s$ until the current $i_2$ drops to zero. The diodes D1 and D2 are seen to shut the current loop off when all the inductor L energy is transferred to the storage capacitor $C_s$, and prevent the electrical energy stored in the storage capacitor $C_s$ from being discharged. In this example used to get the plots of FIGS. 34 and 35, the energy harvesting efficiency (indicating the percentage of electrical energy that has become available for harvesting that is transferred to the storage capacitor $C_s$) was found to be around 48%. As expected, the final voltage $V_s$ of the storage capacitor $C_s$ is seen in FIG. 35 to be lower than open circuit voltage $V_p$ of the piezoelectric element since the capacitance of the capacitor $C_s$ was considered to be 20 times higher than that of the equivalent piezoelectric capacitor $C_p$.

It is also appreciated by those skilled in the art that once the piezoelectric element of the above energy harvesting device, FIG. 30, has structurally failed, the circuit across the piezoelectric element may end up to be either open (as shown by the open switch 60 of FIG. 33), or may result in shorting the diode D1, which could be indicated as a closed switch 60. In either case, the current $i_2$ that is flowing through the inductor L to charge the storage capacitor $C_p$ will pass through the diode D1 (when the switch 60 is open) or through the diode D1 and the switch 60 (when the switch 60 is closed). As a result, above state of the structurally failed piezoelectric element would essentially not affect the energy harvesting efficiency of the present energy harvesting embodiment.

In many applications, an object is subjected to one or of a series of relatively short duration shock loadings that may be separated by relatively very short time intervals. It is noted that hereinafter, a shock loading event is referred to those events in which an object is subjected to a rapidly increasing loading followed by a similarly rapidly dropping of the loading level, essentially to the pre-shock loading levels, such as those experienced by munitions during the firing or as they encounter and travel through significant barriers as shown schematically in FIG. 22. It is also appreciated by those skilled in the art that such shock loadings are also routinely assumed to be properly representable by the so-called half sine loading (or acceleration) profile similar to the plot of charges as a function of time shown in FIG. 25B. This is for example the case when an object is impacted by one or multiple objects traveling at relatively high speed or if an object traveling at relatively high speed impacts one or multiple objects or impacts one or multiple barriers that are positioned at relatively close distances. The latter condition is experienced for example by munitions impacting one or multiple barriers of relatively significant strength that are positioned relatively close to each other. In such cases, the main shortcoming of currently available sensors such as different types of available accelerometers is that when such barriers induce relatively large shock loading, then before the vibration and other shock loading induced and generally oscillatory outputs from the sensor has been "damped" out, the next shock loading may occur. As a result, it becomes extremely difficult, and in many cases, impossible to isolate the sensor response from subsequent shock loading events. For example, the munitions may experience multiple shock loadings of tens of thousands of G that may last 5-10 milliseconds or less and be as little as 5-10 milliseconds or less apart.

To provide sensors for detecting and measuring profiles of multiple shock loadings that an object such as munitions may encounter and occur very short times apart, methods for designing such miniature sensors and their electronics and the resulting sensory systems must be provided. To achieve this goal, methods and related sensory systems must be provided with the means to minimize the amount of time that it would take the sensory system, including its sensory element, e.g., the piezoelectric element(s), and its structural elements and electronic circuitry would take to dissipate oscillatory mechanical and electrical energy imparted on the sensory system as a result of each shock loading event. That is, following each shock loading event, the oscillatory mechanical and electrical energy, hereinafter referred to as "residual energy", that is passed to the various elements of the sensory system must be substantially dissipated so that the corresponding output level of the sensory system (effectively sensory noise level) is reduced enough to allow for the detection and measurement of the profile of next shock profile with the required precision.

It will be appreciated by those skilled in the art that the aforementioned mostly oscillatory mechanical and electrical energy imparted to the sensory system (residual energy) are mainly in the form of mechanical vibration energy due to the structural flexibility of the various components of the sensory system and as residual electrical charges in the piezoelectric element. The residual electrical charges remaining in the sensor piezoelectric element(s) following a shock loading is readily seen to be mainly due to the leakage and dissipation of the charges in related electrical energy consuming elements of the sensor. This occurs since the piezoelectric element(s) and the related electrical and electronic elements to which it is connected consume certain amount of electrical charges during the shock loading and unloading cycle (hereinafter and for the sake of simplicity, the piezoelectric element(s) are considered to be subjected to pure compressive loading—particularly since piezoelectric elements are commonly used in compression and generally preloaded to ensure that they are not subjected to tensile stresses during the loading cycle since the piezoelectric materials commonly used are highly brittle and cannot resist a significant amount of tensile stresses). Then following the (compressive) shock loading that is considered to generate positive charges on the piezoelectric element, and not considering the vibratory oscillations, the piezoelectric element(s) will tend to return essentially to its initial (unstrained) length, thereby the equivalent of the aforementioned dissipated charges will be generated and accumulated on the piezoelectric element as negative charges (opposite to the positive charges generated as the result of the compressive shock loading of the piezoelectric element(s)). This residual negative accumulated charges, if not dissipated rapidly, would reduce the level of the total amount of charges that will be generated during the next shock loading cycle, thereby negatively affecting the accuracy with which subsequent shock loading events can be detected and measured.

In the following embodiments, methods to dissipate the aforementioned residual energies in the present sensors for detecting and measuring profiles of multiple shock loadings that an object such as munitions may encounter and occur very short times apart and related sensory systems are disclosed. The presented methods and resulting sensory systems do not require external power to suppress the residual energies following each shock loading event, i.e., they are totally passive. However, methods to dissipate the aforementioned residual energies as well as resulting sensory systems that use external power sources to increase the effectiveness of the sensory system is also provided. An advantage of passive sensory systems is that even though their effectiveness may be relatively less than externally powered ("active") systems in certain applications and for certain shock loading profiles, their operation is always fully stable.

In the following embodiments, in addition to methods to dissipate the aforementioned residual energies in the present sensors for detecting and measuring profiles of multiple shock loadings that an object such as munitions may encounter and occur very short times apart and related sensory systems, methods and related devices to minimize the response of the sensory system to structural vibration and so-called ringing (stress wave induced) reaction of the object to which the present sensory system is attached are also provided. The disclosed methods and devices include those that are fully passive, i.e., do not require external sources of electrical energy, as well as those that utilize externally provided electrical energy.

Figure 36:
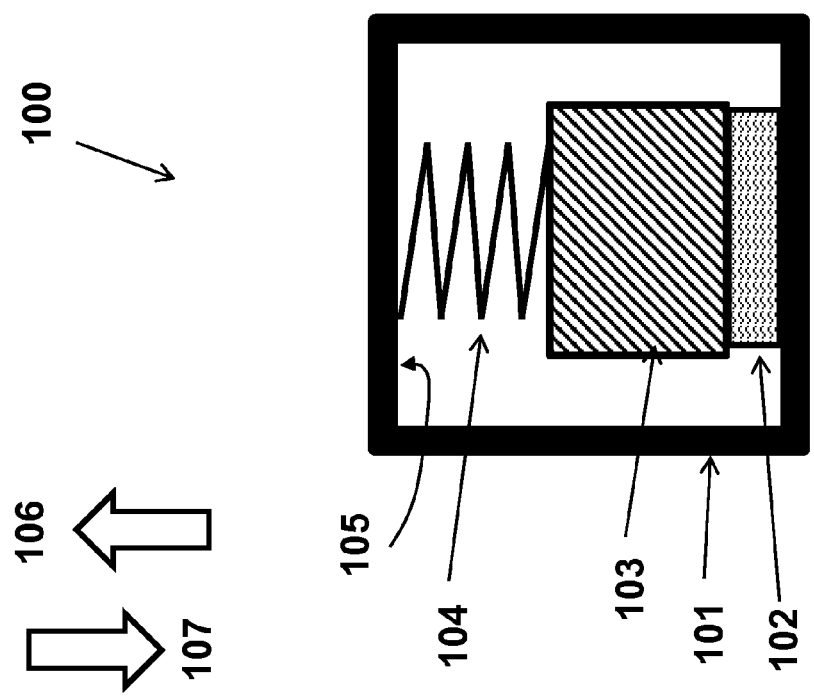
FIG. 36 illustrates a schematic of the packaging of the piezoelectric element of a typical shock loading detection and measurement.

The piezoelectric element of a typical shock loading detection and measurement may be packaged as shown in the schematic of FIG. 36 and indicated by the numeral 100. The piezoelectric element package 100 is provided with a housing 101, which could for example be cylindrically shaped or have any other shape that best matches the available space in the device in which it is being mounted. At least one piezoelectric member 102, which can be stack of piezoelectric members, is fixedly attached to one side of the housing 101 as shown in FIG. 36, i.e., in this case to the bottom surface of the housing 101. A mass 103 of appropriate size which can cover the surface of the piezoelectric element 102 is also generally fixedly attached to the other side of the piezoelectric element as shown in FIG. 36. The inertia (mass) of the mass element 103 is dependent on the maximum level of shock loading to be detected and measured and the material and structural characteristics of the piezoelectric element to withstand the shock loading levels and to retain its piezoelectric characteristics. It will be appreciated by those skilled in the art that for cases of low shock loading levels, larger mass elements 103 are to be used for the sensor to provide detectable levels of output (generated charge voltages). In certain applications in which the levels of shock loading is relatively high, the sensor may not require to be provided with a separate mass element 103 and the inertia (mass) of the piezoelectric element 102 may be enough to generate the detectable output signal. A compressively preloaded spring (elastic) element 104 is also positioned between the interior surface 105 of the housing 101 and the mass element 103 to ensure that as the package 100 of the sensor is subjected to acceleration in either directions shown by the arrows 106 and 107, the piezoelectric element 101 is not subjected to tensile stresses.

Now without any loss of generality, let the shock loading experienced by the sensor piezoelectric package 100, FIG. 36, be directed such that it causes the piezoelectric package 100 to be accelerated (decelerated) in the direction of the arrow 106 (107), thereby causing the mass element to apply the compressive force to the piezoelectric element 102.

Figure 37:
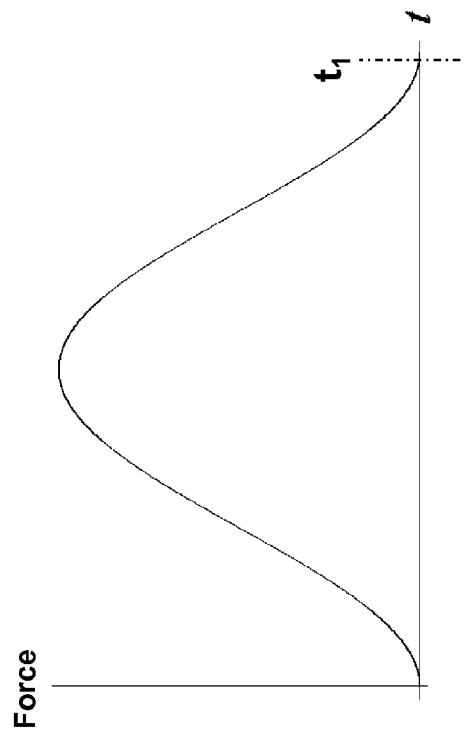
FIG. 37 illustrates a plot of a typical short duration shock loading as a function of time that may be experienced by munitions and to be detected and measured by the provided sensory system.

Also let the compressive shock loading profile that is experienced by the piezoelectric element 102 be as shown in the (compressive) force vs. time plot of FIG. 37, i.e., be similar to the shock loading that can be experienced by the munitions 40 of FIG. 22, to which the present shock loading detection and measuring sensor is attached. As a result, if the output of the piezoelectric element 102 is open and if there were no losses associated with the piezoelectric element and if the object (munitions in this case) does not undergo any vibratory oscillations, then the profile of the charges generated by the piezoelectric element would be similar to that of the compressive force profile of FIG. 37 (similar to the plot of FIG. 25B) (with the same timing cycle).

However, as was previously described, since a portion of the charges generated by the piezoelectric element 102 during the shock loading event is either consumed by the connected sensor circuitry to be described and or dissipated internally due to leakage and the like, therefore at the completion of the shock loading cycle, $t_1$ in FIG. 37, i.e., when the piezoelectric element has essentially returned to its initial strain state, there will be a negative charge (the aforementioned residual charge) left on the piezoelectric element (here it is assumed that the compressive loading of the piezoelectric element 102 due to the shock loading generates a positive charge on the piezoelectric element 102). The purpose of the following embodiment is to rapidly eliminate the residual electrical charges so that the resulting sensory system would not erroneously detect tensile loading of the piezoelectric element, i.e., a "residual" shock loading in the opposite direction.

Figure 38:
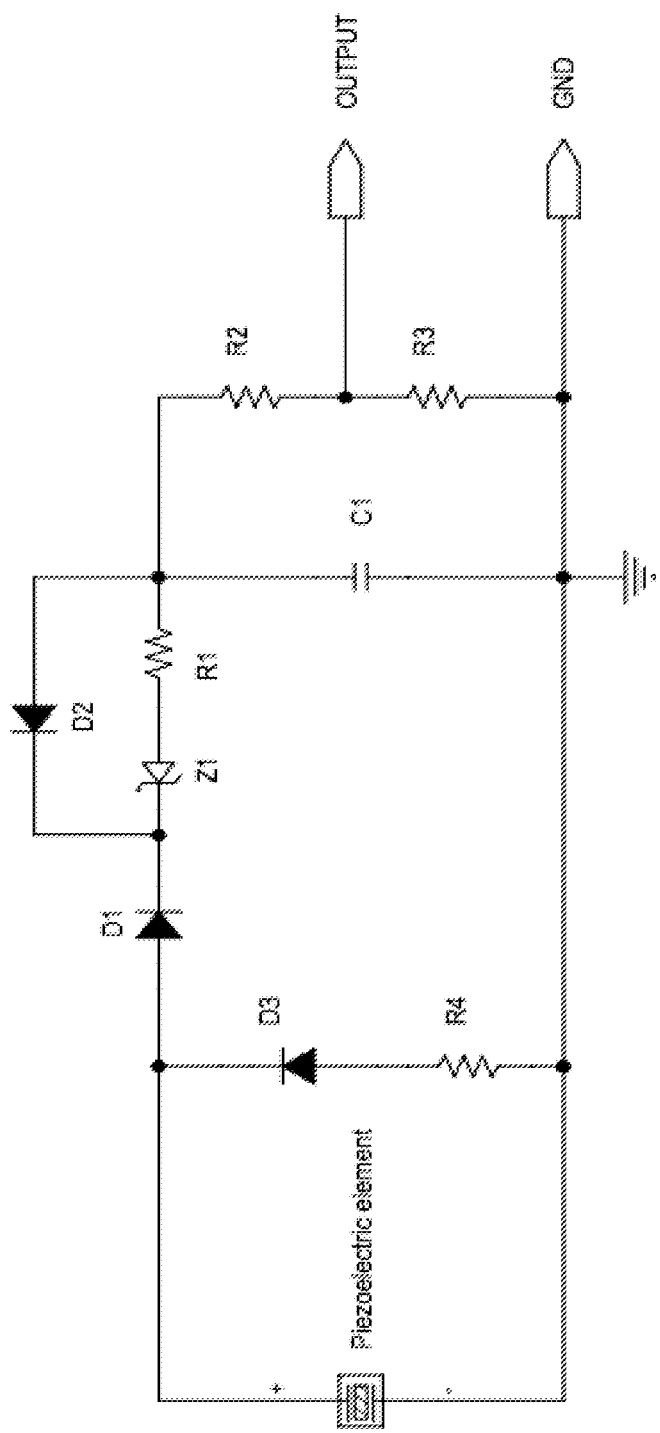
FIG. 38 illustrates circuitry of a first embodiment of the piezoelectric based multiple shock loading detection and shock load profile measuring sensor.

The schematic of the first embodiment of the piezoelectric based multiple shock loading detection and shock load profile measuring sensor is shown in FIG. 38. This circuitry uses the basic safety and all-fire detection circuitry shown in FIG. 13 and functions as was described for the circuitry and is considered to be passive since it does not require any external source of power or batteries or other similar sources of chemical or externally charged power sources for its operation. However as can be seen in the circuitry of FIG. 38 and to rapidly remove the aforementioned residual charges from the piezoelectric element(s) following the application of a shock loading event similar to that of FIG.

37, a pair of serially connected diode D3 and resistor R4 are connected to the terminals of the piezoelectric element as shown in FIG. 38.

Then while the piezoelectric element is under compression as a result of the shock loading, the diode D3 is working at reversed voltage load so there is no current passing through the pair, therefore the pair is inactive and does not change the characteristics of the impact sensing circuitry. It is noted that the piezoelectric element is considered to be designed to provide a positive voltage as a result of the compressive loading. Then as the shock loading cycle ends, i.e., at or close to the time $t_1$ in FIG. 37, the aforementioned residual negative charges remaining on the piezoelectric element is allowed to pass through the diode D3 and will then pass through the resistor R4 and are dissipated. In general, the resistance of the resistor R4 is selected considering the capacitance of the piezoelectric element such that their time constant is close to the shock loading duration to effectively remove the residue energy. In the extreme case, the resistance of R4 can be essentially zero so that the accumulated negative charge is directly released, i.e., the piezoelectric element may be shorted to discharge the aforementioned residual negative charge.

It will be appreciated by those skilled in the art, that with the addition of the diode D3 and relatively low resistance resistor R4 as shown in FIG. 38 to the basic safety and all-fire detection circuitry of FIG. 13, the rectifying diode D1 may then be removed since there will be minimal negative voltage that would be required to be rectified by the diode D1.

As was previously indicated, the second component of "residual energy" imparted to the present piezoelectric based shock loading sensory systems following a shock loading event is in the form of mechanical vibration energy due to the structural flexibility of the various components of the sensory system, including the structural flexibility of the sensor piezoelectric element(s) itself. The purpose of the following (second) embodiment of the multiple shock loading sensory system is to rapidly dissipate this residual energy so that the shock loading event can be measured accurately and that at the end of each shock loading cycle, the output level of the sensory system (effectively sensory noise level) is reduced enough to allow for the detection and precision measurement of the profile of the next shock loading event.

Figure 39:
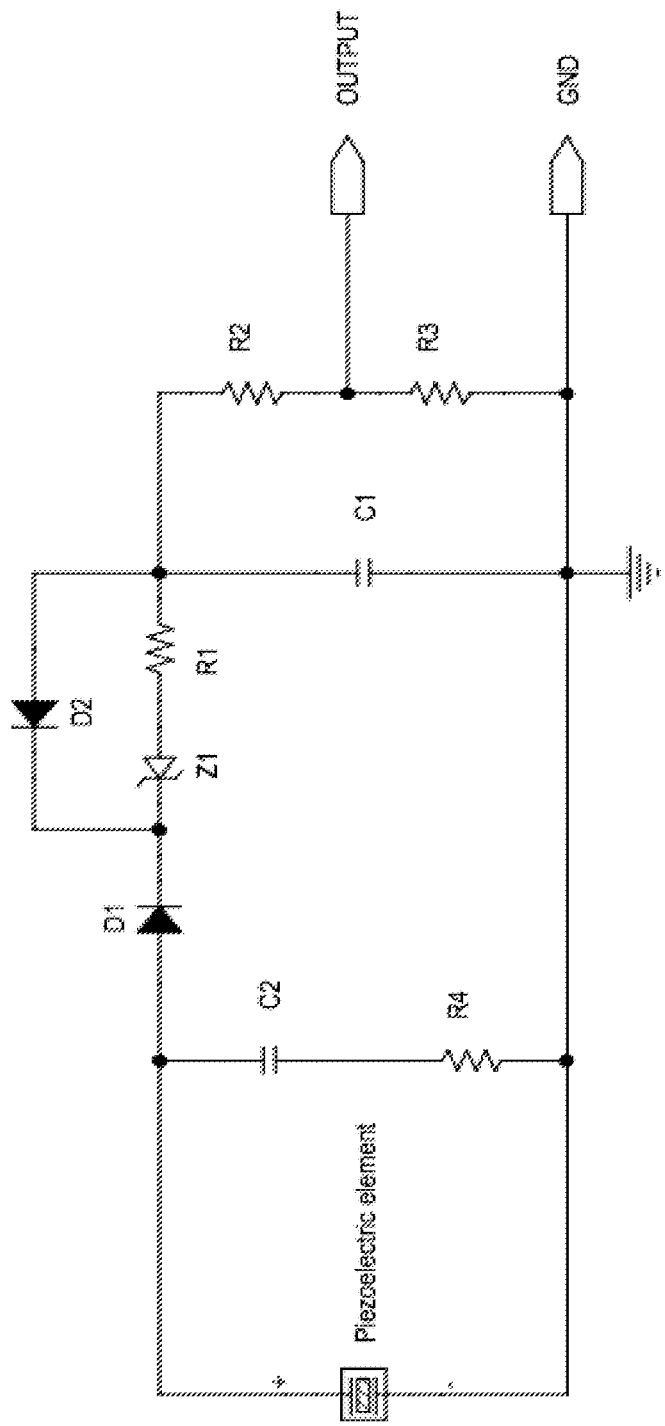
FIG. 39 illustrates circuitry of a second embodiment of the piezoelectric based multiple shock loading detection and shock load profile measuring sensor.

A schematic of the second embodiment of the piezoelectric based multiple shock loading detection and shock load profile measuring sensor is shown in FIG. 39. This circuitry uses the basic safety and all-fire detection circuitry shown in FIG. 13 and functions as was described for the circuitry and is considered to be passive since it does not require any external source of power or batteries or other similar sources of chemical or externally charged power sources for its operation.

It will however be appreciated by those skilled in the art that the developed circuitry for dissipating this component of the mechanical residual (vibrational) energy must function without significantly affecting the shock loading level profile and duration information. It is however noted that when the sensory system is designed properly, the period of the (residual) vibrational energy, i.e., the period(s) natural mode(s) of vibration of the sensory system, is designed to be significantly higher than the duration of the shock loading pulse ($t_1$ in FIG. 37). Thus, by adding the pair of capacitor C2 and resistor R4 or their equivalent to the basic safety and all-fire detection circuitry shown in FIG. 13 as shown in FIG. 39 and by proper selection of the values of the capacitor C2 and the resistor R4, the high frequency component of the piezoelectric output voltage, i.e., the aforementioned (high frequency) mechanical residual (vibrational) energy, is dissipated. It is noted that since the energy dissipated in the resistor R4 is to the second order of such current, the energy dissipated by the addition of the present capacitor C2 and resistor R4 is very sensitive to the signal (piezoelectric output) frequency. Therefore the capacitor C2 and the resistor R4 can be readily selected to effectively remove the vibration residue energy without changing the piezoelectric element output due to the shock loading in terms of its level, profile, and duration.

In certain applications, the present piezoelectric based multiple shock loading detection and shock load profile measuring sensor is mounted on a platform which vibrates in one or more dominant modes of vibration that would thereby cause the sensor piezoelectric element to generate an unwanted output in addition to the shock loading profile to be measured by the sensor as was previously described. In such cases, it is highly desirable to significantly reduce the level of such sensor outputs. In general, the frequencies of such dominant modes of platform vibration (in most systems only one or at most two such modes of vibration are significant) are known or can be readily either calculated or experimentally measured using well known analytical (usually using Finite Element Methods) or experimental (using calibrated hammer impacts) techniques. Therefore, by providing the means of dissipating output (output energy) from the piezoelectric element within a frequency range (window) that includes one or all of the dominant modes of platform vibration without affecting the piezoelectric element output due to the shock loading in terms of its level, profile, and duration. Thereby the performance of the present piezoelectric based multiple shock loading detection and shock load profile measuring sensor is significantly improved.

A third embodiment of the piezoelectric based multiple shock loading detection and shock load profile measuring sensor is intended to dissipate the piezoelectric element output energy in a relatively small frequency range (window) for the purpose of significantly reducing the sensor output caused by the dominant natural mode(s) of vibration of the platform to which the present sensor is attached as was described above.

Figure 40:
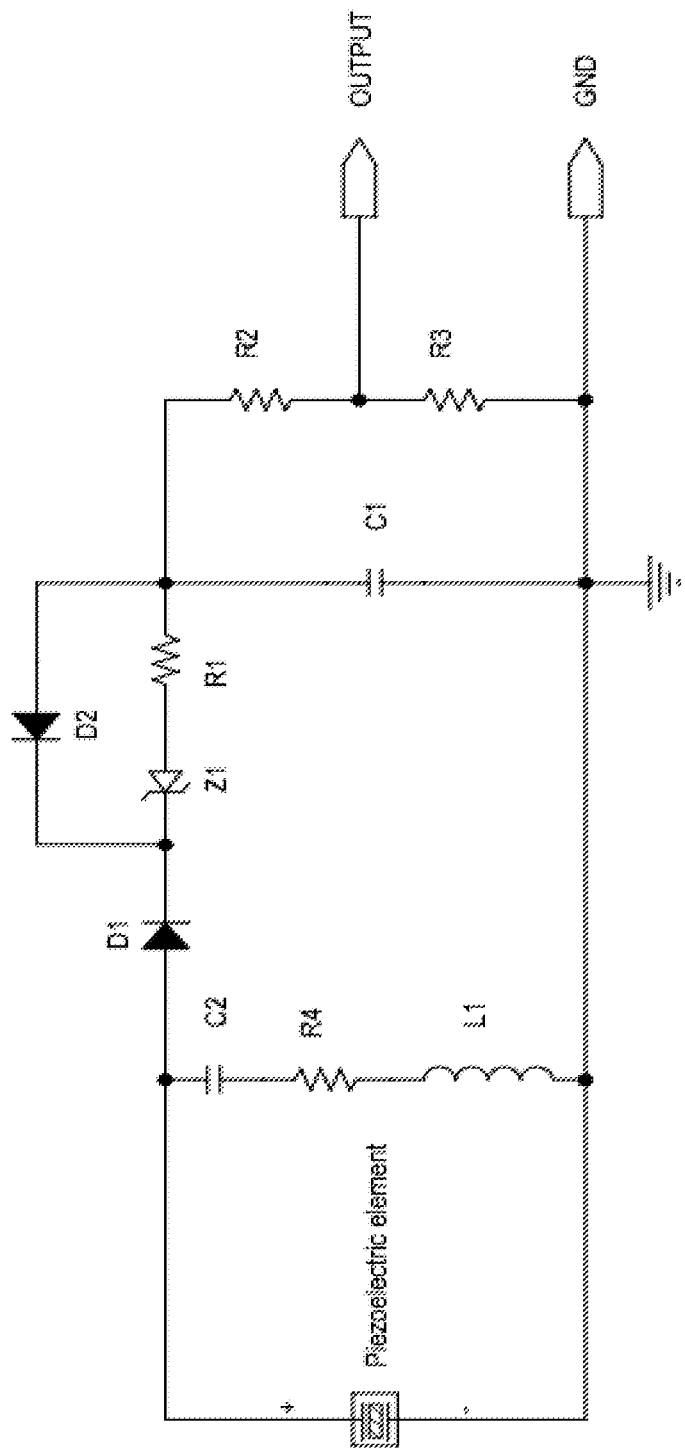
FIG. 40 illustrates circuitry of a third embodiment of the piezoelectric based multiple shock loading detection and shock load profile measuring sensor.

The schematic of this third embodiment of the piezoelectric based multiple shock loading detection and shock load profile measuring sensor is shown in FIG. 40. This circuitry uses the basic safety and all-fire detection circuitry shown in FIG. 13 and functions as was described for the circuitry and is considered to be passive since it does not require any external source of power or batteries or other similar sources of chemical or externally charged power sources for its operation.

In the embodiment of FIG. 40, to significantly dissipate the piezoelectric element output energy in a relatively small frequency range (window) corresponding to the dominant mode(s) of vibrations of the platform to which the present sensor is attached, a serially connected RLC circuitry (resistor R4, inductor L1 and capacitor C2) or their equivalent is added to the basic safety circuitry of FIG. 13. The capacitor C2, resistor R4 and inductor L1 construct an energy dissipating circuitry. The capacitor C2 passes more current for high frequency signal while the inductor passes more current for low frequency signal, so when they are serially connected, the current from the signal (i.e., output of the sensor piezoelectric element) with only a range of frequency mostly passes to the sensor circuitry (through the diode D1), and the energy generated by the piezoelectric element due to the platform vibration (at the aforementioned frequency(ies) of the dominant mode(s) of the platform vibration) is mostly dissipated without affecting the piezoelectric element output due to the shock loading in terms of its level, profile, and duration. Thereby the performance of the present piezoelectric based multiple shock loading detection and shock load profile measuring sensor is significantly improved.

Figure 41:
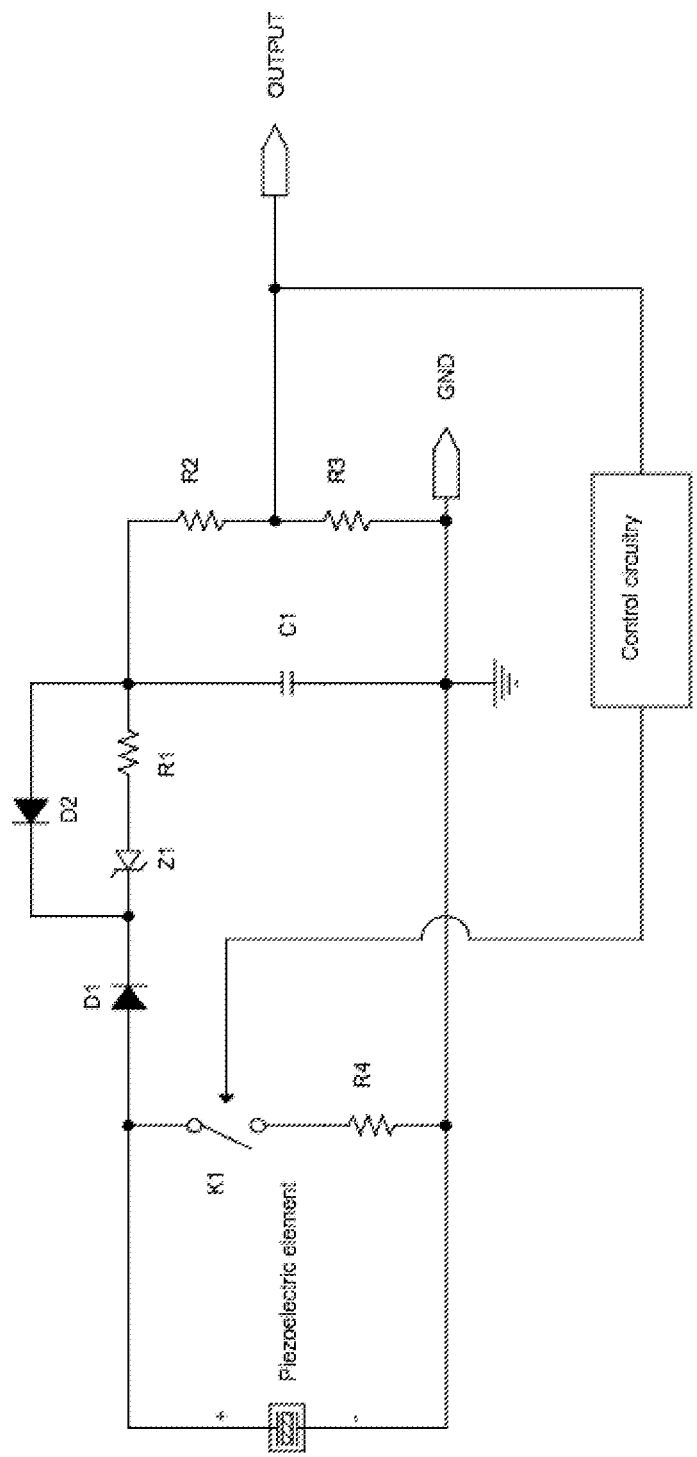
FIG. 41 illustrates a general circuitry of a fourth embodiment of the piezoelectric based multiple shock loading detection and shock load profile measuring sensor.

In a fourth embodiment of the piezoelectric based multiple shock loading detection and shock load profile measuring sensor shown generally in the schematic of FIG. 41, a "control circuitry" is provided to dissipate residual energy of the sensory system (mostly due to vibrational excitation) at the completion of each shock loading cycle ($t_1$ in FIG. 37). The indicated "control circuitry" (examples of which to be described below) is intended to monitor each shock loading profile to detect the end of its cycle ($t_1$ in FIG. 37), and when it is reached, to close the switch K1, causing the electrical energy (charges) in the piezoelectric element and those generated due to the vibration of the platform to which the present sensory system is attached to be dissipated by the resistor R4. The resistance of the resistor R4 should be selected to achieve relatively fast dissipation to minimize the sensor output before the expected occurrence of the next shock loading event. The switch K1 is then preferably opened as soon as the output of the piezoelectric element has dropped below a prescribed level.

Figure 42:
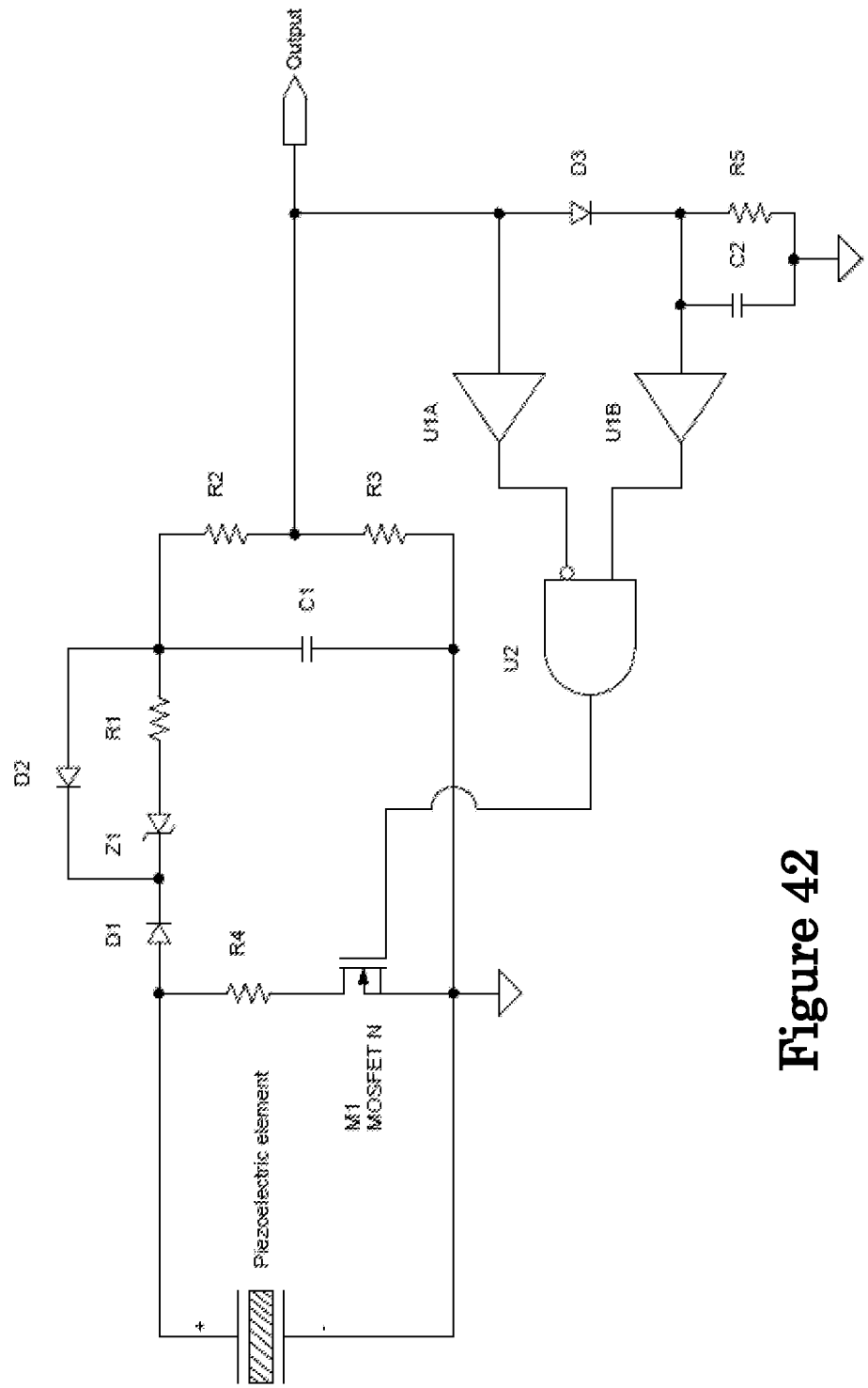
FIG. 42 illustrates one implementation of the general circuitry of the fourth embodiment of the piezoelectric based multiple shock loading detection and shock load profile measuring sensor shown in FIG. 41.

The "control circuitry" component and the switch K1 shown in the circuitry of FIG. 41 may be implemented in many different ways and using many different components. The method and circuitry presented in the schematic of FIG. 42 is intended to represent one such implementation and is not intended to exclude other implementations. In this implementation, the "control circuitry" is designed as shown in FIG. 42, with an N-Channel Mosfet M1 being used to function as the switch K1 (FIG. 41), which is used to close the piezoelectric and resistor R4 energy dissipation loop when a control voltage is applied on the gate pin of M1 when the "control circuitry" detects the end of a shock loading event. The control voltage is provided from the AND logic gate unit U2, which becomes high when the level from the buffer U1A is low and the level from the buffer U2A is high. The buffers U1A and U2A amplify input signal and output them at logic level. U1A takes the safety output signal as input, outputs high level during a shock loading event. U2A takes input from an impact "history-keeping" signal to be described later, which is generated from the diode D3, capacitor C2, and resistor R5, and outputs high level during a shock loading event. The impact history-keeping signal resets itself after a certain amount of time, which is selected to be less than the minimum amount of time between two shock loading events. Therefore, to output control level from the AND gate, two conditions must be true: the shock loading event has ended and the history shows that a shock loading event has occurred at a certain earlier time. When these two conditions are achieved, the Mosfet M1 is enabled and energy dissipation begins via the passing current through the resistor R4.

In the "control circuitry" component of the embodiment of FIG. 42, the "history-keeping" signal is the voltage on the capacitor C2. During a shock loading event, the voltage on the capacitor C2 will follow the signal output voltage from safety circuitry signal (the node between the resistors R2 and R3, FIG. 42). Then when the shock loading ends and the safety circuit output signal drops back to zero (in practice below a prescribed threshold), the diode D3 will prevent the capacitor C2 from discharging back, therefore the impact history information is preserved. In this circuitry, the resistor R5 provides a discharge loop for the capacitor C2 and is used to reset the impact history recording. The reset time determined by the loop RC (R5 and C2) time constant and is set considering the shock loading event durations and time intervals.

It is noted that the energy dissipation loop (containing the resistor R4) does not only discharge the residue energy from the piezoelectric element, but also acts to counter the noise due to the structural vibration of the platform to which the sensor is attached. As a result, the level of noise transmitted to the output circuitry is significantly reduced. Then after the energy dissipation loop (containing the resistor R4) is disconnected (by the opening of the switch K1 in FIG. 41 and Mosfet M1 in FIG. 42) by the aforementioned resetting of the switching action, the piezoelectric element generated noise signal should be relatively low; the energy stored in the capacitor C1 would be essentially zero and the sensor would be ready to detect and measure the profile of the next shock loading event as was previously described.

Figure 43:
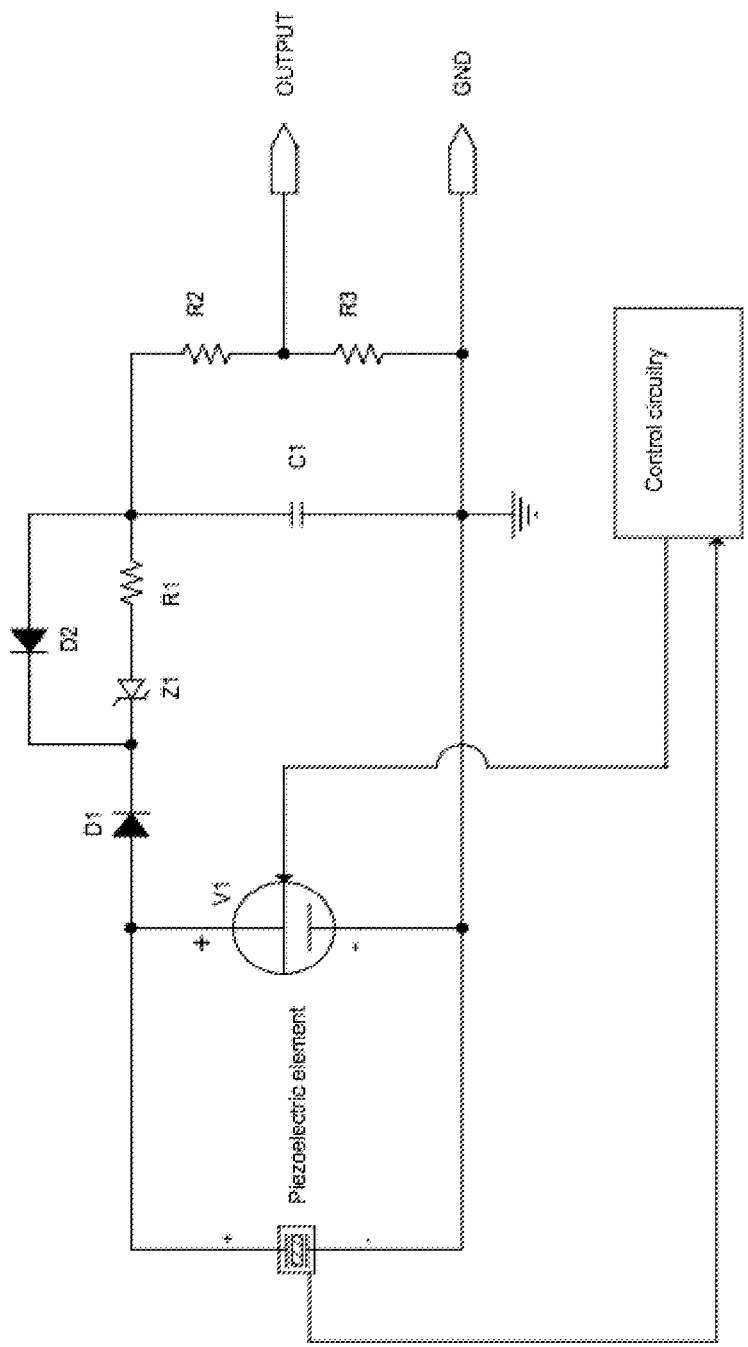
FIG. 43 illustrates another implementation of the general circuitry of the fourth embodiment of the piezoelectric based multiple shock loading detection and shock load profile measuring sensor shown in FIG. 41.

In another implementation of the general embodiment of FIG. 41, a "control circuitry" is used to drive a power source V1 as shown in the schematic of FIG. 43 to effectively remove any one of the aforementioned types of the residue energy stored on or generated by the sensor piezoelectric element. Such "control circuitry" retrieves vibration signal from the output of the piezoelectric element, and would generate an output feedback signal to drive the power source V1 to counter (eliminate) the residue energy. Such a power source may be, but is not limited to, a voltage source, a current source or a charge source, and may be connected to the output of piezoelectric element in series or in parallel, and may be coupled with an inductor or capacitors, and the like, as is well known in the art.

In several of the above embodiments, methods were used to minimize the output of the sensor piezoelectric element due to high frequency vibration of the platform to which the present sensor is attached. In the following embodiments, methods are provided that can be used in addition to the aforementioned methods to significantly reduce the level of high frequency vibrations that are transmitted from the platform to the piezoelectric element of the present sensor. It will be appreciated by those skilled in the art that by high frequency vibrations of the platform to which the present sensor is attached, we refer to those frequencies with periods that are significantly smaller than the duration of the shock loading events to be measured. The high frequency vibration is generally due to the structural vibration and so-called ringing (stress wave induced) reaction of the object such as munitions to which the present sensory system is attached. The disclosed methods and devices include those that are fully passive, i.e., do not require external sources of electrical energy, as well as those that are active, i.e., utilize externally provided electrical energy.

Figure 44:
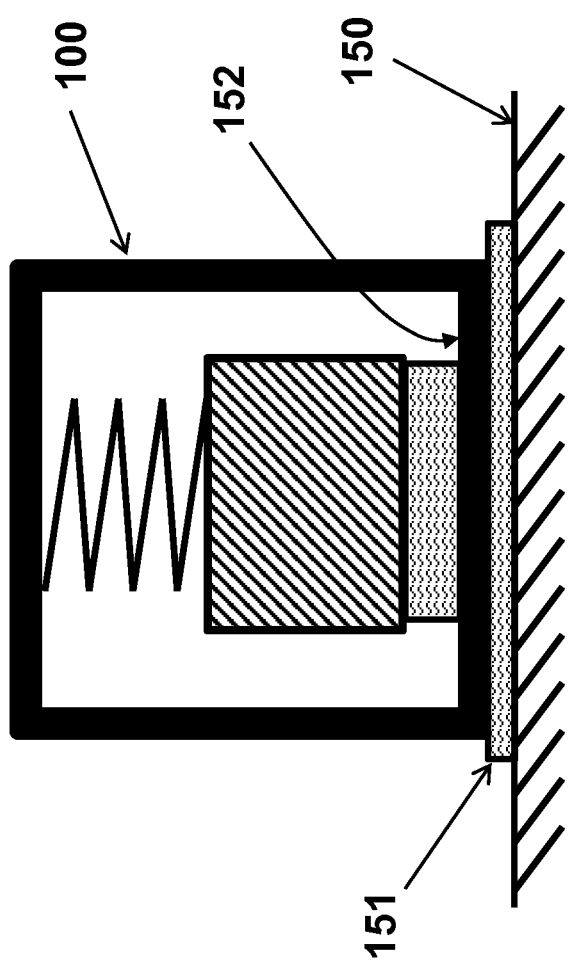
FIG. 44 illustrates an example of providing a vibration isolation layer to prevent high frequency platform vibration from being transmitted to the piezoelectric element of a typical piezoelectric based multiple shock loading detection and shock load profile measuring sensor.

In one such embodiment, the previously described embodiments are attached to the platform that is subjected to shock loading with an intermediate vibration isolation element, such as a resilient layer with proper flexibility and damping characteristics, to isolate the sensor from the aforementioned unwanted relatively high frequency vibration of the platform, for example as shown schematically in FIG. 44, for attaching the packaged piezoelectric element of the shock loading detection and measurement 100 of FIG. 36 to the platform 150 which is to be subjected to multiple shock loading events. Methods to design such vibration isolation elements and the materials appropriate for such purposes are well known in the art.

In the schematic of FIG. 44, the packaged piezoelectric element of the shock loading detection and measurement 100 of FIG. 36 is shown to be attached to the platform 150 which is to be subjected to multiple shock loading events with an intermediate vibration isolation material layer 151. The vibration isolation layer element may be a sheet of resilient and high damping material or consist of several elements and/or materials which are designed to absorb and/or divert high frequency platform vibration, thereby isolating the sensor piezoelectric package 100 from such platform vibrations. The base 152 of the package 100 may be attached by fasteners (not shown) to the structure of the platform 150 with provided vibration isolating resilient washers to prevent the transmission of the platform vibration to the packaged element 100 and thereby the piezoelectric element of the multiple shock loading event measurement sensor. The methods and devices for the design of such vibration isolation devices and proper methods for their attachment to the intended objects are well known in the art and will not be described in detail here.

In a fourth embodiment of the piezoelectric based multiple shock loading detection and shock load profile measuring sensor shown generally in the schematic of FIG. 41, a "control circuitry" is provided to dissipate residual energy of the sensory system (mostly due to vibrational excitation) as the completion of each shock loading cycle ($t_1$ in FIG. 37).

In the general piezoelectric based multiple shock loading detection and shock load profile measuring sensor embodiment of FIG. 41 and its implementation example shown in FIG. 42, a passive method was presented for dissipating the energy remaining in the sensory system, mainly its piezoelectric element and its related mechanical elements (for example see the elements in the piezoelectric packaging of FIG. 36) after the completion of the shock loading event or the aforementioned high frequency energy being transmitted to the system from the platform to which it is attached. The level of the high frequency energy being transmitted from the platform is significantly reduced by the introduction of the passive isolation element such as the element 151 shown in FIG. 44 as was previously described. However, if the level of such transmitted high frequency energy is still excessive and/or if it desired to more rapidly dissipate the aforementioned remaining (mechanical and/or electrical) energy at the completion of the shock loading event, then one may use the electrical energy generated by at least one additional piezoelectric element that is positioned in series or in parallel with the sensor piezoelectric element to rapidly eliminate the remaining or platform transmitted energies. It is appreciated by those skilled in the art that for the case of the (mostly vibrational) energy being transmitted from the platform to the piezoelectric element of the sensors, the added piezoelectric element(s) are in fast providing an active means of isolating the piezoelectric element of the sensor from the platform to which it is attached, i.e., a task similar to that of the high frequency vibration isolation element 151.

Figure 45:
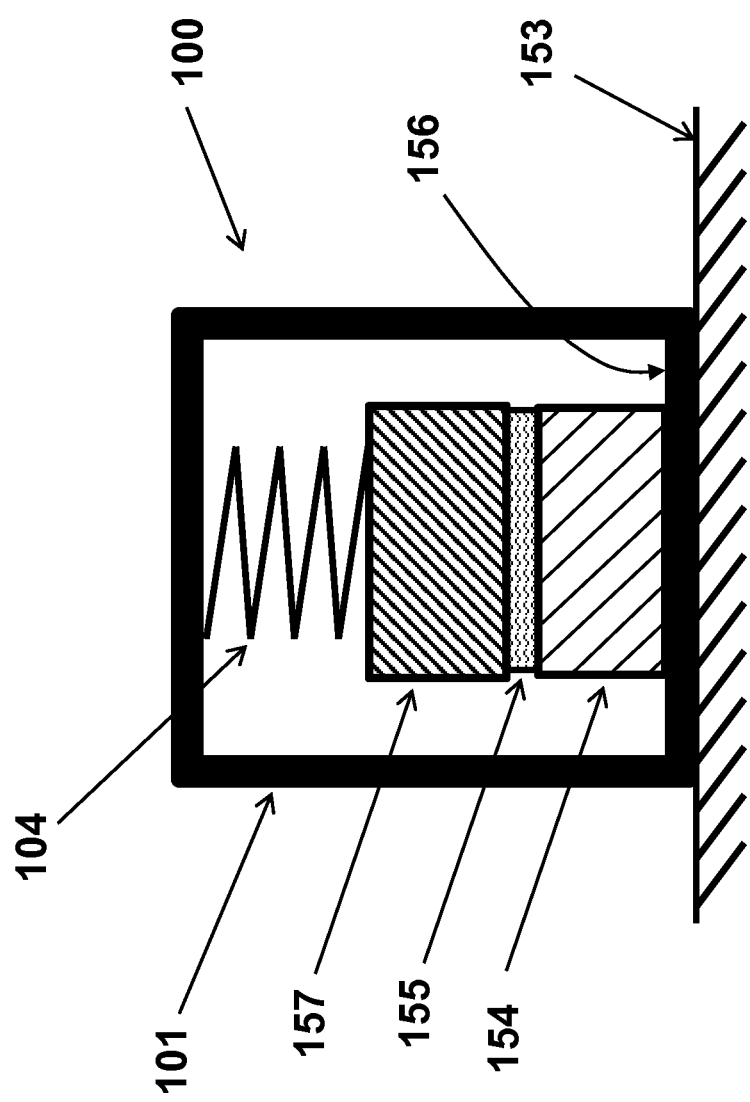
FIG. 45 illustrates an example of the implementation of the method of adding at least one piezoelectric element to actively isolate the piezoelectric element of the present embodiments of the multiple shock loading detection and shock load profile measuring sensors.

An example of such an implementation of the above method with one serially added piezoelectric element is shown schematically in FIG. 45. In the schematic of FIG. 45, the packaged piezoelectric element of the shock loading detection and measurement 100 of FIG. 36 is shown to be attached to the platform 153 which is to be subjected to multiple shock loading events (the intermediate vibration isolation material layer 151 shown in FIG. 44 may also be utilized but is not shown for the sake of clarity). As can be seen in FIG. 45, an additional piezoelectric element 154 is positioned between the sensor piezoelectric element 155 and the base 156 of the piezoelectric packaging 101. The added serially positioned piezoelectric element 154 is to function to actively isolate the sensor piezoelectric element 155 from the vibration of the platform 153 and to dissipate the mechanical and electrical energy of the sensory system, primarily those of the piezoelectric packaged sensor component, once a shock loading event has ended and from high frequency vibrations (as was previously defined to mean those vibrations with periods that are significantly smaller than the duration of the shock loading events) of the platform 153 during the shock loading event.

Figure 46:
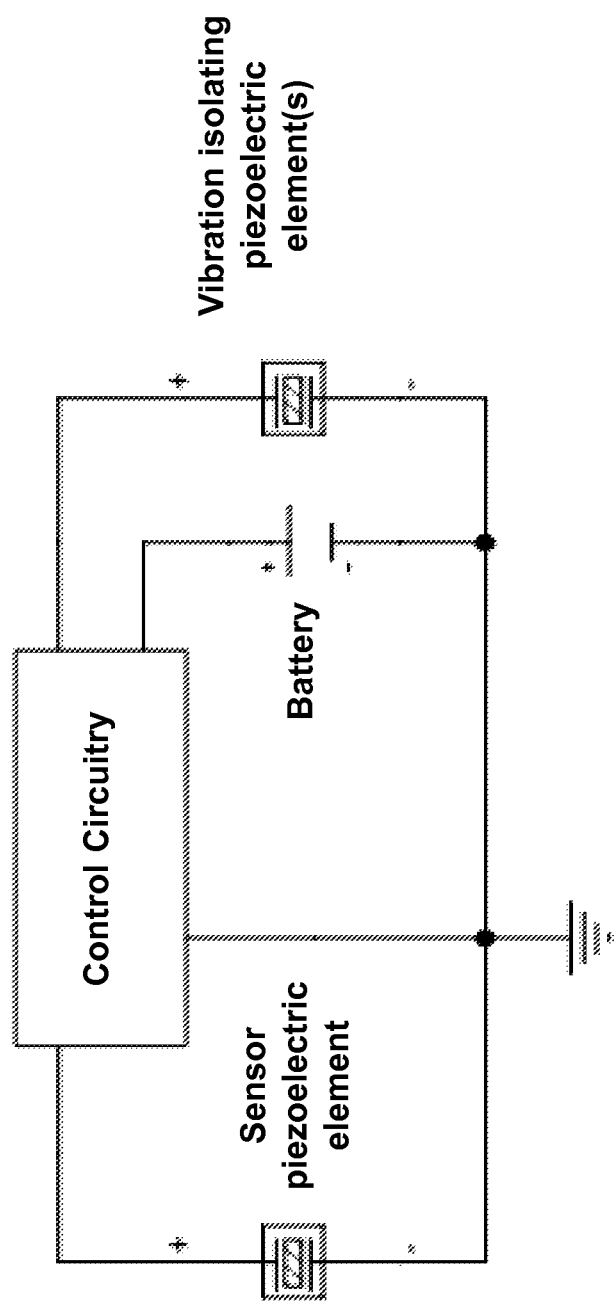
FIG. 46 illustrates the schematic of a typical active isolation circuitry for driving the added at least one piezoelectric element for vibration isolation and dissipating remaining electrical and mechanical energy of the multiple shock loading detection and shock load profile measuring sensor.

The schematic of a typical circuitry for actively driving the aforementioned added at least one piezoelectric element (element 154 in FIG. 45) is shown in FIG. 46. In the circuitry of FIG. 46, the platform vibration induced output of the added at least one "vibration isolating piezoelectric element" (element 154 in FIG. 45) is input to the indicated "control circuitry" element, which based on the output of the element 154, and the current state of the sensor piezoelectric element (element 155 in FIG. 45) would apply an appropriate signal (voltage) to the sensor piezoelectric element as well as the at least one "vibration isolating piezoelectric element" to minimize the transmission of the platform vibration to the sensor piezoelectric element at the completion of a shock loading event. The indicated battery is used to power the operation of the "control circuitry" and drive the added at least one piezoelectric element(s). During the shock loading, the "control circuitry" would similarly prevent the aforementioned high frequency vibration to be transmitted to the sensor piezoelectric element. It will be appreciated by those skilled in the art that to this end, the information as to the detected start and ending of each shock loading event is transmitted (not shown in FIG. 46) to the "control circuitry" of FIG. 46. The "control circuitry" would similarly dissipate (damp out) any residual vibration of the sensory elements (100 in FIG. 45) at the end of each shock loading event.

The various designs for the construction of the "control circuitry" of FIG. 46 and their operation for the aforementioned vibration isolation and vibration damping purposes are well known in the art.

In the circuitry of FIG. 46, a battery is shown to be used to power the operation of the "control circuitry" and drive the added at least one piezoelectric element(s). It is, however, appreciated by those skilled in the art that the electrical energy generated by the added at least one piezoelectric element(s) and to a degree, the piezoelectric element of the sensor may also be harvested as was described in the previous embodiments (FIGS. 24-35) and used to directly power the circuitry of FIG. 46 or supplement the power provided by the indicated circuitry battery.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A shock detection circuit comprising:
   a piezoelectric device configured to generate a voltage over a duration responsive to one or more shock loading events;
   an electrical storage device configured to receive the generated voltage to accumulate a charge;
   an energy dissipating device coupled to the electrical storage device and configured to dissipate the accumulated charge at least one of before and after the one or more shock loading events and not to substantially dissipate the accumulated charge during the one or more shock loading events;

a detector coupled to the electrical storage device and configured to detect a portion of the accumulated charge;

a housing containing the shock detection circuit, wherein the piezoelectric device is fixed to a first portion of an interior surface of the housing; and a compressively preloaded elastic element positioned between a second portion of the interior surface of the housing and the piezoelectric device to configure the piezoelectric device to generate a voltage responsive to acceleration in at least two opposite directions.

2. The shock detection circuit of claim 1, wherein the energy dissipating device comprises a diode and a resistor coupled in series to the electrical storage device.

3. The shock detection circuit of claim 1, wherein the energy dissipating device comprises a capacitor and a resistor coupled in series to the electrical storage device to dissipate the accumulated charge related to mechanical residual energy.

4. The shock detection circuit of claim 1, wherein the detector is configured to compare a voltage at each of a plurality of outputs coupled to the electrical storage device to a corresponding reference voltage to produce a corresponding plurality of accumulated charge results based on the plurality of comparisons.

5. The shock detection circuit of claim 1, wherein the shock detection circuit is a portion of an all-fire detection circuit for an electrically initiated inertial igniter munition.

6. The shock detection circuit of claim 1, comprising a control circuit, wherein the energy dissipating device comprises a switch and a resistor coupled in series to the electrical storage device and the control circuit is configured to detect an end of the one or more shock loading events to close the switch and connect the resistor to the electrical storage device until the accumulated charge is below a predetermined voltage.

7. The shock detection circuit of claim 6, wherein the control circuit is configured to determine whether the shock loading event has occurred within a predetermined period of time and to connect the resistor to the electrical storage device only during the predetermined period.

8. The shock detection circuit of claim 1, comprising a platform and a vibration isolation layer wherein the housing is attached to the platform through the vibration isolation layer.

9. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events;
a detector coupled to the electrical storage device and configured to detect a portion of the accumulated charge; and
a housing containing the shock detection circuit, wherein the piezoelectric device is fixed to a first portion of an interior surface of the housing;
wherein the energy dissipating device comprises a capacitor and a resistor coupled in series to the electrical storage device to dissipate the accumulated charge related to mechanical residual energy; and
an inductor is coupled to the resistor in series with the diode and the resistor, wherein the inductor, the diode and the resistor are selected to be responsive to one or more frequencies within a selected range corresponding to a dominant mode of vibration of the housing.

10. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events; and
a detector coupled to the electrical storage device and configured to detect a portion of the accumulated charge;
wherein the detector is a processor that is configured to record the detected portion of the accumulated charge.

11. The shock detection circuit of claim 10, wherein the processor is configured to record results including the detected portion of the accumulated charge together with an indication of when the detected portion of the accumulated charge occurred.

12. The shock detection circuit of claim 11, wherein the detector is configured to continuously record results together with an indication of when each of the plurality of results occurred.

13. The shock detection circuit of claim 10, wherein the processor is configured to record a plurality of detected portions of the accumulated charge together with an indication of when each of the plurality of the detected portions of the accumulated charge occurred.

14. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events; and
a detector coupled to the electrical storage device and configured to detect a portion of the accumulated charge;
wherein the detector is configured to compare a voltage at each of a plurality of outputs coupled to the electrical storage device to a corresponding reference voltage to produce a corresponding plurality of accumulated charge results based on the plurality of comparisons; and
the reference voltages are selected so that each of the plurality of results are an indication of different levels of an impact.

15. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events; and
a detector coupled to the electrical storage device and configured to detect a portion of the accumulated charge;
wherein the detector is configured to record a plurality of accumulated charge results together with an indication of when each of the plurality of results occurred.

16. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events; and
a detector coupled to the electrical storage device and configured to detect a portion of the accumulated charge;
wherein the shock detection circuit is one of a plurality of shock detection circuits with each oriented to detect a corresponding portion of accumulated charge based on a different direction of motion.

17. The shock detection circuit of claim 16, wherein each of the different directions of motion are orthogonal to each other of the different directions of motion.

18. A shock detection circuit comprising:
a piezoelectric device configured to generate a voltage over a duration responsive to one or more shock loading events;
an electrical storage device configured to receive the generated voltage to accumulate a charge;
an energy dissipating device coupled to the electrical storage device and configured to dissipate the accumulated charge at least one of before and after the one or more shock loading events and not to substantially dissipate the accumulated charge during the one or more shock loading events; and
a detector coupled to the electrical storage device and configured to detect a portion of the accumulated charge;
wherein the piezoelectric device is a first piezoelectric device, the shock detection circuit comprising a second piezoelectric device, wherein the first piezoelectric device is attached to the housing through the second piezoelectric device to dampen vibrations of the housing transmitted to the first piezoelectric device.

19. The shock detection circuit of claim 18, comprising a compressively preloaded elastic element positioned between a second portion of the interior surface of the housing and the first piezoelectric device to configure the first piezoelectric device to generate a voltage responsive to acceleration in at least two opposite directions.

20. The shock detection circuit of claim 19, comprising a mass object sized in a plane perpendicular to the two opposite directions larger than the first piezoelectric device, wherein the mass object is positioned between the elastic element and the first piezoelectric device.

21. A shock detection device comprising:
a first piezoelectric device configured to generate a first voltage over a duration responsive to one or more shock loading events;
a second piezoelectric device configured to generate a second voltage responsive to vibrations of the device;
an control circuit having a first coupling to the first piezoelectric device to receive the first voltage and having a second coupling to the second piezoelectric device to receive the second voltage, wherein the control circuit is configured to generate at least a third voltage on at least one of the first and second couplings to minimize transmission of the vibrations to the first piezoelectric device at least one of before and after the one or more shock loading events.

22. The shock detection device of claim 21, comprising a housing containing at least the first and second piezoelectric devices, wherein the second piezoelectric device is fixed to a first portion of an interior surface of the housing and the first piezoelectric device is fixed to the second piezoelectric device.

23. The shock detection device of claim 22, comprising a compressively preloaded elastic element positioned between a second portion of the interior surface of the housing and the first piezoelectric device to configure the first piezoelectric device to generate a voltage responsive to acceleration in at least two opposite directions.

24. The shock detection circuit of claim 23, comprising a mass object sized in a plane perpendicular to the two opposite directions larger than the first piezoelectric device, wherein the mass object is positioned between the elastic element and the first piezoelectric device within the housing.

* * * * *